United States Patent
Gu et al.

(10) Patent No.: US 7,498,134 B2
(45) Date of Patent: Mar. 3, 2009

(54) HAUSP-MDM2 INTERACTION AND USES THEREOF

(75) Inventors: Wei Gu, New York, NY (US); Muyang Li, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 213 days.

(21) Appl. No.: 10/813,177

(22) Filed: Mar. 29, 2004

(65) Prior Publication Data

US 2004/0265931 A1    Dec. 30, 2004

Related U.S. Application Data

(63) Continuation-in-part of application No. 10/113,732, filed on Mar. 30, 2002.

(51) Int. Cl.
C12Q 1/68       (2006.01)
G01N 33/53     (2006.01)

(52) U.S. Cl. .................. 435/6; 435/6; 435/7.1
(58) Field of Classification Search ............ 435/4, 435/7.21
See application file for complete search history.

(56) References Cited

U.S. PATENT DOCUMENTS 5,702,903 A * 12/1997 Kinzler et al. ................. 435/6
5,720,903 A *  2/1998 Wessling et al. ............ 252/500
2003/0186861 A1 10/2003 Gu et al.

FOREIGN PATENT DOCUMENTS

WO    WO 01/32696 A2    5/2001

OTHER PUBLICATIONS

Li et al. (Nature 2002; 416: 648-653).*
Cummins et al., Disruption of HAUSP gene stabilizes p53. Nature 428:1-2 (2004).
Chung and Baek, Deubiquitinating enzymes: their diversity and emerging roles.
Kashuba, V.I., et al., NotI linking/jumping clones of human chromosome 3:mapping of the TFRC, RAB7 and HAUSP genes to regions rearranged in leukemia and deleted in solid tumors. FEBS Letters 419 (1997) 181-185.
Appella and Anderson, Signaling to p53: breaking the post-translational modification code.
Pathol. Biol. (Paris), 48:227-45, 2000.
Ashcroft et al., Regulation of p53 function and stability by phosphorylation.
Mol. Cell Biol., 19:1751-58, 1999.
Ashcroft et al., Stress signals utilize multiple pathways to stabilize p53.
Mol. Cell Biol., 20:3224-33, 2000.
Ashcroft and Vousden, Regulation of p53 stability.
Oncogene, 18:7637-43, 1999.
Barak et al., mdm2 expression is induced by wild type p53 activity.
EMBO J., 12:461-68, 1993.
Beers and Berkow (eds.), The Merck Manual of Diagnosis and Therapy, 17th ed. (Whitehouse Station, NJ: Merck Research Laboratories, 1999) 973-74, 976, 986, 988, 991.
Blattner et al., DNA damage induced p53 stabilization: no indication for an involvement of p53 phosphorylation.
Oncogene, 18:1723-32, 1999.
Bodansky, M., Principles of Peptide Synthesis (New York: Springer-Verlag New York, Inc., 1984.
Botchkarev et al.; p53 is essential for chemotherapy-induced hair loss.
Cancer Res., 60:5002-02, 2000.
Brooks and Gu, Ubiquitination, phosphorylation and acetylation: the molecular basis for p53 regulation.
Curr. Opin. Cell Biol., 15:164-71, 2003.
Chen et al. (Mapping of the p53 and mdm-2 interaction domains.
Mol. Cell. Biol., 13:4107-14, 1993.
Biochem. Biophys. Res. Commun., 266: 633-640, 1999.
D'Andrea and Pellman, Deubiquitinating enzymes: a new class of biological regulators.
Crit. Rev. Biochem. Mol. Biol., 33:337-52, 1998.
de Graaf et al., Hdmx protein stability is regulated by the ubiquitin ligase activity of Mdm2.
J. Biol. Chem., 278:38315-324, 2003.
Donehower et al., Mice Deficient for p53 are developmentally normal but susceptible to spontaneous tumours.
Nature, 356:215-21, 1992.
Dumaz and Meek, Serine15 phosphorylation stimulates p53 transactivation but does not directly influence interaction with HDM2.
EMBO J., 18:7002-10, 1999.
el-Deiry et al., WAF1, a potential mediator of p53 tumor suppression.
Cell, 75:817-825, 1993.
Everett et al., A novel ubiquitin-specific protease is dynamically associated with the PML nuclear domain and binds to a herpesvirus regulatory protein.
EMBO J., 16:566-77, 1997.
Finch et al., Mdmx is a negative regulator of p53 activity in vivo.
Cancer Res., 62:3221-225, 2002.

(Continued)

Primary Examiner—Brandon J Fetterolf
(74) Attorney, Agent, or Firm—Wilmer Cutler Pickering Hale and Dorr LLP

(57) ABSTRACT

The present invention provides methods for diagnosing neoplasia, assessing the efficacy of therapy to treat neoplasia, assessing the prognosis of a subject who has neoplasia, and treating neoplasia. The present invention also provides a kit for use in detecting neoplasia. The present invention further provides methods for deubiquitinating and/or stabilizing Mdm2 in a cell, and for modulating deubiquitination and/or stability of p53 in a cell. Additionally, the present invention provides a method for identifying a modulator of Mdm2-HAUSP interaction. Also provided is a modulator identified by this method, a pharmaceutical composition comprising the modulator, and use of the modulator in a method of treating neoplasia. The present invention further provides methods for identifying an agent that is reactive with Mdm2 and an agent that is reactive with HAUSP. Also provided are agents identified by these methods. Finally, the present invention provides a complex comprising Mdm2 and HAUSP.

6 Claims, 18 Drawing Sheets

OTHER PUBLICATIONS

Freedman et al., Functions of the MDM2 oncoprotein.
Cell Mol. Life Sci., 55:96-107, 1999.
Giaccia and Kastan, The complexity of p53 modulation: emerging patterns from divergent signals.
Genes Dev., 12:2973-83, 1998.
Gu et al., Mutual dependence of MDM2 and MDMX in their functional inactivation of p53.
J. Biol. Chem., 277:19251-254, 2002.
Gu et al., Synergistic activation of transcription by CBP and p53.
Nature, 387:819-23, 1997.
Haupt et al., Mdm2 promotes the rapid degradation of p53.
Nature, 387:296-99, 1997.
Hemann et al., An epi-alleic series of p53 hypomorphs created by stable RNAi produces distinct tumor phenotypes in vivo.
Nat. Genet., 33:396-400, 2003.
Hengstermann et al., Complete switch from Mdm2 to human papillomavirus E6-mediated degradation of p53 in cervical cancer cells.
Proc. Natl. Acad. Sci. USA, 98:1218-23, 2001.
Hershko et al., The ubiquitin system.
Nat. Med., 6:1073-81, 2000.
Hicke and Dunn, Regulation of membrane protein transport by ubiquitin and ubiquitin-binding proteins.
Annu. Rev. Cell Dev. Biol., 19:141-72, 2003.
Hollstein et al., Database of p53 gene somatic mutations in human tumors and cell lines.
Nucleic Acids Res., 22:3551-55, 1994.
Hollstein et al., New approaches to understanding p53 gene tumor mutation spectra.
Mutat. Res., 431:199-209, 1999.
Holowaty et al., Protein interaction domains of the ubiquitin-specific protease, USP7/HAUSP.
J. Biol. Chem., 278: 47753-47761, 2003.
Holowaty et al., Protein profiling with Epstein-Barr nuclear antigen-1 reveals an interaction with the herpesvirus-associated ubiquitin-specific protease HAUSP/USP7.
J. Biol. Chem., 278:29987-994, 2003.
Honda et al., Oncoprotein MDM2 is a ubiquitin ligase E3 for tumor suppressor p53.
FEBS Lett., 530:25-27, 1997.
Jones et al., Rescue of embryonic lethality in Mdm2-deficient mice by absence of p53.
Nature, 378:206-08, 1995.
Kamijo et al., Tumor suppression at the mouse INK4a locus mediated by the alternative reading frame product p19ARF.
Cell, 91:649-59, 1997.
Kastan et al., A mammalian cell cycle checkpoint pathway utilizing p53 and GADD45 is defective in ataxia-telangiectasia.
Cell, 71:587-97, 1992.
Kawai et al., DNA damage-induced MDMX degradation is mediated by MDM2.
J. Biol. Chem., 278:45946-953, 2003.
Kornitzer and Ciechanover, Modes of regulation of ubiquitin-mediated protein degradation.
J. Cell. Phys., 182:1-11, 2000.
Kubbutat et al., Regulation of p53 stability by Mdm2.
Nature, 387:299-303, 1997.
Lane, D.P., p53, guardian of the genome.
Nature, 358:15-16, 1992.
Laney and Hochstrasser, Substrate targeting in the ubiquitin system.
Cell, 97:427-30, 1999.
Levine, A.J., p53, the cellular gatekeeper for growth and division.
Cell, 88:323-31, 1997.
Linares et al., HdmX stimulates Hdm2-mediated ubiquitination and degradation of p53.
Proc. Natl. Acad. Sci. USA, 100:12009-014, 2003.
Luo et al., Deacetylation of p53 modulates its effect on cell growth and apoptosis.
Nature, 408:377-81, 2000.
Luo et al., Negative control of p53 by Sir2• promotes cell survival under stress.
Cell, 107:137-48, 2001.
Lowe and Sherr, Tumor suppression by Ink4a-Arf: progress and puzzles.
Curr. Opin. Genet. Dev., 13:77-83, 2003.
Michael and Oren, The p53-Mdm2 module and the ubiquitin system.
Semin. Cancer Biol., 13:49-58, 2003.
Migliorini et al., Mdm4 (Mdmx) regulates p53-induced growth arrest and neuronal cell death during early embryonic mouse development.
Mol. Cell Biol., 22:5527-38, 2002.
Modern Techniques of Peptide and Amino Acids Analysis (New York: John Wiley & Sons, 1981.
Montes de Oca Luna et al., Rescue if early embryonic lethality in mdm2-deficient mice by deletion of p53.
Nature, 378:203-06, 1995.
Munger and Howley, Human papillomavirus immortalization and transformation functions.
Virus Res., 89:213-28, 2002.
Nakano and Vousden, PUMA, a novel proapoptotic gene, is induced by p53.
Molecular Cell, 7:683-94, 2001.
Oda et al., Noxa, a BH3-only member of the Bcl-2 family and candidate mediator of p53-induced apoptosis.
Science, 288:1053-58, 2000a.
Oda et al., p53AIP1, a potential mediator of p53-dependent apoptosis, and its regulation by Ser-46-phosphorylated p53.
Cell, 102:849-62, 2000b.
Okamoto and Beach, Cyclin G is a transcriptional target of the p53 tumor suppressor protein.
EMBO J., 13:4816-22, 1994.
Oren, M., Regulation of the p53 tumor suppressor protein.
J. Biol. Chem., 274, 36031-034, 1999.
Pan and Chen, MDM2 promotes ubiquitination and degradation of MDMX.
Mol. Cell Biol., 23:5113-21, 2003.
Parant et al., Rescue of embryonic lethality in Mdm4-null mice by loss of Trp53 suggests a non-overlapping pathway with MDM2 to regulate p53.
Nat. Genet., 29:92-95, 2001.
Pickart, C.M., Back to the future with ubiquitin.
Cell, 116:181-90, 2004.
Prives and Hall, The p53 pathway.
J. Pathol., 187:112-26, 1999.
Rodriguez et al., Multiple C-terminal lysine residues target p53 for ubiquitin-proteasome-mediated degradation.
Mol. Cell. Biol., 20:8458-67, 2000.
Scheffner et al., The HPV-16 E6 and E6-AP complex functions as an ubiquitin-protein ligase in the ubiquitination of p53.
Cell, 75:495-505, 1993.
Seavey et al., The E7 oncoprotein of human papillomavirus type 16 stabilizes p53 through a mechanism independent of p19 (ARF).
J. Virol., 73:7590-98, 1999.
Sherr, C.J., The INK4a/ARF network in tumour suppression.
Nat. Rev. Mol. Cell Biol., 2:731-37, 2001.
Sherr and Webber, The ARF/p53 pathway.
Curr. Opin. Genet. Dev., 10:94-99, 2000.
Shieh et al., DNA damage-induced phosphorylation of p53 alleviates inhibition MDM2.
Cell, 91:325-34, 1997.
Slingerland and Pagano, Regulation of the cdk inhibitor p27 and its deregulation in cancer.
J. Cell Physi., 183:10-17, 2000.
Stad et al., Mdmx stabilizes p53 and Mdm2 via two distinct mechanisms.
EMBO Rep., 2:1029-34, 2001.
Stott et al., The alternative product from the human CDKN2A locus, p14(ARF), participates in a regulatory feedback loop with p53 and MDM2.
EMBO J., 17:5001-14, 1998.
Tolbert et al., p19ARF is dispensable for oncogenic stress-induced p53-mediated apoptosis and tumor suppression in vivo.
Mol. Cell Biol., 22:370-77, 2002.
Tyner et al., p53 mutant mice that display early ageing-associated phenotypes.
Nature, 415:45-53, 2002.

Vogelstein et al., Surfing the p53 network.
Nature, 408:307-10, 2000.
Wilkinson, K.D., Signal transduction: aspirin, ubiquitin and cancer.
Nature, 424:738-39, 2003.
Wilkinson, K.D., Ubiquitination and deubiquitination: targeting of proteins for degradation by the proteasome.
Semin. Cell Dev. Biol., 11:141-48, 2000.

Wu et al., The p53-mdm-2 autoregulatory feedback loop.
Genes Dev., 7:1126-32, 1993.
Yu et al., PUMA induces the rapid apoptosis of colorectal cancer cells.
Molecular Cell, 7:673-82, 2001.

* cited by examiner a
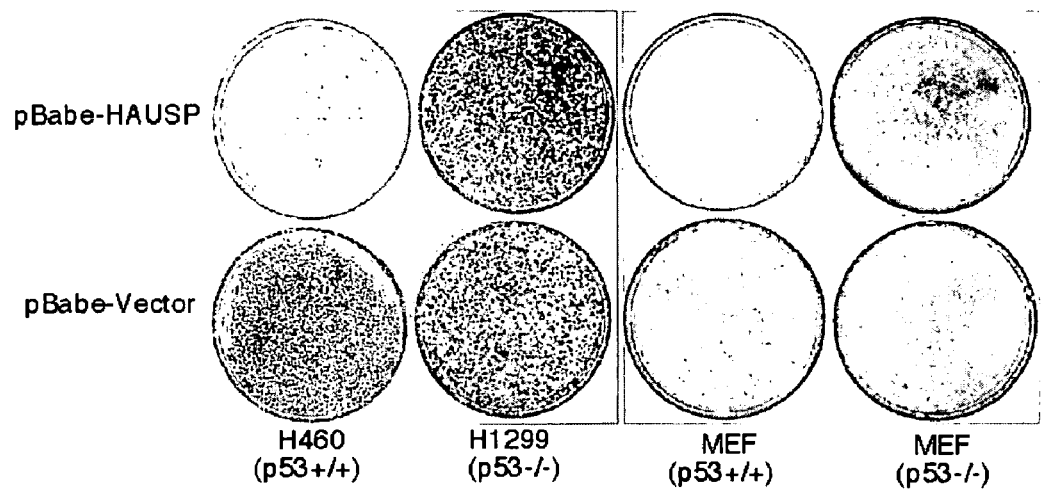
b
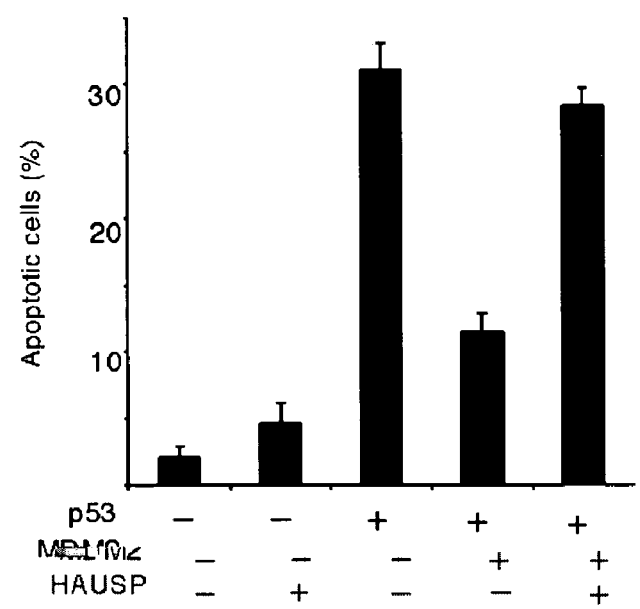
FIG. 3

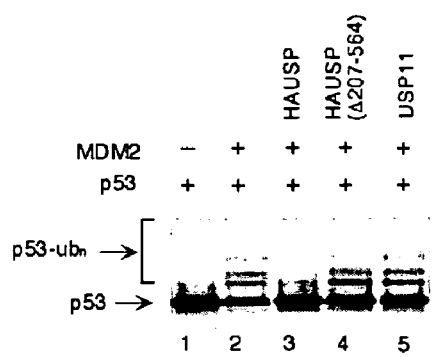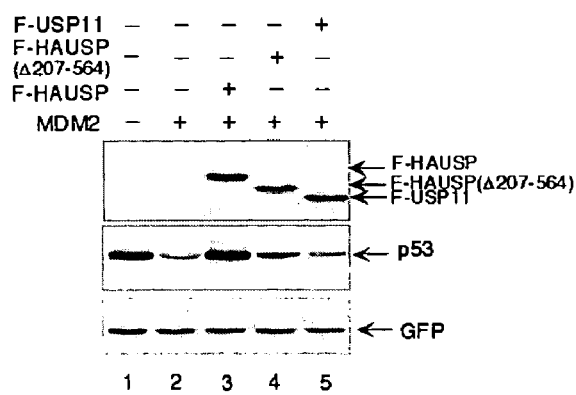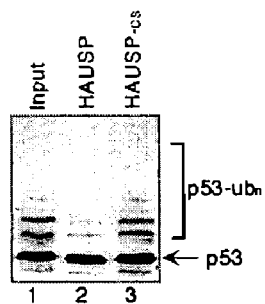
FIG. 4

```
   1 mnhqqqqqqq kageqqlsep edmemeagdt ddppritqnp vingnvalsd ghntaeedme
  61 ddtswrseat fqftverfsr lsesvlsppc fvrnlpwkim vmprfypdrp hqksvgfflq
 121 cnaesdstsw schaqavlki inyrddeksf srrishlffh kendwgfsnf mawsevtdpe
 181 kgfidddkvt fevfvqadap hgvawdskkh tgyvglknqg atcymnsllq tlfftnqlrk
 241 avymmptegd dssksvplal qrvfyelqhs dkpvgtkklt ksfgwetlds fmqhdvqelc
 301 rvlldnvenk mkgtcvegti pklfrgkmvs yiqckevdyr sdrredyydi qlsikgkkni
 361 fesfvdyvav eqldgdnkyd agehglqeae kgvkfltlpp vlhlqlmrfm ydpqtdqnik
 421 indrfefpeq lpldeflqkt dpkdpanyil havlvhsgdn hgghyvvyln pkgdgkwckf
 481 dddvvsrctk eeaiehnygg hdddlsvrhc tnaymlvyir esklsevlqa vtdhdipqql
 541 verlqeekri eaqkrkerqe ahlymqvqiv aedqfcghqg ndmydeekvk ytvfkvlkns
 601 slaefvqsls qtmgfpqdqi rlwpmqarsn gtkrpamldn eadgnktmie lsdnenpwti
 661 fletvdpela asgatlpkfd kdhdvmlflk mydpktrsln ycghiytpis ckirdllpvm
 721 cdragfiqdt slilyeevkp nlteriqdyd vsldkaldel mdgdiivfqk ddpendnsel
 781 ptakeyfrdl yhrvdvifcd ktipndpgfv vtlsnrmnyf qvaktvaqrl ntdpmllqff
 841 ksqgyrdgpg nplrhnyegt lrdllqffkp rqpkklyyqq lkmkitdfen rrsfkciwln
 901 sqfreeeitl ypdkhgcvrd lleeckkave lgekasgklr lleivsykii gvhqedelle
 961 clspatsrtf rieeipldqv didkenemlv tvahfhkevf gtfgipfllr ihqgehfrev
1021 mkriqslldi qekefekfkf aivmtgrhqy inedeyevnl kdfepqpgnm shprpwlgld
1081 hfnkapkrsr ytylekaiki hn
```

FIG. 6

```
   1 gtacgtgcgc gtctccctgc cgccgccgcc gcccgccgcg ggccgccccg gggccgccgt
  61 cgccgacgac gcgcgggagg aggaggagga ggccgccccg ccgccgccgc cgccgccgcc
 121 gccccggctc gccgccgccc gcccgccggg ctcgcagccc cggcccccgg ccgcaggcga
 181 ggcccaggcc gcggccgaca tgaaccacca gcagcagcag cagcagcaga aagcgggcga
 241 gcagcagttg agcgagcccg aggacatgga gatggaagcg ggagatacag atgacccacc
 301 aagaattact cagaaccctg tgatcaatgg gaatgtggcc ctgagtgatg acacaacac
 361 cgcggaggag gacatggagg atgacaccag ttggcgctcc gaggcaacct ttcagttcac
 421 tgtggagcgc ttcagcagac tgagtgagtc ggtccttagc cctccgtgtt ttgtgcgaaa
 481 tctgccatgg aagattatgg tgatgccacg cttttatcca gacagaccac accaaaaaag
 541 cgtaggattc tttctccagt gcaatgctga atctgattcc acgtcatggt cttgccatgc
 601 acaagcagtg ctgaagataa taaattacag agatgatgaa aagtcgttca gtcgtcgtat
 661 tagtcatttg ttcttccata aagaaaatga ttggggatttt tccaatttta tggcctggag
 721 tgaagtgacc gatcctgaga aaggatttat agatgatgac aaagttacct ttgaagtctt
 781 tgtacaggcg gatgctcccc atggagttgc gtgggattca agaagcaca caggctacgt
 841 cggcttaaag aatcagggag cgacttgtta catgaacagc ctgctacaga cgttatttt
 901 cacgaatcag ctacgaaagg ctgtgtacat gatgccaacc gagggggatg attcgtctaa
 961 aagcgtccct ttagcattac aaagagtgtt ctatgaatta cagcatagtg ataaacctgt
1021 aggaacaaaa aagttaacaa agtcatttgg gtgggaaact ttagatagct tcatgcaaca
1081 tgatgttcag gagctttgtc gagtgttgct cgataatgtg gaaaataaga tgaaaggcac
1141 ctgtgtagag ggcaccatac ccaaattatt ccgcggcaaa atggtgtcct atatccagtg
1201 taaagaagta gactatcggt ctgatagaag agaagattat tatgatatcc agctaagtat
1261 caaaggaaag aaaaatatat ttgaatcatt tgtggattat gtggcagtag aacagctcga
1321 tggggacaat aaatacgacg ctgggggaaca tggcttacag gaagcagaga aaggtgtgaa
1381 attcctaaca ttgccaccag tgttacatct acaactgatg agatttatgt atgaccctca
1441 gacggaccaa aatatcaaga tcaatgatag gttgaattc ccagagcagt taccacttga
1501 tgaattttg caaaaaacag atcctaagga ccctgcaaat tatattcttc atgcagtcct
1561 ggttcatagt ggagataatc atggtggaca ttatgtggtt tatctaaacc ccaaagggga
1621 tggcaaatgg tgtaaatttg atgacgacgt ggtgtcaagg tgtactaaag aggaagcaat
1681 tgagcacaat tatgggggtc acgatgacga cctgtctgtt cgacactgca ctaatgctta
1741 catgttagtc tacatcaggg aatcaaaact gagtgaagtt ttacaggcgg tcaccgacca
1801 tgatattcct cagcagttgg tggagcgatt acaagaagag aaaaggatcg aggctcagaa
1861 gcggaaggag cggcaggaag cccatctcta tgcaagtg cagatagtcg cagaggacca
1921 gttttgtggc caccaaggga atgacatgta cgatgaagaa aaagtgaaat acactgtgtt
1981 caaagtattg aagaactcct cgcttgctga gtttgttcag agcctctctc agaccatggg
2041 atttccacaa gatcaaattc gattgtggcc catgcaagca aggagtaatg gaacaaaacg
2101 accagcaatg ttagataatg aagccgacgg caataaaaca atgattgagc tcagtgataa
2161 tgaaaaccct tggacaatat tcctggaaac agttgatccc gagctggctg ctagtggagc
2221 gaccttaccc aagtttgata agatcatga tgtaatgtta ttttgaaga tgtatgatcc
2281 caaaacgcgg agcttgaatt actgtgggca tatctacaca ccaatatcct gtaaaatacg
```

FIG. 7

2341 tgacttgctc ccagttatgt gtgacagagc aggatttatt caagatacta gccttatcct
2401 ctatgaggaa gttaaaccga atttaacaga gagaattcag gactatgacg tgtctcttga
2461 taaagcccctt gatgaactaa tggatggtga catcatagta tttcagaagg atgaccctga
2521 aaatgataac agtgaattac ccaccgcaaa ggagtatttc cgagatctct accaccgcgt
2581 tgatgtcatt ttctgtgata aaacaatccc taatgatcct ggatttgtgg ttacgttatc
2641 aaatagaatg aattattttc aggttgcaaa gacagttgca cagaggctca acacagatcc
2701 aatgttgctg cagttttca agtctcaagg ttatagggat ggcccaggta atcctcttag
2761 acataattat gaaggtactt taagagatct tctacagttc ttcaagccta gacaacctaa
2821 gaaactttac tatcagcagc ttaagatgaa aatcacagac tttgagaaca ggcgaagttt
2881 taaatgtata tggttaaaca gccaatttag ggaagaggaa ataacactat atccagacaa
2941 gcatgggtgt gtccgggacc tgttagaaga atgtaaaaag gccgtggagc ttggggagaa
3001 agcatcaggg aaacttaggc tgctagaaat tgtaagctac aaaatcattg gtgttcatca
3061 agaagatgaa ctattagaat gtttatctcc tgcaacgagc cggacgtttc gaatagagga
3121 aatcccttttg gaccaggtgg acatagacaa agagaatgag atgcttgtca cagtggcgca
3181 tttccacaaa gaggtcttcg gaacgttcgg aatcccgttt ttgctgagga tacaccaggg
3241 cgagcatttt cgagaagtga tgaagcgaat ccagagcctg ctggacatcc aggagaagga
3301 gtttgagaag tttaaatttg caattgtaat gacgggccga caccagtaca taatgaaga
3361 cgagtatgaa gtaaatttga aagactttga gccacagccc ggtaatatgt ctcatcctcg
3421 gccttggcta gggctcgacc acttcaacaa agccccaaag aggagtcgct acacttacct
3481 tgaaaaggcc attaaaatcc ataactgatt tccaagctgg tgtgttcaag gcgaggacgg
3541 tgtgtgggtg gccccttaac agcctagaac tttggtgcac gtgccctcta gccgaagtct
3601 tcagcaagag gattcgctgc tggtgttaat tttatttat tgaggctgtt cagtttggct
3661 tctctgtatc tattgactgc ccttttttgag caaaatgaag atgttttat aaagcttgga
3721 tgccaatgag agttatttta tggtaaccac agtgcaaggc aactgtcagc gcaatgggggg
3781 agaagaggtt agtggatcgg gggtccctgg ctcaaggtct ctgggctgtc cctagtgggc
3841 acgagtggct cggctgcctt cctggggtcc cgtgcaccag ccctgcagct agcaagtctt
3901 gtgtttaggc tcgtctgacc tatttccttc agtta tactt tcaatgacct tttgtgcatc
3961 tgttaaggca aaacagagaa actcacaacc taataaatag cgctcttccc ttcaaaaaaa
4021 aa

FIG. 7 (cont.)

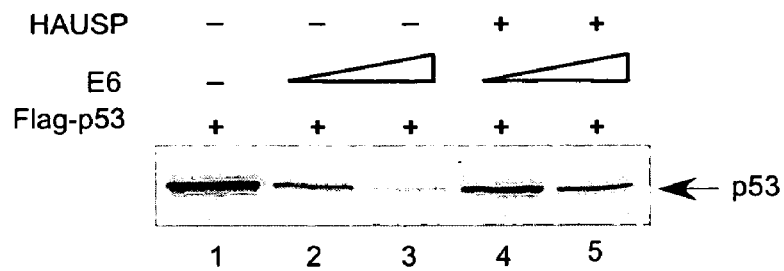
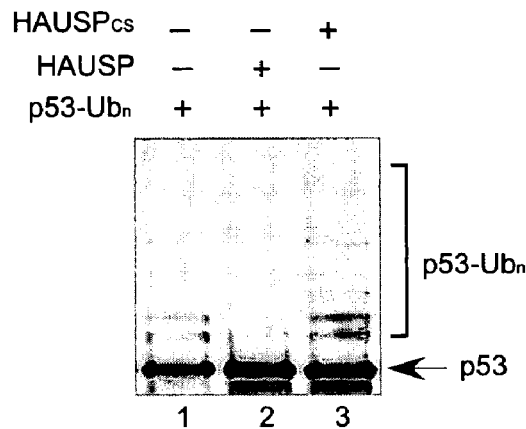
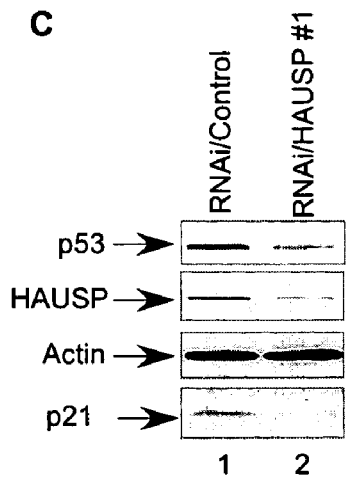
FIG. 13

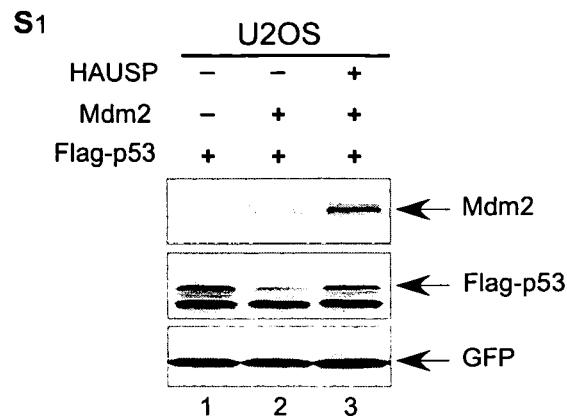
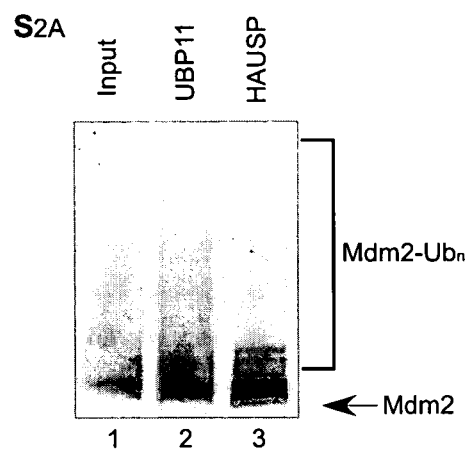
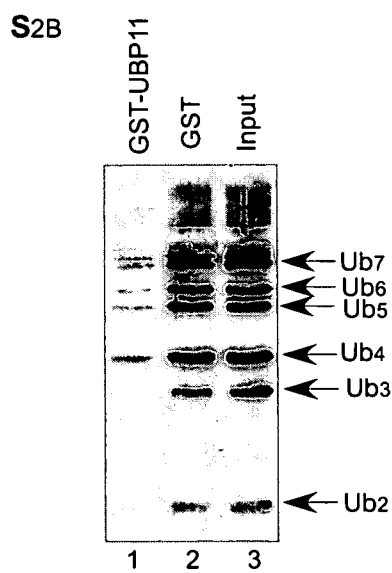
FIG. 14

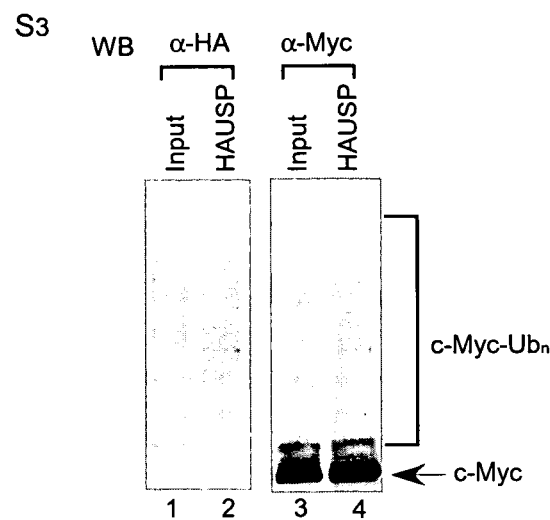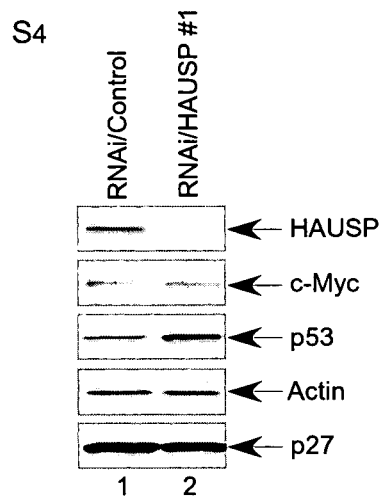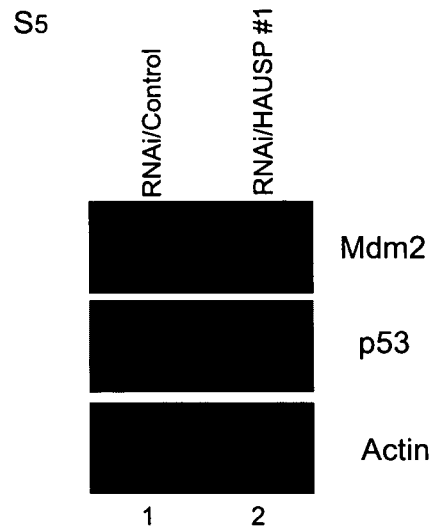
FIG. 15

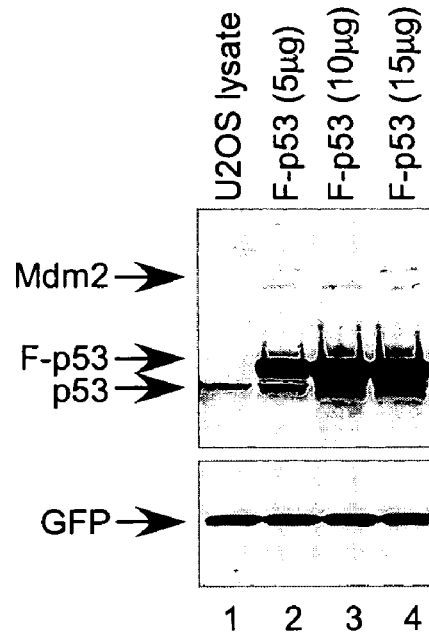
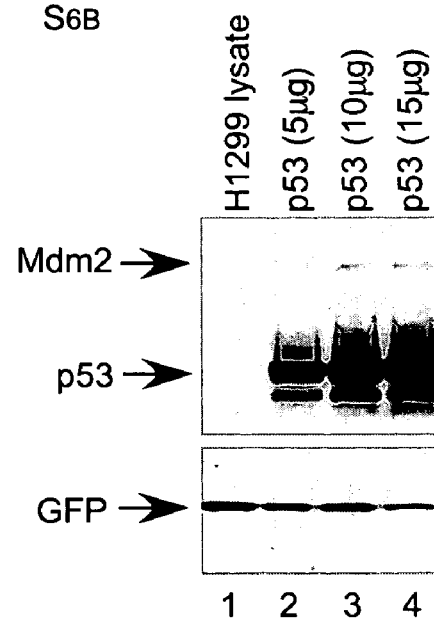
FIG. 16

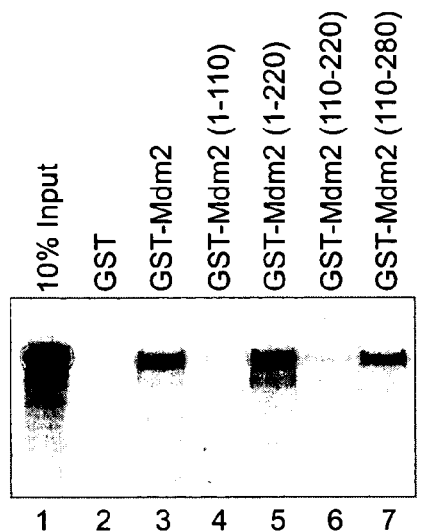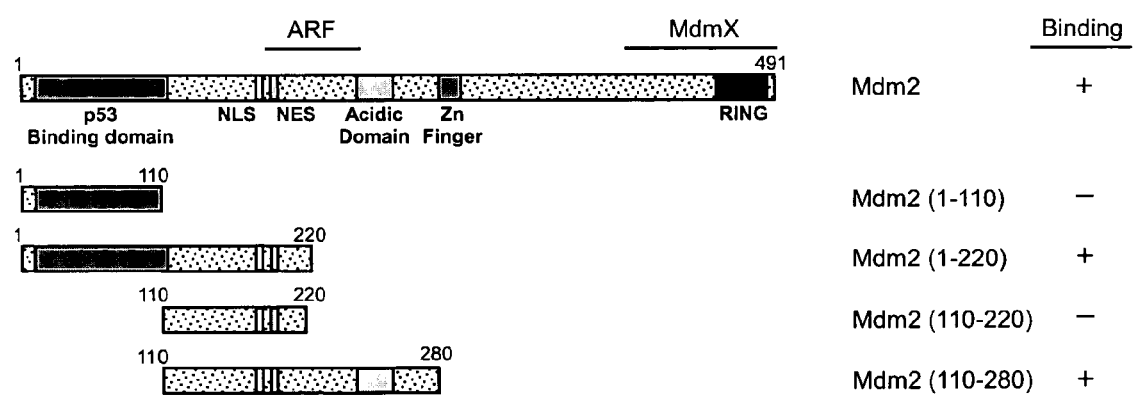
FIG. 17

HAUSP-MDM2 INTERACTION AND USES THEREOF

RELATED APPLICATION

This application is a continuation-in-part of U.S. patent application Ser. No. 10/113,732, filed on Mar. 30, 2002.

STATEMENT OF GOVERNMENT INTEREST

This invention was made with government support under NIH Grant No. RO1-CA85533. As such, the United States government has certain rights in this invention.

BACKGROUND OF THE INVENTION

Neoplasia is a disease characterized by an abnormal cell growth known as a neoplasm. Neoplasms may manifest in the form of a leukemia or a tumor, and may be benign or malignant. Malignant neoplasms, in particular, can result in a serious disease state, which may threaten life. Significant research efforts and resources have been directed toward the elucidation of antineoplastic measures, including chemotherapeutic agents, which are effective in treating patients suffering from neoplasia. Effective antineoplastic agents include those which inhibit or control the rapid proliferation of cells associated with neoplasms, those which effect regression or remission of neoplasms, and those which generally prolong the survival of patients suffering from neoplasia. Successful treatment of malignant neoplasia, or cancer, requires elimination of all malignant cells, whether they are found at the primary site, or have extended to local/regional areas, or have metastasized to other regions of the body. The major therapies for treating neoplasia are surgery and radiotherapy (for local and regional neoplasms) and chemotherapy (for systemic sites) (Beers and Berkow (eds.), *The Merck Manual of Diagnosis and Therapy*, 17$^{th}$ ed. (Whitehouse Station, N.J.: Merck Research Laboratories, 1999) 973-74, 976, 986, 988, 991).

Despite the various methods for detecting, diagnosing, and treating cancers, the disease remains prevalent in all segments of society, and is often fatal. Clearly, alternative strategies for detection (including the development of markers that can identify neoplasias at an early stage) and treatment are needed to improve survival in cancer patients. In particular, a better understanding of tumor suppressors, and tumor-suppression pathways, would provide a basis from which novel detection, diagnostic, and treatment regimens may be developed.

The p53 tumor suppressor exerts anti-proliferative effects, including growth arrest, apoptosis, and cell senescence, in response to various types of stress (Levine, A. J., p53, the cellular gatekeeper for growth and division. *Cell*, 88:323-31, 1997; Giaccia and Kastan, The complexity of p53 modulation: emerging patterns from divergent signals. *Genes Dev.*, 12:2973-83, 1998; Prives and Hall, The p53 pathway. *J. Pathol.*, 187:112-26, 1999; Oren, M., Regulation of the p53 tumor suppressor protein. *J. Biol. Chem.*, 274, 36031-034, 1999; Vogelstein et al., Surfing the p53 network. *Nature*, 408:307-10, 2000; Michael and Oren, The p53-Mdm2 module and the ubiquitin system. *Semin. Cancer Biol.*, 13:49-58, 2003). p53 is the most commonly mutated gene in human cancers, with more than 50% of tumors displaying some alteration in p53 (Hollstein et al., Database of p53 gene somatic mutations in human tumors and cell lines. *Nucleic Acids Res.*, 22:3551-55, 1994; Hollstein et al., New approaches to understanding p53 gene tumor mutation spectra. *Mutat. Res.*, 431:199-209, 1999).

Wild-type p53 has been called the guardian of the genome, as it responds to DNA damage or checkpoint failure by either arresting the cell in the $G_1$ phase for damage repair, or initiating an apoptotic pathway to eliminate the damaged cell entirely (Lane, D. P., *Nature*, 358:15-16, 1992; Levine, A. J., p53, the cellular gatekeeper for growth and division. *Cell*, 88:323-31, 1997). p53 is also critical for maintenance of genomic stability, aberrant ploidy, gene amplification, increased recombination, and centrosomal dysregulation—all of which have been observed in cells lacking functional p53 (Donehower et al., *Nature*, 356:215-21, 1992). These observations suggest that abrogation of p53 function is critical in tumorigenesis of cancer. Additionally, numerous studies indicate that inactivation of the p53 pathway is a pivotal event in tumorigenesis of all kinds of human cancers, including breast cancer (Vogelstein et al., Surfing the p53 network. *Nature*, 408:307-10, 2000). Accumulating evidence further indicates that, in cells that retain wild-type p53, other defects in the p53 pathway play an important role in tumorigenesis (Prives and Hall, The p53 pathway. *J. Pathol.*, 187:112-26, 1999; Oren, M., Regulation of the p53 tumor suppressor protein. *J. Biol. Chem.*, 274, 36031-034, 1999).

p53 is a short-lived protein, the activity of which is maintained at low levels in normal cells. The molecular function of p53 that is required for tumor suppression involves the ability of p53 to act as a transcriptional factor in regulating endogenous gene expression. A number of genes which are critically involved in either cell-growth arrest or apoptosis have been identified as p53 direct targets, including p21$^{CIP1/WAF1}$, Mdm2 (murine double minute 2), GADD45, cyclin G, 14-3-3σ, Noxa, p53AIP1, and PUMA (Kastan et al., A mammalian cell cycle checkpoint pathway utilizing p53 and GADD45 is defective in ataxia-telangiectasia. *Cell*, 71:587-97, 1992; el-Deiry et al., WAF1, a potential mediator of p53 tumor suppression. *Cell*, 75:817-825, 1993; Wu et al., The p53-mdm-2 autoregulatory feedback loop. *Genes Dev.*, 7:1126-32, 1993; Barak et al., mdm2 expression is induced by wild type p53 activity. *EMBO J.*, 12:461-68, 1993; Okamoto and Beach, Cyclin G is a transcriptional target of the p53 tumor suppressor protein. *EMBO J.*, 13:4816-22, 1994; Oda et al., Noxa, a BH3-only member of the Bcl-2 family and candidate mediator of p53-induced apoptosis. *Science*, 288:1053-58, 2000a; Oda et al., p53AIP1, a potential mediator of p53-dependent apoptosis, and its regulation by Ser-46-phosphorylated p53. *Cell*, 102:849-62, 2000b; Nakano and Vousden, PUMA, a novel proapoptotic gene, is induced by p53. *Molecular Cell*, 7:683-94, 2001; Yu et al., PUMA induces the rapid apoptosis of colorectal cancer cells. *Molecular Cell*, 7:673-82, 2001). Furthermore, tight regulation of p53 itself is essential for its effect on tumorigenesis and the maintenance of normal cell growth.

Numerous studies imply the existence of multiple pathways involved in p53 stabilization (Shieh et al., DNA damage-induced phosphorylation of p53 alleviates inhibition MDM2. *Cell*, 91:325-34, 1997; Ashcroft et al., Regulation of p53 function and stability by phosphorylation. *Mol. Cell Biol.*, 19:1751-58, 1999; Blattner et al., DNA damage induced p53 stabilization: no indication for an involvement of p53 phosphorylation. *Oncogene*, 18:1723-32, 1999; Dumaz and Meek, Serine15 phosphorylation stimulates p53 transactivation but does not directly influence interaction with HDM2. *EMBO J.*, 18:7002-10, 1999; Ashcroft et al., Stress signals utilize multiple pathways to stabilize p53. *Mol. Cell Biol.*, 20:3224-33, 2000; Appella and Anderson, Signaling to p53: breaking the posttranslational modification code. *Pathol. Biol. (Paris)*, 48:227-45, 2000). The precise mechanisms by which p53 is activated by such multiple regulatory pathways are not completely understood. Generally, however, they are thought to involve post-translational modifications of p53, including ubiquitination, phosphorylation, and acetylation (Giaccia and Kastan, The complexity of p53 modulation: emerging patterns from divergent signals. *Genes Dev.*, 12:2973-83, 1998; Appella and Anderson, Signaling to p53: breaking the posttranslational modification code. *Pathol. Biol.* (*Paris*), 48:227-45, 2000; Brooks and Gu, Ubiquitination, phosphorylation and acetylation: the molecular basis for p53 regulation. *Curr. Opin. Cell Biol.*, 15:164-71, 2003). In response to DNA damage, for example, p53 is phosphorylated at multiple sites; these phosphorylation events promote p53 stabilization by preventing binding with Mdm2, thereby rendering p53 more resistant to Mdm2-mediated degradation (Shieh et al., DNA damage-induced phosphorylation of p53 alleviates inhibition MDM2. *Cell*, 91:325-34, 1997; Appella and Anderson, Signaling to p53: breaking the posttranslational modification code. *Pathol. Biol.* (*Paris*), 48:227-45, 2000).

By serving as a signal for specific cellular-protein degradation, protein ubiquitination (e.g., mono-ubiquitination, polyubiquitination) plays a critical role in the physiological regulation of many cellular processes (Laney and Hochstrasser, Substrate targeting in the ubiquitin system. *Cell*, 97:427-30, 1999; Kornitzer and Ciechanover, Modes of regulation of ubiquitin-mediated protein degradation. *J. Cell. Phys.*, 182:1-11, 2000; Hershko et al., The ubiquitin system. *Nat. Med.*, 6:1073-81, 2000; Pickart, C. M., Back to the future with ubiquitin. *Cell*, 116:181-90, 2004). While polyubiquitination serves primarily as a signal for proteasome-dependent degradation, the functional consequences of mono-ubiquitination are often linked with protein trafficking and other degradation-independent processes (Hicke and Dunn, Regulation of membrane protein transport by ubiquitin and ubiquitin-binding proteins. *Annu. Rev. Cell Dev. Biol.*, 19:141-72, 2003). Deubiquitination, which removes the ubiquitin moiety from ubiquitin-modified proteins, is also now recognized as an important regulatory step (Wilkinson, K. D., Signal transduction: aspirin, ubiquitin and cancer. *Nature*, 424:738-39, 2003; D'Andrea and Pellman, Deubiquitinating enzymes: a new class of biological regulators. *Crit. Rev. Biochem. Mol. Biol.*, 33:337-52, 1998).

The ubiquitination of p53 was first discovered in papilloma-virus-infected cells, where p53 degradation is mediated by the viral E6 protein (Scheffner et al., The HPV-16 E6 and E6-AP complex functions as an ubiquitin-protein ligase in the ubiquitination of p53. *Cell*, 75:495-505, 1993). In normal cells, regulation of p53 degradation is governed primarily by Mdm2, an oncoprotein that physically interacts with the N-terminus of p53, and thereby counteracts p53's tumor-suppressor activity (Haupt et al., Mdm2 promotes the rapid degradation of p53. *Nature*, 387:296-99, 1997; Kubbutat et al., Regulation of p53 stability by Mdm2. *Nature*, 387:299-303, 1997; Honda et al., Oncoprotein MDM2 is a ubiquitin ligase E3 for tumor suppressor p53. *FEBS Lett.*, 420:25-27, 1997). By acting as a p53-specific E3 ligase, Mdm2 is critical for degradation of p53, and also induces nuclear export of p53 by mono-ubiquitinating p53 (Freedman et al., Functions of the MDM2 oncoprotein. *Cell Mol. Life Sci.*, 55:96-107, 1999).

Interestingly, transcription of the Mdm2 gene is activated by p53; thus, there is an auto-regulatory loop in which increased Mdm2 production limits p53 induction in response to a variety of cell stresses (Ashcroft and Vousden, Regulation of p53 stability. *Oncogene*, 18:7637-43, 1999). The critical role of Mdm2 in p53 regulation is best illustrated by studies carried out in mice, wherein inactivation of p53 was shown to rescue completely the embryonic lethality caused by loss of Mdm2 function (Jones et al., Rescue of embryonic lethality in Mdm2-deficient mice by absence of p53. *Nature*, 378:206-08, 1995; Montes de Oca Luna et al., Rescue of early embryonic lethality in mdm2-deficient mice by deletion of p53. *Nature*, 378:203-06, 1995).

The stabilization of p53 that occurs in response to oncogene signaling is thought to result from induction of p14ARF, a tumor-suppressor protein that can form a complex with Mdm2, thereby stabilizing both p53 and Mdm2 in vivo (Lowe and Sherr, Tumor suppression by Ink4a-Arf: progress and puzzles. *Curr. Opin. Genet. Dev.*, 13:77-83, 2003). The importance of p14ARF in the p53 pathway is underscored by increased tumor susceptibility of p14ARF-deficient mice (Kamijo et al., Tumor suppression at the mouse INK4a locus mediated by the alternative reading frame product p19ARF. *Cell*, 91:649-59, 1997; Sherr, C.J., The INK4a/ARF network in tumour suppression. *Nat. Rev. Mol. Cell Biol.*, 2:731-37, 2001). MdmX, a member of the Mdm2 family, has recently emerged as another key regulator of p53 function. In contrast to Mdm2, MdmX alone cannot ubiquitinate p53; rather, it stabilizes both p53 and Mdm2 (Stad et al., Mdmx stabilizes p53 and Mdm2 via two distinct mechanisms. *EMBO Rep.*, 2:1029-34, 2001). On this basis, it has been proposed that MdmX and Mdm2 have opposite effects on p53 stability. Mdmx-null mice are embryonic lethal, and the lethality can be rescued in a p53-null background—in a manner reminiscent of Mdm2-deficient mice (Parant et al., Rescue of embryonic lethality in Mdm4-null mice by loss of Trp53 suggests a non-overlapping pathway with MDM2 to regulate p53. *Nat. Genet.*, 29:92-95, 2001; Finch et al., Mdmx is a negative regulator of p53 activity in vivo. *Cancer Res.*, 62:3221-225, 2002; Migliorini et al., Mdm4 (Mdmx) regulates p53-induced growth arrest and neuronal cell death during early embryonic mouse development. *Mol. Cell Biol.*, 22:5527-38, 2002). Although the precise function of MdmX needs further elucidation (de Graaf et al., Hdmx protein stability is regulated by the ubiquitin ligase activity of Mdm2. *J. Biol. Chem.*, 278:38315-324, 2003; Kawai et al., DNA damage-induced MDMX degradation is mediated by MDM2. *J. Biol. Chem.*, 278:45946-953, 2003; Pan and Chen, MDM2 promotes ubiquitination and degradation of MDMX. *Mol. Cell Biol.*, 23:5113-21, 2003), these studies suggest a critical role for MdmX in the p53 pathway.

As indicated above, evidence suggests that, in cells that retain wild-type p53, other defects in the p53 pathway may play an important role in tumorigenesis. To date, at least one method of treating cancer, by targeting the p53 pathway, has been developed. This treatment involves the stabilization of p53 by inhibiting Mdm2-mediated deubiquitination. It is estimated that 15-30% of all tumor cases exhibit overexpression of Mdm2. However, this enzyme is notoriously difficult to inhibit. Recent studies also imply the existence of an alternative mechanism for p53 stabilization that may function even when the Mdm2-mediated ubiquitination pathway is intact (Ashcroft et al., Regulation of p53 function and stability by phosphorylation. *Mol. Cell Biol.*, 19:1751-58, 1999; Blattner et al., DNA damage induced p53 stabilization: no indication for an involvement of p53 phosphorylation. *Oncogene*, 18:1723-32, 1999; Dumaz and Meek, Serine15 phosphorylation stimulates p53 transactivation but does not directly influence interaction with HDM2. *EMBO J.*, 18:7002-10, 1999; Ashcroft et al., Stress signals utilize multiple pathways to stabilize p53. *Mol. Cell Biol.*, 20:3224-33, 2000).

On the basis of the foregoing, regulation of the p53 pathway is of intense interest, and presents a potential means of diagnosing and treating cancers. Nevertheless, a greater understanding of this pathway, and the regulation of p53 ubiquitination and deubiquitination, would provide a valuable basis upon which new diagnostic and therapeutic methods could be developed.

SUMMARY OF THE INVENTION

The present invention is based upon the discovery that ubiquitination of p53 is reversible, and that the ubiquitin hydrolase, HAUSP, directly binds to, and deubiquitinates, p53. This deubiquitination has the effect of activating and stabilizing cellular p53, thereby rendering it available for tumor-suppressor activity. This discovery has broad implications in the diagnosis, monitoring, and treatment of neoplasias, particularly cancers associated with p53.

The present invention is further based upon the discovery that partial reduction of endogenous HAUSP levels by RNAi destabilizes p53, while complete ablation of HAUSP stabilizes and activates p53. The inventors have determined that this phenomenon occurs because HAUSP stabilizes Mdm2 in a p53-independent manner, providing a feedback loop in p53 regulation. In normal cells, HAUSP is required for Mdm2 stability; in HAUSP-ablated cells, self-ubiquitinated-Mdm2 becomes extremely unstable, leading to indirect p53 activation. This feedback regulation is specific to Mdm2; in HeLa cells, where p53 is preferentially degraded by viral protein E6-dependent ubiquitination, depletion of HAUSP fails to activate p53. Thus, the inventors have discovered an example of a ubiquitin ligase (Mdm2) that is directly regulated by a deubiquitinase (HAUSP), revealing a dynamic role of HAUSP in the p53-Mdm2 pathway.

Accordingly, the present invention provides a method for determining whether a subject has neoplasia, by assaying a diagnostic sample of the subject for Mdm2 expression and HAUSP expression, wherein detection of Mdm2 expression elevated above normal and HAUSP expression elevated above normal in the diagnostic sample is diagnostic of neoplasia in the subject. In one embodiment, Mdm2 expression elevated above normal and HAUSP expression elevated above normal are detected in the diagnostic sample by detecting Mdm2-HAUSP interaction elevated above normal in the diagnostic sample.

The present invention further provides a method for assessing the efficacy of therapy to treat neoplasia in a subject who has undergone or is undergoing treatment for neoplasia, by assaying a diagnostic sample of the subject for Mdm2 expression and HAUSP expression, wherein detection of normal Mdm2 expression and normal HAUSP expression in the diagnostic sample is indicative of successful therapy to treat neoplasia, and detection of Mdm2 expression elevated above normal and HAUSP expression elevated above normal in the diagnostic sample is indicative of a need to continue therapy to treat neoplasia. In one embodiment, Mdm2 expression elevated above normal and HAUSP expression elevated above normal are detected in the diagnostic sample by detecting Mdm2-HAUSP interaction elevated above normal in the diagnostic sample.

The present invention also provides a method for assessing the prognosis of a subject who has neoplasia, by assaying a diagnostic sample of the subject for Mdm2 expression and HAUSP expression, wherein the subject's prognosis improves with detection of a decrease in Mdm2 expression and a decrease in HAUSP expression in the diagnostic sample, and the subject's prognosis worsens with detection of an increase in Mdm2 expression and an increase in HAUSP expression in the diagnostic sample. In one embodiment, Mdm2 expression and HAUSP expression are detected in the diagnostic sample by detecting Mdm2-HAUSP interaction in the diagnostic sample.

Additionally, the present invention provides a kit for use in detecting neoplasia, comprising: (a) at least one agent reactive with Mdm2; (b) at least one agent reactive with HAUSP; and (c) reagents suitable for detecting expression of Mdm2 and expression of HAUSP.

The present invention further provides a method for treating neoplasia in a subject, by increasing activity of p53 in the subject, wherein activity of p53 is increased in the subject by modulating Mdm2-HAUSP interaction in the subject.

The present invention also provides a method for deubiquitinating and/or stabilizing Mdm2 in a cell, by contacting the cell with HAUSP, in an amount effective to deubiquitinate and/or stabilize Mdm2.

Additionally, the present invention provides a method for modulating deubiquitination and/or stability of p53 in a cell, by contacting the cell with a modulator of Mdm2-HAUSP interaction, in an amount effective to modulate deubiquitination and/or stability of p53.

The present invention further provides a method for identifying a modulator of Mdm2-HAUSP interaction, by: (a) obtaining or generating an in vitro system comprising Mdm2 and HAUSP; (b) contacting the in vitro system with a candidate modulator; and (c) determining if the candidate modulator modulates Mdm2-HAUSP interaction in the in vitro system. In one embodiment, the determination in step (c) is made by comparing Mdm2-HAUSP interaction in the in vitro system of step (b) with Mdm2-HAUSP interaction in a second in vitro system comprising Mdm2, HAUSP, the candidate modulator, and an anti-Mdm2 or anti-HAUSP antibody or antagonist. Also provided is a modulator identified by this method, and a method for treating an Mdm2-, HAUSP-, or p53-associated condition in a subject by administering the modulator to the subject.

The present invention further provides a pharmaceutical composition, comprising an effective amount of a modulator of Mdm2-HAUSP interaction, and a pharmaceutically-acceptable carrier. Also provided is use of a modulator of Mdm2-HAUSP interaction in a method of treating neoplasia.

Additionally, the present invention provides a method for identifying an agent that is reactive with Mdm2, by: (a) contacting a candidate agent with Mdm2, in the presence of HAUSP; and (b) assessing the ability of the candidate agent to inhibit Mdm2-HAUSP interaction. Optionally, the method may further comprise the steps of: (c) contacting the candidate agent with one or more cells comprising Mdm2, HAUSP, or p53; and (d) determining if the agent has an effect on one or more Mdm2-, HAUSP-, or p53-associated biological events in the one or more cells. Also provided is an agent identified by this method.

The present invention further provides a method for identifying an agent that is reactive with HAUSP, by: (a) contacting a candidate agent with HAUSP, in the presence of Mdm2; and (b) assessing the ability of the candidate agent to inhibit HAUSP-Mdm2 interaction. Optionally, the method further comprises the steps of: (c) contacting the candidate agent with one or more cells comprising Mdm2, HAUSP, or p53; and (d) determining if the agent has an effect on one or more Mdm2-, HAUSP-, or p53-associated biological events in the one or more cells. Also provided is an agent identified by this method.

Finally, the present invention provides a complex comprising Mdm2 and HAUSP.

Additional aspects of the present invention will be apparent in view of the description which follows.

BRIEF DESCRIPTION OF THE FIGURES

FIGS. 3A-3B depicts the effects of HAUSP on p53-mediated cell-growth repression (A) and apoptosis (B). (A) A pair of human lung carcinoma cells (H1299 and H460) and a pair of mouse embryo fibroblasts (MEF p53(+/+) and MEF p53 (−/−)) were either infected with pBabe-vector, or with pBabe-HAUSP. At 24 h post-infection, cells were split and kept in the medium with puromycin, and surviving colonies were counted after 2 weeks. (B) H1299 cells were transfected with p53 alone or HAUSP alone, or co-transfected with p53 and Mdm2, or co-transfected with p53, Mdm2, and HAUSP, as indicated. After transfection, the cells were fixed, stained for p53 by FITC-conjugated a-p53 antibody, and analyzed for apoptotic cells (subG1) according to DNA content (PI staining).

FIGS. 4A-4C illustrate deubiquitination of p53 by HAUSP, both in vivo and in vitro. (A) Regulation of p53 ubiquitination levels in vivo. Western-blot analysis of immunoprecipitates with the M2/Flag antibody from the cells transfected with Flag-p53 (lane 1), or co-transfected with Flag-p53 and Mdm2 (lane 2), or in combination with different expression vectors as indicated (lanes 3-5), by the anti-p53 monoclonal antibody, DO-1. (B) Regulation of p53 stability by the HAUSP mutant. Western-blot analysis of H1299 cell extracts from the cells transfected with p53 (lane 1), or co-transfected with p53 and Mdm2 (lane 2), or in combination with different expression vectors as indicated (lanes 3-5), by the anti-p53 monoclonal antibody, DO-1. The CMV-GFP expression vector was included in each transfection for a transfection-efficiency control, and the levels of GFP were detected with the anti-GFP monoclonal antibody, JL-8 (Clontech). (C) In vitro deubiquitination of p53 by HAUSP. The purified ubiquitinated p53 protein was incubated with the purified recombinant proteins of either HAUSP (lane 2) or HAUSP-cs (lane 3).

FIG. 6 sets forth the amino acid sequence of human HAUSP (SEQ ID NO:6).

FIG. 7 sets forth the cDNA sequence of human HAUSP (SEQ ID NO:7).

FIGS. 13A-13C illustrate that HAUSP-mediated feedback regulation of p53 is specific to Mdm2. (A) Western-blot analysis of whole-cell extracts of H1299 cells transfected with Flag-p53 and increasing amounts of E6 without HAUSP (lanes 2 and 3) or with HAUSP (lanes 4 and 5), with anti-p53 (DO-1) antibody. (B) Deubiquitination of p53 by HAUSP in vitro. Purified ubiquitinated Flag-p53 protein (lane 1) from HeLa cells was incubated with purified recombinant proteins of either HAUSP (lane 2) or HAUSP-cs (lane 3). (C) Whole-cell extracts of HeLa cells, treated with either control-RNAi (lane 1) or HAUSP#1-RNAi (lane 2), were immunoblotted with anti-p53 (DO-1), anti-HAUSP, anti-actin (AC-15), and anti-p21 antibodies.

FIG. 14 shows that HAUSP stabilizes both p53 and Mdm2 in U2OS cells (top panel), and that Mdm2 is specifically deubiquitinated by HAUSP, but not UBP11, in vitro (middle and bottom panels). (top panel) A Western-blot analysis of whole-cell extracts from U2OS cells transfected with Flag-p53 alone (lane 1), Flag-p53 and Mdm2 (lane 2), or Flag-p53, Mdm2, and HAUSP (lane 3), with anti-p53 (DO-1), anti-Mdm2, and anti-GFP antibodies. (middle panel) Purified in vitro ubiquitinated Mdm2 protein (lane 1) was incubated with the purified recombinant proteins of either GST-UBP11 (lane 2) or GST-HAUSP (lane 3), and immunoblotted with anti-Mdm2 antibody. (bottom panel) UBP11 is an active deubiquitinase in vitro. Poly-ubiquitin chains (Ub2-7) (Affiniti) were incubated with either GST (lane 2) or GST-UBP11 (lane 1), and immunoblotted with mouse anti-ubiquitin antibody.

FIG. 15 demonstrates that HAUSP is a specific deubiquitinase for Mdm2, but not c-Myc (top panel); that HAUSP depletion has no effect on other unstable proteins, such as c-Myc and p27 (middle panel); and that the mRNA levels of Mdm2 are elevated, but the mRNA levels of p53 are kept even, by HAUSP depletion (bottom panel). (top panel) 293 cells transfected with Flag-Myc and HA-Ub constructs were subjected to anti-Flag (M2) immunopurification. The ubiquitinated Flag-Myc protein was then incubated with recombinant GST-HAUSP protein in vitro. The blot was probed with either anti-HA (lanes 1 and 2) or anti-Myc (C33) (lanes 3 and 4) antibodies. (middle panel) The U2OS-HAUSP shRNA stable line was transiently transfected with three rounds of HAUSP#1-RNAi treatment. The blots were probed with anti-HAUSP, anti-Myc (C33), anti-p53 (DO-1), anti-actin (AC-15), and anti-p27 antibodies. (bottom panel) RT-PCR was performed on either the control-RNAi or HAUSP#1-RNAi stable lines—which had been treated with an additional round of control-RNAi or HAUSP#1-RNAi, respectively—using primers specific for Mdm2, p53, and actin.

FIG. 16 show that overexpression of p53 induces endogenous Mdm2 expression. (top panel) U2OS cells were transfected with 5 μg of Flag-p53 (lane 2), 10 μg of Flag-p53 (lane 3), or 15 μg of Flag-p53 (lane 4). The blot was probed with anti-Mdm2, anti-p53 (DO-1), and anti-GFP antibodies. (bottom panel) H1299 cells were transfected with 5 μg of p53 (lane 2), 10 μg of p53 (lane 3), or 15 μg of p53 (lane 4). The blot was probed with anti-Mdm2, anti-p53 (DO-1), and anti-GFP antibodies.

FIG. 17 illustrates the in vitro interaction between HAUSP and human Mdm2. (top panel) The GST (lane 2) and GST-Mdm2 (lane 3) fusion proteins were used in a GST pull-down assay with in vitro translated $^{35}$S-labeled full-length HAUSP. Further characterization of the Mdm2 interacting domain was conducted using in vitro translated $^{35}$S-labeled full-length HAUSP incubated with the N terminus of GST-Mdm2 (1-110) (lane 4), the extended N terminus of GST-Mdm2 (1-220) (lane 5), GST-Mdm2 (110-220) (lane 6), and GST-Mdm2 (110-280) (lane 7). (bottom panel) Schematic representation of Mdm2 wt protein and fragments used in assays described herein, with protein-binding domains and Mdm2 conserved regions indicated.

DETAILED DESCRIPTION OF THE INVENTION

Figure 1:
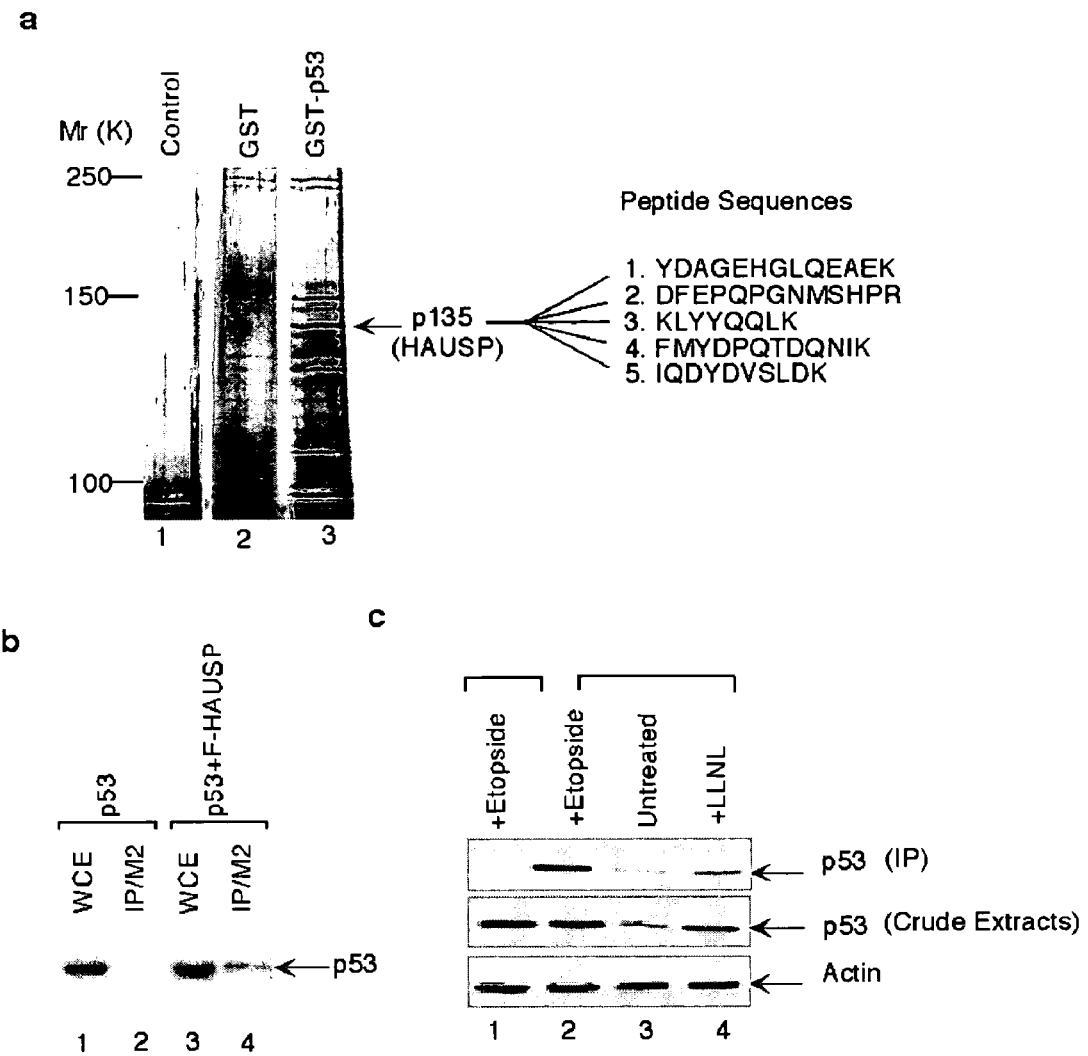
FIGS. 1A-1C illustrate purification of HAUSP, and interactions between p53 and HAUSP. (A) HAUSP was identified as a p53-binding protein, using silver-staining analysis of a SDS-PAGE gel containing the eluates from the indicated columns. The following peptide sequences, derived from the p135 protein band, were obtained from mass spectrometry: YDAGEHGLQEAEK (SEQ ID NO:1); DFEPQPGNMSHPR (SEQ ID NO:2); KLYYQQLK (SEQ ID NO:3); FMYDPQTDQNIK (SEQ ID NO:4); and IQDYDVSLDK (SEQ ID NO:5). (B) Using Western-blot analysis of the whole-cell extract (WCE) or immunoprecipitates (IP/M2) from transfected cells by anti-p53 monoclonal antibody, DO-1, it was determined that p53 interacts with HAUSP in cells. (C) The interaction between the endogenous p53 and HAUSP proteins was elucidated using Western-blot analyses of control immunoprecipitates with the pre-immunoserum (lane 1, upper), or Western-blot analyses of immunoprecipitates with the anti-HAUSP antibody (IP/a-HAUSP) from untreated cells (lane 3, upper) or cells treated with a DNA-damage reagent (Etoposide) (lane 2, upper) or H460 cells treated with a proteasome inhibitor (LLNL) (lane 4, upper), or Western-blot analyses of these different nuclear extracts (NE) immunoprecipitated by the anti-p53 (middle panels) or anti-actin monoclonal antibody (lower panels).
FIGS. 11A-1E show that HAUSP interacts with, and stabilizes, Mdm2 in the absence of p53. (A) The in vitro interaction between HAUSP and Mdm2. The GST (lane 2) and GST-Mdm2 (lane 3) fusion proteins were used in a GST pull-down assay with in vitro translated $^{35}$S-labeled full-length HAUSP. (B) HAUSP interacts with Mdm2 in p53-null cells, as shown in a Western blot of inputs and immunoprecipitates (IP/M2) from control H1299 cells (lane 3) and those stably expressing Flag-Mdm2 wt (lane 4) with anti-HAUSP antibody. (C) Western-blot analysis of control immunoprecipitates with IgG control (lane 2) or immunoprecipitates with the anti-HAUSP antibody (lane 3). (D) Deubiquitination of Mdm2 in vitro by HAUSP. The purified in vitro ubiquitinated Mdm2 protein (lane 2) was incubated with the purified recombinant proteins of either HAUSP (lane 3) or HAUSP-cs (lane 4). (E) Regulation of the half-life of Mdm2 by HAUSP. H1299 cells were transfected with Mdm2, Mdm2 and HAUSP, or Mdm2 and HAUSP-cs. Cells were split 1:4, 24 h post-transfection. At 48 h post-transfection, cells were harvested at different time points, as indicated, after pretreatment with cyclohexamide, and analyzed for Mdm2 and actin protein levels by Western blot using anti-Mdm2 and anti-actin (AC-15) antibodies, respectively.

The p53 tumor suppressor is a short-lived protein that is maintained at low levels in normal cells by Mdm2-mediated ubiquitination and subsequent proteolysis. Stabilization of p53 is critical for its tumor-suppressor function (Ashcroft and Vousden, Regulation of p53 stability. *Oncogene*, 18:7637-43, 1999; Oren, M., Regulation of the p53 tumor suppressor protein. *J. Biol. Chem.*, 274, 36031-034, 1999; Freedman et al., Functions of the MDM2 oncoprotein. *Cell Mol. Life Sci.*, 55:96-107, 1999; Prives and Hall, The p53 pathway. *J. Pathol.*, 187:112-26, 1999; Vogelstein et al., Surfing the p53 network. *Nature*, 408:307-10, 2000). However, the precise mechanism by which ubiquitinated p53 levels are regulated in vivo is not completely understood.

By mass spectrometry of affinity-purified p53-associated factors, the inventors have identified HAUSP (herpesvirus-associated ubiquitin-specific protease) (Everett et al., A novel ubiquitin-specific protease is dynamically associated with the PML nuclear domain and binds to a herpesvirus regulatory protein. *EMBO J.*, 16:566-77, 1997) as a p53-interacting protein. HAUSP strongly stabilizes p53, even in the presence of excess Mdm2 (murine double minute 2), and induces p53-dependent cell-growth repression and apoptosis. Significantly, HAUSP has an intrinsic enzymatic activity that specifically deubiquitinates p53, both in vitro and in vivo. In contrast, expression of a catalytically-inactive HAUSP point mutant in cells increases the levels of p53 ubiquitination, and destabilizes p53. These findings reveal an important mechanism by which p53 can be stabilized by direct deubiquitination, and also implicate HAUSP as a tumor suppressor in vivo, through stabilization of p53.

The inventors' data, as disclosed herein, suggest that HAUSP-mediated stabilization of p53 acts through intrinsic deubiquitinating enzymatic activity. Deubiquitination, which removes the ubiquitin moiety from ubiquitin-modified proteins, is now recognized as an important regulatory step (D'Andrea and Pellman, Deubiquitinating enzymes: a new class of biological regulators. *Crit. Rev. Biochem. Mol. Biol.*, 35:337-52, 1998; Chung and Baek, Deubiquitinating enzymes: their diversity and emerging roles. *Biochem. Biophys. Res. Commun.*, 266:633-40, 1999; Wilkinson, K. D., Ubiquitination and deubiquitination: targeting of proteins for degradation by the proteasome. *Semin. Cell Dev. Biol.*, 11: 141-48, 2000). The large number of ubiquitin-specific processing proteases (UBPs) known to exist also suggests that these proteins may bind to specific cellular proteins, and have substrate specificity. Although a growing number of UBP homologues have been identified in mammalian cells (D'Andrea and Pellman, Deubiquitinating enzymes: a new class of biological regulators. *Crit. Rev. Biochem. Mol. Biol.*, 35:337-52, 1998; Chung and Baek, Deubiquitinating enzymes: their diversity and emerging roles. *Biochem. Biophys. Res. Commun.*, 266:633-40, 1999; Wilkinson, K. D., Ubiquitination and deubiquitination: targeting of proteins for degradation by the proteasome. *Semin. Cell Dev. Biol.*, 11: 141-48, 2000), none has been implicated in stabilizing specific substrates in vivo.

HAUSP may represent the first example of a mammalian protein that can directly deubiquitinate and stabilize a specific cellular factor (p53). Accordingly, the inventors' findings have significant implications regarding the potential tumor-suppression function of HAUSP, and also predict that many UBP-family proteins, like HAUSP, may interact with different substrates in vivo, for both deubiquitination and subsequent protein stabilization.

Previous studies have indicated that HAUSP interacts with the herpesvirus protein, Vmw 110, and that a subset of the HAUSP proteins is localized with the PML nuclear body (Everett et al., A novel ubiquitin-specific protease is dynamically associated with the PML nuclear domain and binds to a herpesvirus regulatory protein. *EMBO J.*, 16:566-77, 1997). In addition, there is now growing evidence showing that ARF is dispensable for p53 activation induced by some types of oncogenic stress (Seavey et al., The E7 oncoprotein of human papillomavirus type 16 stabilizes p53 through a mechanism independent of p19 (ARF). *J. Virol.*, 73:7590-98, 1999; Tolbert et al., p19ARF is dispensable for oncogenic stress-induced p53-mediated apoptosis and tumor suppression in vivo. *Mol. Cell Biol.*, 22:370-77, 2002). Thus, these earlier studies, taken together with the inventors' findings, further suggest potential regulation for the p53-HAUSP interaction in viral infection, DNA damage response, and other types of stress response.

Figure 5:
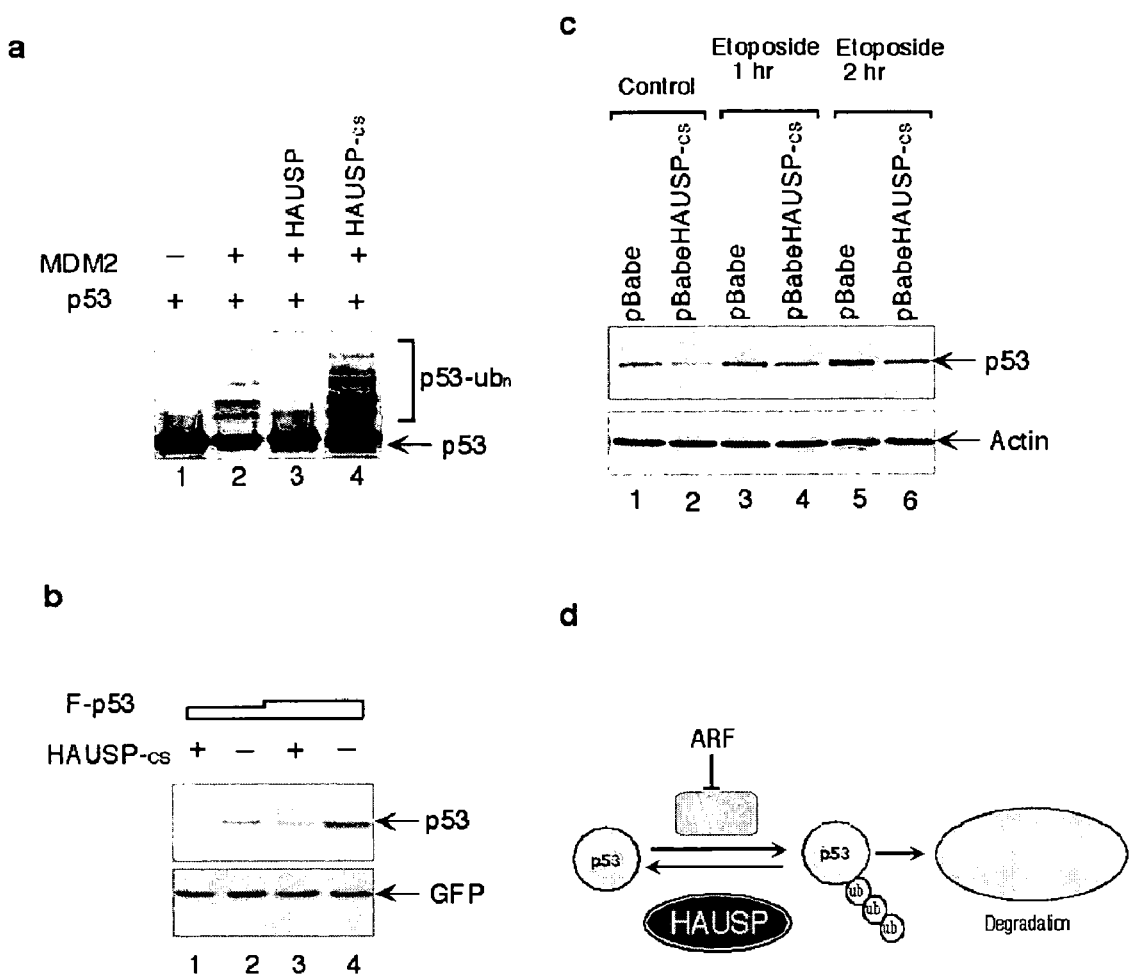
FIGS. 5A-5D demonstrate the dominant negative effects of HAUSP-cs in human cells. (A) Western-blot analysis of immunoprecipitates with the M2/Flag antibody from the cells transfected with Flag-p53 (lane 1), or co-transfected with Flag-p53 and Mdm2 (lane 2), or in combination with HAUSP and HAUSP-cs as indicated (lanes 3, 4), by the anti-p53 monoclonal antibody, DO-1. All cells were treated with LLNL (50 mM) for 4 h before harvest. (B) Western-blot analysis of immunoprecipitates with M2/Flag antibody from human SJSA cells either transfected with expression vectors of Flag-p53 (lanes 2, 4) or co-transfected with expression vectors of Flag-p53 with HAUSP-cs (lanes 1, 3), by the anti-p53 monoclonal antibody, DO-1. The CMV-GFP expression vector was included in each transfection, for a transfection-efficiency control, and the levels of GFP were detected with the anti-GFP monoclonal antibody, JL-8 (Clontech). (C) Western-blot analysis of the cell extracts from both mock-infected and pBabe-HAUSP-cs-infected IMR-90 cells by anti-p53 monoclonal antibody (DO-1). Cells were either not treated (lanes 1,2) or treated with 20 mM of Etoposide (lanes 3-6), for either 1 h or 2 h as indicated. (D) A model for regulation of p53 stability by Mdm2, HAUSP, and ARF. p53 is ubiquitinated by Mdm2, and subsequently degraded by the 26S proteasome, while the ARF tumor suppressor induces p53 stabilization through inhibition of Mdm2-mediated ubiquitin ligase activity. HAUSP can directly deubiquitinate p53, and rescue the ubiquitinated p53 from degradation.

Stabilization of p53 is critical for its effects on cell-growth repression and apoptosis, and for its tumor-suppressor function. Numerous studies have proposed that stabilization of p53 in response to various types of stress may be achieved through inhibition of the Mdm2-p53 interaction and/or Mdm2-mediated ubiquitin ligase (Ashcroft and Vousden, Regulation of p53 stability. *Oncogene*, 18:7637-43, 1999; Freedman et al., Functions of the MDM2 oncoprotein. *Cell Mol. Life Sci.*, 55:96-107, 1999; Oren, M., Regulation of the p53 tumor suppressor protein. *J. Biol. Chem.*, 274, 36031-034, 1999; Prives and Hall, The p53 pathway. *J. Pathol.*, 187:112-26, 1999; Vogelstein et al., Surfing the p53 network. *Nature*, 408:307-10, 2000; Sherr and Webber, The ARF/p53 pathway. *Curr. Opin. Genet. Dev.*, 10:94-99, 2000). The inventors' findings reveal that ubiquitination of p53 is a dynamic process in vivo, and that ubiquitinated p53 can be rescued from degradation by HAUSP through direct deubiquitination (FIG. 5D). It is very likely that changing the balance between Mdm2-mediated ubiquitination of p53 and HAUSP-mediated deubiquitination of p53 is the key for p53 stabilization in vivo.

The inventors' findings, as described herein, also establish a critical role for the HAUSP ubiquitin hydrolase in the control of Mdm2 stability. The inventors have discovered that HAUSP is required for the stability of endogenous Mdm2, which is constitutively self-ubiquitinated and degraded in vivo. In the absence of HAUSP, Mdm2 appears to be extremely unstable, and fails to degrade p53, leading to indirect activation of p53 in HAUSP-depleted cells. This study provides the first example of a deubiquitinase activity (HAUSP) that contributes to the maintenance of stability and function of a ubiquitin ligase (Mdm2). The inventors have also shown that feedback-mediated p53 stabilization is Mdm2-dependent: depletion of endogenous HAUSP fails to induce p53 stabilization in HeLa cells, where p53 degradation is mainly induced by the human papilloma viral protein, E6. Many E3 ubiquitin ligases, including Mdm2, undergo self-ubiquitination as a means of regulating their own stabilities.

The role of HAUSP in the p53 pathway appears to be very unique. On one hand, overexpression of HAUSP stabilizes both p53 and Mdm2, and, more importantly, activates p53 function; these are different from MdmX-mediated effects, but very similar to p14ARF-mediated effects. On the other hand, HAUSP ablation destabilizes Mdm2 and activates p53, generating a phenotype similar to which was observed in Mdm2 knockout cells (Jones et al., Rescue of embryonic lethality in Mdm2-deficient mice by absence of p53. *Nature*, 378:206-08, 1995; Montes de Oca Luna et al., Rescue of early embryonic lethality in mdm2-deficient mice by deletion of p53. *Nature*, 378:203-06, 1995). Given that the net outcome of HAUSP overexpression in normal cells serves to activate p53-dependent transcription and cell-growth repression, p53 may be the preferential target in vivo. This notion is supported by the observation that partial reduction of endogenous HAUSP levels by RNAi induces p53 destabilization.

The surprising ability of HAUSP to modulate the function of both p53 and Mdm2 raises the question of its physiological purpose. Numerous studies have demonstrated the existence of a complicated p53-Mdm2 feedback network, which plays a key role in the regulation of p53 function. In addition to the central feedback loop involving p53 and Mdm2 (Freedman et al., Functions of the MDM2 oncoprotein. *Cell Mol. Life Sci.*, 55:96-107, 1999), regulation of the p53-Mdm2 pathway is also influenced by p14ARF and MdmX, through similar, but distinct, feedback mechanisms. For example, both p53 and Mdm2 can be stabilized by p14ARF (Lowe and Sherr, Tumor suppression by Ink4a-Arf: progress and puzzles. *Curr. Opin. Genet. Dev.*, 13:77-83, 2003), while the levels of p14ARF in cells are down-regulated by p53 expression (Stott et al., The alternative product from the human CDKN2A locus, p14 (ARF), participates in a regulatory feedback loop with p53 and MDM2. *EMBO J.*, 17:5001-14, 1998).

MdmX was initially found to stabilize p53 (Stad et al., Mdmx stabilizes p53 and Mdm2 via two distinct mechanisms. *EMBO Rep.*, 2:1029-34, 2001). Nevertheless, recent studies indicate that MdmX is apparently also involved in p53 degradation (Gu et al., Mutual dependence of MDM2 and MDMX in their functional inactivation of p53. *J. Biol. Chem.*, 277:19251-254, 2002; Linares et al., HdmX stimulates Hdm2-mediated ubiquitination and degradation of p53. *Proc. Natl. Acad. Sci. USA*, 100:12009-014, 2003), and knockout of MdmX in mice leads to p53 activation (Parant et al., Rescue of embryonic lethality in Mdm4-null mice by loss of Trp53 suggests a non-overlapping pathway with MDM2 to regulate p53. *Nat. Genet.*, 29:92-95, 2001; Finch et al., Mdmx is a negative regulator of p53 activity in vivo. *Cancer Res.*, 62:3221-225, 2002; Migliorini et al., Mdm4 (Mdmx) regulates p53-induced growth arrest and neuronal cell death during early embryonic mouse development. *Mol. Cell Biol.*, 22:5527-38, 2002). Furthermore, although Mdm2 can be stabilized by MdmX expression, MdmX is also a substrate of Mdm2, and is degraded by Mdm2-mediated ubiquitination (de Graaf et al., Hdmx protein stability is regulated by the ubiquitin ligase activity of Mdm2. *J. Biol. Chem.*, 278:38315-324, 2003; Kawai et al., DNA damage-induced MDMX degradation is mediated by MDM2. *J. Biol. Chem.*, 278:45946-953, 2003; Pan and Chen, MDM2 promotes ubiquitination and degradation of MDMX. *Mol. Cell Biol.*, 23:5113-21, 2003). The multi-dimensional cross-talk among p53, p14ARF, Mdm2, and MdmX provides an elegant feedback network in which p53 can be activated by multiple pathways, but also kept under a tight control, in vivo. The HAUSP-mediated function described herein clearly adds an interesting layer of feedback regulation to the p53-Mdm2 network.

Since p53 and Mdm2 functionally antagonize each other, the regulation of HAUSP, in stabilizing either p53 or Mdm2 in vivo, becomes extremely important. The inventors have shown that the p53-HAUSP interaction is enhanced in response to DNA damage, correlating well with p53 stabilization in vivo. HAUSP was initially identified as a herpesviral ubiquitin ligase ICP0-associated cellular factor (Everett et al., A novel ubiquitin-specific protease is dynamically associated with the PML nuclear domain and binds to a herpesvirus regulatory protein. *EMBO J.*, 16:1519-30, 1997). More recently, it was reported that Epstein-Barr virus (EBV) nuclear antigen-1 (EBNA-1) can also interact with HAUSP, and may compete with p53 for binding to HAUSP in cells (Holowaty et al., Protein interaction domains of the ubiquitin-specific protease, USP7/HAUSP. *J. Biol. Chem.*, 278:47753-761, 2003; Holowaty et al., Protein profiling with Epstein-Barr nuclear antigen-1 reveals an interaction with the herpesvirus-associated ubiquitin-specific protease HAUSP/USP7. *J. Biol. Chem.*, 278:29987-994, 2003). The inventors' study suggests that reversible ubiquitination is a general mechanism for functional regulation of cellular factors, including ubiquitin ligases themselves. It is possible that, in tumor cells, specific HAUSP mutants may abrogate only the p53-HAUSP interaction, and not the Mdm2-HAUSP interaction. Moreover, the interactions among p53, HAUSP, and Mdm2 may be dynamically regulated upon DNA damage or viral infection.

In view of the foregoing, the present invention provides a method for determining whether a subject has neoplasia. As used herein, the "subject" is a mammal, including, without limitation, a cow, dog, human, monkey, mouse, pig, or rat. Preferably, the subject is a human. The inventors have demonstrated herein (see, e.g., FIGS. 8A-8C) the detection of significant enhancement of HAUSP-p53 interaction, and enhanced HAUSP expression, in cells subjected to DNA damage, as compared with normal (undamaged) cells. Accordingly, the method of the present invention comprises assaying a diagnostic sample of the subject for expression of HAUSP, wherein detection of HAUSP expression elevated above normal is diagnostic of neoplasia in the subject.

As used herein, "HAUSP" includes both a HAUSP (herpesvirus-associated ubiquitin-specific protease) protein and a HAUSP analogue. Unless otherwise indicated, "protein" shall include a protein, protein domain, polypeptide, or peptide. As further used herein, the HAUSP protein (also known as USP7) has the amino acid sequence set forth in FIG. 6 (SEQ ID NO:6; see, also, Everett et al., A novel ubiquitin-specific protease is dynamically associated with the PML nuclear domain and binds to a herpesvirus regulatory protein. *EMBO J.*, 16:566-77, 1997; and GenBank Accession No. CAA96580), including conservative substitutions thereof).

A "HAUSP analogue", as used herein, is a functional variant of the HAUSP protein, having HAUSP biological activity, that has 60% or greater (preferably, 70% or greater) amino-acid-sequence homology with the HAUSP protein. A HAUSP "analogue" includes a variant of the HAUSP protein that has an homologous three-dimensional conformation. As further used herein, the term "HAUSP biological activity" refers to the activity of a protein or peptide that demonstrates an ability to associate physically with p53 tumor-suppressor protein (i.e., binding of approximately two fold, or, more preferably, approximately five fold, above the background binding of a negative control), as described herein, although affinity may be different from that of HAUSP. HAUSP and HAUSP analogues may be produced synthetically or recombinantly, or may be isolated from native cells. HAUSP is preferably produced recombinantly, using conventional techniques and cDNA encoding HAUSP (SEQ ID NO:7; see, also, Everett et al., A novel ubiquitin-specific protease is dynamically associated with the PML nuclear domain and binds to a herpesvirus regulatory protein. *EMBO J.*, 16:566-77, 1997; and GenBank Accession No. Z72499).

As used herein, "conservative substitutions" are those amino acid substitutions which are functionally equivalent to the substituted amino acid residue, either because they have similar polarity or steric arrangement, or because they belong to the same class as the substituted residue (e.g., hydrophobic, acidic, or basic). The term "conservative substitutions", as defined herein, includes substitutions having an inconsequential effect on the ability of HAUSP to interact with p53, particularly in respect of the use of said interaction for the identification and design of p53 inhibitors, for molecular replacement analyses, and/or for homology modeling.

The method of the present invention may be used to determine whether a subject has neoplasia, thereby permitting the diagnosis of such neoplasia in the subject. As used herein, "neoplasia" refers to the uncontrolled and progressive multiplication of cells of a neoplasm (i.e., neoplastic cells, such as tumor cells), under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of neoplastic cells having the unique trait of loss of normal controls, resulting in unregulated growth, lack of differentiation, local tissue invasion, and/or metastasis.

As used herein, neoplasms include, without limitation, morphological irregularities in cells in tissue of a subject, as well as pathologic proliferation of cells in tissue of a subject, as compared with normal proliferation in the same type of tissue. Additionally, neoplasms include benign tumors and malignant tumors (e.g., breast tumors) that are either invasive or noninvasive. Malignant neoplasms are distinguished from benign in that the former show a greater degree of anaplasia, or loss of differentiation and orientation of cells, and have the properties of invasion and metastasis. Examples of neoplasms or neoplasias which may be assessed, detected, diagnosed, monitored, or treated in accordance with inventions described herein include, without limitation, carcinomas, particularly those of the bladder, breast, cervix, colon, head, kidney, lung, neck, ovary, prostate, and stomach; lymphocytic leukemias, particularly acute lymphoblastic leukemia and chronic lymphocytic leukemia; myeloid leukemias, particularly acute monocytic leukemia, acute promyelocytic leukemia, and chronic myelocytic leukemia; malignant lymphomas, particularly Burkitt's lymphoma and Non-Hodgkin's lymphoma; malignant melanomas; myeloproliferative diseases; sarcomas, particularly Ewing's sarcoma, hemangiosarcoma, Kaposi's sarcoma, liposarcoma, peripheral neuroepithelioma, and synovial sarcoma; and mixed types of neoplasias, particularly carcinosarcoma and Hodgkin's disease (Beers and Berkow (eds.), *The Merck Manual of Diagnosis and Therapy*, 17$^{th}$ ed. (Whitehouse Station, N.J.: Merck Research Laboratories, 1999) 973-74, 976, 986, 988, 991).

As indicated above, over 60% of all cancer cases are associated with p53 mutations. Accordingly, in one embodiment of the present invention, the methods and compositions of the present invention are directed to the assessment, detection, diagnosis, monitoring, and treatment of p53-associated neoplasias, including neoplasias associated with a defect in the p53 pathway. In another embodiment of the present invention, the methods and compositions of the present invention are directed to the assessment, detection, diagnosis, monitoring, and treatment of breast cancer, colon cancer, leukemia, lung cancer, malignant melanoma, ovarian cancer, or prostate cancer.

According to the method of the present invention, the diagnostic sample of a subject may be assayed in vitro or in vivo. Where the assay is performed in vitro, a diagnostic sample from the subject may be removed using standard procedures. The diagnostic sample may be tissue, including any bone, brain tissue, breast tissue, colon tissue, muscle tissue, nervous tissue, ovarian tissue, prostate tissue, retinal tissue, skin tissue, or soft tissue, which may be removed by standard biopsy. In addition, the diagnostic sample may be a bodily fluid, including cerebrospinal fluid, pericardial fluid, peritoneal fluid, saliva, serum, and urine. Furthermore, the diagnostic sample taken from the subject or patient may be, for example, any tissue known to have a neoplasm, any tissue suspected of having a neoplasm, or any tissue believed not to have a neoplasm.

Protein may be isolated and purified from the diagnostic sample of the present invention using standard methods known in the art, including, without limitation, extraction from a tissue (e.g., with a detergent that solubilizes the protein) where necessary, followed by affinity purification on a column, chromatography (e.g., FTLC and HPLC), immunoprecipitation (e.g., with an antibody to HAUSP), and precipitation (e.g., with isopropanol and a reagent such as Trizol). Isolation and purification of the protein may be followed by electrophoresis (e.g., on an SDS-polyacrylamide gel). Nucleic acid may be isolated from a diagnostic sample using standard techniques known to one of skill in the art.

In accordance with the method of the present invention, neoplasia in a subject may be diagnosed by assaying a diagnostic sample of the subject for expression of HAUSP, wherein expression of HAUSP elevated above normal is diagnostic of neoplasia. As used herein, "expression" means the transcription of a gene into at least one mRNA transcript, or the translation of at least one mRNA into a protein. For example, "expression of HAUSP" means the transcription of the HAUSP gene into at least one mRNA transcript, or the translation of at least one mRNA into a HAUSP protein, as defined above. Accordingly, a diagnostic sample may be assayed for HAUSP expression by assaying for HAUSP protein, HAUSP cDNA, or HAUSP mRNA. The appropriate form of HAUSP will be apparent based on the particular techniques discussed herein.

Furthermore, it is contemplated that the diagnostic sample may be assayed for expression of any or all forms of HAUSP protein (including precursor, endoproteolytically-processed forms, and other forms resulting from post-translational modification) in order to determine whether a subject or patient has neoplasia. It is also contemplated that the diagnostic sample may be assayed for expression of HAUSP elevated above normal by detecting an increase in p53-HAUSP interaction, as disclosed herein. Accordingly, in one embodiment of the present invention, HAUSP expression elevated above normal is detected by detecting p53-HAUSP interaction elevated above normal.

As used herein, the term "elevated above normal" refers to detection (e.g., of expression of HAUSP, of p53-HAUSP interaction, etc.) at a level that is significantly greater than the level expected for the same type of diagnostic sample taken from a nondiseased subject or patient (i.e., one who does not have neoplasia) of the same gender and of similar age. As further used herein, "significantly greater" means that the difference between the level (e.g., of expression of HAUSP, of p53-HAUSP interaction, etc.) that is elevated above normal, and the expected (normal) level (e.g., of expression of HAUSP, of p53-HAUSP interaction, etc.), is of statistical significance.

Preferably, HAUSP expression (or p53-HAUSP interaction) elevated above normal is expression of HAUSP (or p53-HAUSP interaction) at a level that is at least 10% greater than the level of HAUSP expression (or p53-HAUSP interaction) otherwise expected. Where HAUSP expression (or p53-HAUSP interaction) is expected to be absent from a particular diagnostic sample taken from a particular subject or patient, the normal level of HAUSP expression (or p53-HAUSP interaction) for that subject or patient is nil. Where a particular diagnostic sample taken from a particular subject or patient is expected to have a low level of constitutive HAUSP expression (or p53-HAUSP interaction), that low level is the normal level of HAUSP expression (or p53-HAUSP interaction) for that subject or patient. As disclosed herein, HAUSP-p53 interactions, and HAUSP expression, are generally present at low levels in cells that do not contain DNA damage.

Expected or normal levels of HAUSP expression for a particular diagnostic sample taken from a subject or patient may be easily determined by assaying nondiseased subjects of a similar age and of the same gender. For example, diagnostic samples may be obtained from at least 30 normal, healthy men between the ages of 25 and 80, to determine the normal quantity of HAUSP expression in males. A similar procedure may be followed to determine the normal quantity of HAUSP expression in females. Once the necessary or desired samples have been obtained, the normal quantities of HAUSP expression in men and women may be determined using a standard assay for quantification, such as flow cytometry, Western-blot analysis, or an ELISA for measuring protein quantities, as described below. For example, an ELISA may be run on each sample in duplicate, and the means and standard deviations of the quantity of the HAUSP protein may be determined. If necessary, additional subjects may be recruited before the normal quantities of HAUSP expression are quantified. A similar type of procedure may be used to determine expected or normal levels of p53-HAUSP interaction for a particular diagnostic sample taken from a subject or patient.

In accordance with the method of the present invention, a diagnostic sample of a subject may be assayed for HAUSP expression (or p53-HAUSP interaction), and HAUSP expression (or p53-HAUSP interaction) may be detected in a diagnostic sample, using assays and detection methods readily determined from the known art (e.g., immunological techniques, hybridization analysis, fluorescence imaging techniques, and/or radiation detection, etc.), as well as any assays and detection methods disclosed herein (e.g., immunoprecipitation, Western-blot analysis, etc.). For example, a diagnostic sample of a subject may be assayed for HAUSP expression using an agent reactive with HAUSP. As used herein, "reactive" means the agent has affinity for, binds to, or is directed against a target of interest (e.g., HAUSP). As further used herein, an "agent" shall include a protein, polypeptide, peptide, nucleic acid (including DNA or RNA), antibody, Fab fragment, F(ab')$_2$ fragment, molecule, compound, antibiotic, drug, and any combinations thereof. A Fab fragment is a univalent antigen-binding fragment of an antibody, which is produced by papain digestion. A F(ab')$_2$ fragment is a divalent antigen-binding fragment of an antibody, which is produced by pepsin digestion. Preferably, the agent of the present invention is labeled with a detectable marker or label.

In one embodiment of the present invention, the agent reactive with HAUSP is an antibody. As used herein, the antibody of the present invention may be polyclonal or monoclonal. In addition, the antibody of the present invention may be produced by techniques well known to those skilled in the art. Polyclonal antibody, for example, may be produced by immunizing a mouse, rabbit, or rat with purified protein (e.g., HAUSP). Monoclonal antibody then may be produced by removing the spleen from the immunized mouse, and fusing the spleen cells with myeloma cells to form a hybridoma which, when grown in culture, will produce a monoclonal antibody.

The antibodies used herein may be labeled with a detectable marker or label. Labeling of an antibody may be accomplished using one of a variety of labeling techniques, including peroxidase, chemiluminescent labels known in the art, and radioactive labels known in the art. The detectable marker or label of the present invention may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker or label may be a radioactive marker, including, for example, a radioisotope. The radioisotope may be any isotope that emits detectable radiation, such as $^{35}S$, $^{32}P$, $^{125}I$, $^{3}H$, or $^{14}C$. Radioactivity emitted by the radioisotope can be detected by techniques well known in the art. For example, gamma emission from the radioisotope may be detected using gamma imaging techniques, particularly scintigraphic imaging. Preferably, the agent of the present invention is a high-affinity antibody (e.g., α-HAUSP) labeled with a detectable marker or label.

Where the agent of the present invention is an antibody reactive with HAUSP, a diagnostic sample taken from the subject may be purified by passage through an affinity column which contains HAUSP antibody (e.g., α-HAUSP) as a ligand attached to a solid support, such as an insoluble organic polymer in the form of a bead, gel, or plate. The antibody attached to the solid support may be used in the form of a column. Examples of suitable solid supports include, without limitation, agarose, cellulose, dextran, polyacrylamide, polystyrene, sepharose, or other insoluble organic polymers. The HAUSP antibody (e.g., α-HAUSP) may be further attached to the solid support through a spacer molecule, if desired. Appropriate binding conditions (e.g., temperature, pH, and salt concentration) for ensuring binding of the agent and the antibody may be readily determined by the skilled artisan. In a preferred embodiment, the HAUSP antibody (e.g., α-HAUSP) is attached to a sepharose column, such as Sepharose 4B.

Where the agent is an antibody, a diagnostic sample of the subject may be assayed for HAUSP expression using binding studies that utilize one or more antibodies immunoreactive with HAUSP, along with standard immunological detection techniques. For example, the HAUSP protein eluted from the affinity column may be subjected to an ELISA assay, Western-blot analysis, flow cytometry, or any other immunostaining method employing an antigen-antibody interaction. Preferably, the diagnostic sample is assayed for HAUSP expression using Western blotting.

Alternatively, a diagnostic sample of a subject may be assayed for HAUSP expression using hybridization analysis of nucleic acid extracted from the diagnostic sample taken from the subject. According to this method of the present invention, the hybridization analysis may be conducted using Northern-blot analysis of mRNA. This method also may be conducted by performing a Southern-blot analysis of DNA using one or more nucleic acid probes, which hybridize to nucleic acid encoding HAUSP. The nucleic acid probes may be prepared by a variety of techniques known to those skilled in the art, including, without limitation, the following: restriction enzyme digestion of HAUSP nucleic acid; and automated synthesis of oligonucleotides having sequences which correspond to selected portions of the nucleotide sequence of the HAUSP nucleic acid, using commercially-available oligonucleotide synthesizers, such as the Applied Biosystems Model 392 DNA/RNA synthesizer.

The nucleic acid probes used in the present invention may be DNA or RNA, and may vary in length from about 8 nucleotides to the entire length of the protein-encoding (e.g., HAUSP-encoding) nucleic acid. The nucleic acid used in the probes may be derived from any mammal, including a human. The nucleotide sequence for human HAUSP is known (see, e.g., Everett et al., A novel ubiquitin-specific protease is dynamically associated with the PML nuclear domain and binds to a herpesvirus regulatory protein. *EMBO J.,* 16:566-77, 1997). Using this sequence as a probe, for example, the skilled artisan could readily clone corresponding HAUSP cDNA from other species. In addition, the nucleic acid probes of the present invention may be labeled with one or more detectable markers or labels. Labeling of the nucleic acid probes may be accomplished using one of a number of methods known in the art—e.g., nick translation, end labeling, fill-in end labeling, polynucleotide kinase exchange reaction, random priming, or SP6 polymerase (for riboprobe preparation)—along with one of a variety of labels—e.g., radioactive labels, such as $^{35}$S, $^{32}$P, or $^{3}$H, or nonradioactive labels, such as biotin, fluorescein (FITC), acridine, cholesterol, or carboxy-X-rhodamine (ROX). Combinations of two or more nucleic acid probes (or primers), corresponding to different or overlapping regions of the HAUSP nucleic acid, also may be used to assay a diagnostic sample for HAUSP expression, using, for example, PCR or RT-PCR.

The detection of HAUSP expression (or p53-HAUSP interaction) in the method of the present invention may be followed by an assay to measure or quantify the extent of HAUSP expression in a diagnostic sample of a subject. Such assays are well known to one of skill in the art, and may include immunohistochemistry/immunocytochemistry, flow cytometry, mass spectroscopy, Western-blot analysis, or an ELISA for measuring amounts of HAUSP protein. For example, to use an immunohistochemistry assay, histological (paraffin-embedded) sections of tissue may be placed on slides, and then incubated with an antibody against HAUSP. The slides then may be incubated with a second antibody (against the primary antibody), which is tagged to a dye or other colorimetric system (e.g., a fluorochrome, a radioactive agent, or an agent having high electron-scanning capacity), to permit visualization of HAUSP that is present in the sections.

It is contemplated that the diagnostic sample in the present invention frequently will be assayed for HAUSP expression (or p53-HAUSP interaction) not by the subject or patient, nor by his/her consulting physician, but by a laboratory technician or other clinician. Accordingly, the method of the present invention further comprises providing to a subject's or patient's consulting physician a report of the results obtained upon assaying a diagnostic sample of the subject or patient for HAUSP expression.

Similarly, the present invention provides a method for determining whether a subject has neoplasia, by assaying a diagnostic sample of the subject for Mdm2 expression and HAUSP expression, wherein detection of Mdm2 (murine double minute 2) expression elevated above normal and HAUSP expression elevated above normal in the diagnostic sample is diagnostic of neoplasia in the subject. As discussed above, cancer has been associated with defects in the p53 pathway, including defects in HAUSP, Mdm2, and/or p53. Accordingly, in one embodiment, the methods and compositions of the present invention are directed to the assessment, detection, diagnosis, monitoring, and treatment of p53-associated neoplasias. In another embodiment, the methods and compositions of the present invention are directed to the assessment, detection, diagnosis, monitoring, and treatment of Mdm2- or HAUSP-associated neoplasias.

In accordance with the method of the present invention, a diagnostic sample may be assayed for HAUSP expression by assaying for HAUSP protein, HAUSP cDNA, or HAUSP mRNA, as described above. Additionally, a diagnostic sample may be assayed for Mdm2 expression by assaying for Mdm2 protein, Mdm2 cDNA, or Mdm2 mRNA. The appropriate form of Mdm2 will be apparent based on the particular techniques discussed herein. Expected or normal levels of HAUSP expression for a particular diagnostic sample taken from a subject or patient may be determined in accordance with methods described above. Expected or normal levels of Mdm2 expression for a particular diagnostic sample taken from a subject or patient may be easily determined by assaying nondiseased subjects of a similar age and of the same gender, as described above in connection with HAUSP.

Preferably, Mdm2 expression (or HAUSP expression, or Mdm2-HAUSP interaction) elevated above normal is Mdm2 expression (or HAUSP expression, or Mdm2-HAUSP interaction) at a level that is at least 10% greater than the level of Mdm2 expression (or HAUSP expression, or Mdm2-HAUSP interaction) otherwise expected. Where Mdm2 expression (or HAUSP expression, or Mdm2-HAUSP interaction) is expected to be absent from a particular diagnostic sample taken from a particular subject or patient, the normal level of Mdm2 expression (or HAUSP expression, or Mdm2-HAUSP interaction) for that subject or patient is nil. Where a particular diagnostic sample taken from a particular subject or patient is expected to have a low level of constitutive Mdm2 expression (or HAUSP expression, or Mdm2-HAUSP interaction), that low level is the normal level of Mdm2 expression (or HAUSP expression, or Mdm2-HAUSP interaction) for that subject or patient.

It is contemplated that the diagnostic sample may be assayed for expression of any or all forms of Mdm2 and HAUSP proteins (including precursor, endoproteolytically-processed forms, and other forms resulting from post-translational modification) in order to determine whether a subject or patient has neoplasia. It is also contemplated that the diagnostic sample may be assayed for expression of Mdm2 elevated above normal and expression of HAUSP elevated above normal by detecting an increase in Mdm2-HAUSP interaction. Accordingly, in one embodiment of the present invention, expression of Mdm2 elevated above normal and expression of HAUSP elevated above normal are detected in the diagnostic sample by detecting Mdm2-HAUSP interaction elevated above normal in the diagnostic sample.

A diagnostic sample of a subject may be assayed for Mdm2 expression, HAUSP expression, and/or Mdm2-HAUSP interaction in accordance with methods described herein. Mdm2 expression, HAUSP expression, and/or Mdm2-HAUSP interaction may also be detected in a diagnostic sample using assays and detection methods readily determined from the known art, as well as any assays and detection methods disclosed herein.

For example, a diagnostic sample of a subject may be assayed for Mdm2 expression using hybridization analysis of nucleic acid extracted from the diagnostic sample taken from the subject. This method preferably utilizes a nucleic acid probe which hybridizes to nucleic acid encoding Mdm2. In one embodiment, the nucleic acid probe is labeled with a detectable marker or label. In the alternative, a diagnostic sample of a subject may be assayed for Mdm2 expression using an agent reactive with Mdm2. Preferably, the agent of the present invention is labeled with a detectable marker or label. In one embodiment of the present invention, the agent reactive with Mdm2 is an antibody (e.g., anti-Mdm2 monoclonal antibody, 4b2).

When the agent of the present invention is an antibody reactive with Mdm2, a diagnostic sample taken from the subject may be purified by passage through an affinity column which contains anti-Mdm2 antibody as a ligand attached to a solid support, such as an insoluble organic polymer in the form of a bead, gel, or plate, in accordance with techniques described above for detecting HAUSP. Additionally, where the agent is an anti-Mdm2 antibody, a diagnostic sample of the subject may be assayed for Mdm2 expression using binding studies that utilize one or more antibodies immunoreactive with Mdm2, along with standard immunological detection techniques, as described above in connection with HAUSP.

The detection of Mdm2 expression, HAUSP expression, and/or Mdm2-HAUSP interaction in the method of the present invention may be followed by an assay to measure or quantify the extent of Mdm2 expression, HAUSP expression, and/or Mdm2-HAUSP interaction in the diagnostic sample of a subject. Additionally, the method of the present invention may further comprise the step of to a subject's or patient's consulting physician a report of the results obtained upon assaying a diagnostic sample of the subject or patient for Mdm2 expression, HAUSP expression, and/or Mdm2-HAUSP interaction.

The present invention further provides a method for assessing the efficacy of therapy to treat neoplasia in a subject or patient who has undergone or is undergoing treatment for neoplasia. The method of the present invention comprises assaying a diagnostic sample of the subject or patient for HAUSP expression, wherein detection of a normal level of HAUSP expression is indicative of successful therapy to treat neoplasia, and detection of HAUSP expression elevated above normal is indicative of a need to continue therapy to treat neoplasia. In one embodiment of the present invention, HAUSP expression elevated above normal is detected by detecting p53-HAUSP interaction elevated above normal. The neoplasia may be any of those described above, including p53-associated neoplasias. The diagnostic sample may be a tissue or a bodily fluid, as described above, and may be assayed for expression of HAUSP (or p53-HAUSP interaction) in vitro or in vivo. In addition, the diagnostic sample may be assayed for expression of HAUSP (or p53-HAUSP interaction) using all of the various assays and methods of detection and quantification described above. This method of the present invention provides a means for monitoring the effectiveness of therapy to treat neoplasia by permitting the periodic assessment of levels of HAUSP expression (or p53-HAUSP interaction) in a diagnostic sample taken from a subject or patient.

According to the method of the present invention, a diagnostic sample of a subject or patient may be assayed, and levels of HAUSP expression (or p53-HAUSP interaction) may be assessed, at any time following the initiation of therapy to treat neoplasia. For example, levels of HAUSP expression (or p53-HAUSP interaction) may be assessed while the subject or patient is still undergoing treatment for neoplasia. Where levels of HAUSP expression (or p53-HAUSP interaction) detected in an assayed diagnostic sample of the subject or patient continue to remain elevated above normal, a physician may choose to continue with the subject's or patient's treatment for the neoplasia. Where levels of HAUSP expression (or p53-HAUSP interaction) in an assayed diagnostic sample of the subject or patient decrease through successive assessments, it may be an indication that the treatment for neoplasia is working, and that treatment doses could be decreased or even ceased. Where levels of HAUSP expression (or p53-HAUSP interaction) in an assayed diagnostic sample of the subject or patient do not rapidly decrease through successive assessments, it may be an indication that the treatment for neoplasia is not working, and that treatment doses could be increased. Where HAUSP expression (or p53-HAUSP interaction) is no longer detected in an assayed diagnostic sample of a subject or patient at levels elevated above normal, a physician may conclude that the treatment for neoplasia has been successful, and that such treatment may cease.

It is within the confines of the present invention to assess levels of HAUSP expression following completion of a subject's or patient's treatment for neoplasia, in order to determine whether the neoplasia has recurred in the subject or patient. Accordingly, an assessment of levels of HAUSP expression (or p53-HAUSP interaction) in an assayed diagnostic sample may provide a convenient way to conduct follow-ups of patients who have been diagnosed with neoplasias. Furthermore, it is within the confines of the present invention to use assessed levels of HAUSP expression (or p53-HAUSP interaction) in an assayed diagnostic sample as a clinical or pathologic staging tool, as a means of determining the extent of neoplasia in the subject or patient, and as a means of ascertaining appropriate treatment options.

The present invention also provides a method for assessing the efficacy of therapy to treat neoplasia in a subject who has undergone or is undergoing treatment for neoplasia, by assaying a diagnostic sample of the subject for Mdm2 expression and HAUSP expression, wherein detection of normal Mdm2 expression and normal HAUSP expression in the diagnostic sample is indicative of successful therapy to treat neoplasia, and detection of Mdm2 expression elevated above normal and HAUSP expression elevated above normal in the diagnostic sample is indicative of a need to continue therapy to treat neoplasia. In one embodiment of the present invention, Mdm2 expression elevated above normal and HAUSP expression elevated above normal are detected in the diagnostic sample by detecting Mdm2-HAUSP interaction elevated above normal in the diagnostic sample. The neoplasia may be any of those described above, including p53-associated neoplasias. Suitable diagnostic samples, assays, and detection and quantification methods for use in the method of the present invention have already been described.

A correlation exists, in general, between tumor burden and the survival of a patient who has cancer. Therefore, it is also contemplated in the present invention that assaying a diagnostic sample of a subject for HAUSP expression may be a useful means of providing information concerning the prognosis of a subject or patient who has neoplasia. Accordingly, the present invention further provides a method for assessing the prognosis of a subject who has neoplasia, comprising assaying a diagnostic sample of the subject for HAUSP expression, wherein the subject's prognosis improves with a decrease in HAUSP expression in the diagnostic sample of the subject, and the subject's prognosis worsens with an increase in HAUSP expression in the diagnostic sample of the subject. In one embodiment of the present invention, HAUSP expression elevated above normal is detected by detecting p53-HAUSP interaction elevated above normal. Suitable diagnostic samples, assays, and detection and quantification methods for use in the method of the present invention have already been described. This method of the present invention provides a means for determining the prognosis of a subject or patient diagnosed with neoplasia based upon the level of HAUSP expression (or p53-HAUSP interaction) in an assayed diagnostic sample of the subject or patient.

According to the method of the present invention, a diagnostic sample of a subject or patient may be assayed, and levels of HAUSP expression (or p53-HAUSP interaction) may be assessed, at any time during or following the diagnosis of neoplasia in the subject or patient. For example, levels of HAUSP expression (or p53-HAUSP interaction) in an assayed diagnostic sample may be assessed before the subject or patient undergoes treatment for neoplasia, in order to determine the subject's or patient's initial prognosis. Additionally, levels of HAUSP expression (or p53-HAUSP interaction) in an assayed diagnostic sample may be assessed while the subject or patient is undergoing treatment for neoplasia, in order to determine whether the subject's or patient's prognosis has become more or less favorable through the course of treatment.

By way of example, where levels of HAUSP expression (or p53-HAUSP interaction) detected in an assayed diagnostic sample of the subject or patient are, or continue to remain, significantly high, a physician may conclude that the subject's or patient's prognosis is unfavorable. Where HAUSP expression (or p53-HAUSP interaction) in an assayed diagnostic sample of the subject or patient decreases through successive assessments, it may be an indication that the subject's or patient's prognosis is improving. Where levels of HAUSP expression (or p53-HAUSP interaction) in an assayed diagnostic sample of the subject or patient do not decrease significantly through successive assessments, it may be an indication that the subject's or patient's prognosis is not improving. Finally, where HAUSP expression (or p53-HAUSP interaction) is low, or is normal, in a diagnostic sample of the subject or patient, a physician may conclude that the subject's or patient's prognosis is favorable.

Similarly, the present invention provides a method for assessing the prognosis of a subject who has neoplasia, by assaying a diagnostic sample of the subject for Mdm2 expression and HAUSP expression, wherein the subject's prognosis improves with detection of a decrease in Mdm2 expression and a decrease in HAUSP expression in the diagnostic sample, and the subject's prognosis worsens with detection of an increase in Mdm2 expression and an increase in HAUSP expression in the diagnostic sample. In one embodiment, Mdm2 expression and HAUSP expression are detected in the diagnostic sample by detecting Mdm2-HAUSP interaction in the diagnostic sample.

The discovery that HAUSP can be detected in cells displaying neoplasias provides a means of identifying patients with neoplasias, and presents the potential for commercial application in the form of a test for the diagnosis of neoplasias. The development of such a test could provide general screening procedures. Such procedures can assist in the early detection and diagnosis of cancers, and can provide a method for the follow-up of patients in whom HAUSP expression (including p53-HAUSP interaction) and Mdm2 expression (including Mdm2-HAUSP interaction) elevated above normal have been detected.

Accordingly, the present invention further provides a kit for use as an assay of neoplasia, comprising an agent reactive with HAUSP and reagents suitable for detecting expression of HAUSP (and p53-HAUSP interaction). The present invention also provides a kit for use in detecting neoplasia, comprising: (a) at least one agent reactive with Mdm2; (b) at least one agent reactive with HAUSP; and (c) reagents suitable for detecting expression of Mdm2 and expression of HAUSP. The agents may be any of those described above, and may be used in any of the above-described assays or methods for detecting or quantifying HAUSP expression, Mdm2 expression, p53-HAUSP interaction, and Mdm2-HAUSP interaction. Preferably, at least one agent of the present invention is labeled with a detectable marker or label.

As indicated above, over 60% of all cancer cases are associated with p53 mutations. Therefore, p53 is the key for treating many cancers, and the p53 pathway is a particular focus of interest. p53 is generally not a stable protein; it has a half-life of approximately 20 min, and is degraded very rapidly by proteosomes in the protein-degradation pathway following ubiquitination (the binding of ubiquitin). It is believed that the stabilization of p53 is important for the protein's efficiency as a tumor suppressor.

The inventors have determined that HAUSP (or USP7) is capable of stabilizing the p53 tumor suppressor by removing ubiquitin from p53, and thereby rescuing p53 from protein degradation. Thus, HAUSP is a deubiquitinase. HAUSP significantly enhances the half-life of p53, increasing it from 20 min to 90 min. Interestingly, as described below, it also appears that HAUSP behaves as a tumor suppressor when its gene is expressed. The tumor-suppressor function of HAUSP is believed to depend on p53. While deubiquitinases have been identified in yeast, and are known to exist in mammalian cells, the discovery herein represents the first time, to the inventors' knowledge, that it has been demonstrated that a particular deubiquitinase has substrate specificity.

It is expected that some cancers associated with defects in the p53 pathway result not from a defect in p53, but from a mutated HAUSP (e.g., a mutation resulting from a genetic alteration at the coding region) and/or a defect in HAUSP regulation at the expression level (e.g., a defect resulting from a genetic alteration at the promoter region of the HAUSP gene) and/or a mutated Mdm2 and/or a defect in Mdm2 regulation at the expression level. In view of the foregoing, it is clear that modulation of the levels of HAUSP, Mdm2, and/or HAUSP-Mdm2 in cells provides a means for enhancing p53's tumor-suppressor function, and for supplementing this function with HAUSP's own tumor-suppressor activity. Accordingly, the present invention further provides a method for treating neoplasia in a subject in need of treatment therefor, comprising increasing activity of HAUSP in the subject. The neoplasia may be any of those described above, but is preferably a p53-associated neoplasia.

In accordance with the method of the present invention, activity of HAUSP in a subject may be increased by targeting HAUSP directly. Additionally, activity of HAUSP in a subject may be increased indirectly, by targeting an enzyme or other endogenous molecule that regulates or modulates the functions or levels of HAUSP in the subject. Preferably, HAUSP activity in the subject is enhanced by at least 10% in the method of the present invention. More preferably, HAUSP activity is enhanced by at least 20%.

For example, activity of HAUSP in a subject may be increased by directly or indirectly activating, facilitating, or stimulating one or more functions of HAUSP in the subject (e.g., by the modulation or regulation of proteins that interact with HAUSP). The term "activating", as used herein, means stimulating or inducing the functions of HAUSP in the subject, particularly the deubiquitination, and resulting stabilization, of p53. In the method of the present invention, HAUSP in a subject may be activated, for example, by administering to the subject a small molecule or protein mimetic that stimulates HAUSP or that is reactive with HAUSP, as defined above.

Activity of HAUSP in a subject also may be increased by directly or indirectly causing, inducing, or stimulating the upregulation of HAUSP expression within a subject. Accordingly, in one embodiment of the present invention, activity of HAUSP is increased in a subject by administering to the subject a modulator of HAUSP expression in an amount effective to treat the neoplasia in the subject. As used herein, a "modulator of expression" may be any agent or combination of agents that that has an antagonistic (inhibitory) or agonistic (facilitatory) effect on expression of a specified protein. Thus, a modulator of expression may be an agonist or an antagonist. The modulators of the present invention include any protein, polypeptide, peptide, nucleic acid (including DNA or RNA), antibody, Fab fragment, $F(ab')_2$ fragment, molecule, compound, antibiotic, and drug, and an agent reactive with a protein of interest (e.g., HAUSP) that induces or upregulates expression of that protein.

Modulators of HAUSP may be identified using a simple screening assay. For example, to screen for candidate modulators of HAUSP, human lung carcinoma cells (H1299) may be plated onto microtiter plates, then contacted with a library of drugs. Any resulting increase in, or upregulation of, HAUSP expression then may be detected using nucleic acid hybridization and/or immunological techniques known in the art, including an ELISA. Additional modulators of HAUSP expression may be identified using screening procedures well known in the art or disclosed herein. Modulators of HAUSP will be those drugs which induce or upregulate expression of HAUSP. In this manner, candidate modulators also may be screened for their ability to inhibit proliferation of neoplasms using HAUSP expression as an indicator that cell division or growth of cells in a neoplasm is decreasing in rate, or has stopped.

It is within the confines of the present invention that the modulator of HAUSP expression may be linked to another agent, or administered in combination with another agent, such as an antineoplastic drug or a ribozyme, in order to increase the effectiveness of the treatment of neoplasia, increase the efficacy of targeting, and/or increase the efficacy of p53 deubiquitination. Examples of antineoplastic drugs to which the modulator of HAUSP expression may be linked include, without limitation, carboplatin, cyclophosphamide, doxorubicin, etoposide, and vincristine.

Activity of HAUSP in a subject also may be increased in a subject by directly or indirectly increasing levels of HAUSP in vivo within the subject. By way of example, the level of HAUSP in a subject may be increased by administering HAUSP protein to the subject, in an amount effective to treat neoplasia in the subject. Similarly, the level of HAUSP in a subject may be increased by administering to the subject a nucleic acid sequence encoding HAUSP, in a manner permitting expression of HAUSP in the subject, and in an amount effective to treat the neoplasia.

The present invention contemplates the use of proteins and protein analogues generated by synthesis of polypeptides in vitro (e.g., by chemical means or by in vitro translation of mRNA). For example, HAUSP and Mdm2 may be synthesized by methods commonly known to one skilled in the art (*Modern Techniques of Peptide and Amino Acid Analysis* (New York: John Wiley & Sons, 1981; Bodansky, M., *Principles of Peptide Synthesis* (New York: Springer-Verlag New York, Inc., 1984). Examples of methods that may be employed in the synthesis of the amino acid sequences, and analogues of these sequences, include, but are not limited to, solid-phase peptide synthesis, solution-method peptide synthesis, and synthesis using any of the commercially-available peptide synthesizers. The amino acid sequences of the present invention may contain coupling agents and protecting groups, which are used in the synthesis of protein sequences, and which are well known to one of skill in the art.

In accordance with the method of the present invention, HAUSP protein may be administered to a subject who has neoplasia, either alone or in combination with one or more antineoplastic drugs used to treat neoplasias. Examples of antineoplastic drugs with which the HAUSP protein may be combined include, without limitation, carboplatin, cyclophosphamide, doxorubicin, etoposide, and vincristine.

In the method of the present invention, a modulator of HAUSP expression, a HAUSP protein, or a nucleic acid sequence encoding HAUSP is administered to a subject who has neoplasia in an amount effective to treat the neoplasia in the subject. As used herein, the phrase "effective to treat the neoplasia" means effective to ameliorate or minimize the clinical impairment or symptoms resulting from the neoplasia. For example, the clinical impairment or symptoms of the neoplasia may be ameliorated or minimized by diminishing any pain or discomfort suffered by the subject; by extending the survival of the subject beyond that which would otherwise be expected in the absence of such treatment; by inhibiting or preventing the development or spread of the neoplasia; or by limiting, suspending, terminating, or otherwise controlling the maturation and proliferation of cells in the neoplasm. The amount of modulator of HAUSP expression, HAUSP protein, or nucleic acid encoding HAUSP that is effective to treat neoplasia in a subject will vary depending on the particular factors of each case, including the type of neoplasia, the stage of neoplasia, the subject's weight, the severity of the subject's condition, and the method of administration. These amounts can be readily determined by the skilled artisan.

In the method of the present invention, the modulator of HAUSP expression, the HAUSP protein, or the nucleic acid sequence encoding HAUSP may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration), transdermal administration, and administration by osmotic pump. One preferred method of administration is parenteral administration, by intravenous or subcutaneous injection.

For oral administration, the formulation of the HAUSP modulator, protein, or nucleic acid may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration, the HAUSP modulator, protein, or nucleic acid may be combined with a sterile aqueous solution, which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampules or vials. The formulation also may be delivered by any mode of injection, including any of those described above.

For transdermal administration, the HAUSP modulator, protein, or nucleic acid may be combined with skin penetration enhancers, such as propylene glycol, polyethylene glycol, isopropanol, ethanol, oleic acid, N-methylpyrrolidone, and the like, which increase the permeability of the skin to the modulator, protein, or nucleic acid, and permit the modulator, protein or nucleic acid to penetrate through the skin and into the bloodstream. The composition of enhancer and modulator, protein, or nucleic acid also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The modulator, protein, or nucleic acid may be administered transdermally, at or near the site on the subject where the neoplasm is localized. Alternatively, the modulator, protein, or nucleic acid may be administered transdermally at a site other than the affected area, in order to achieve systemic administration.

The HAUSP modulator, protein, or nucleic acid of the present invention also may be released or delivered from an osmotic mini-pump or other time-release device. The release rate from an elementary osmotic mini-pump may be modulated with a microporous, fast-response gel disposed in the release orifice. An osmotic mini-pump would be useful for controlling release, or targeting delivery, of the modulator, protein, or nucleic acid.

In accordance with the methods of the present invention, where the modulator of HAUSP expression is a protein, or where HAUSP protein is the therapy of choice, the protein may be administered to a subject by introducing to the subject the protein itself, or by introducing to the subject a nucleic acid encoding the protein in a manner permitting expression of the protein. Accordingly, in one embodiment of the present invention, activity of HAUSP in a subject may be increased by administering to the subject an amount of a protein (e.g., a modulator of HAUSP expression, or the HAUSP protein itself). In a further embodiment of the present invention, activity of HAUSP in the subject may be increased by administering to the subject a nucleic acid sequence encoding a protein (e.g., a modulator of HAUSP expression, or the HAUSP protein itself), in a manner permitting expression of HAUSP in the subject.

The proteins of the present invention may be administered or introduced to a subject by known techniques used for the introduction of proteins and other drugs, including, for example, injection and transfusion. Where a neoplasm is localized to a particular portion of the body of the subject, it may be desirable to introduce the therapeutic protein directly to that area by injection or by some other means (e.g., by introducing the protein into the blood or another body fluid). The amount of protein to be used is an amount effective to treat neoplasia in the subject, as defined above, and may be readily determined by the skilled artisan.

In the method of the present invention, where the modulator of HAUSP expression is a protein, or where HAUSP protein is the therapeutic of choice, the protein also may be administered or introduced to the subject by introducing into a sufficient number of cells of the subject a nucleic acid encoding the protein, in a manner permitting expression of the protein in the subject. The amount of nucleic acid encoding the therapeutic protein is an amount that will produce the protein in an amount effective to treat neoplasia, as defined above, in the subject. This amount may be readily determined by the skilled artisan.

Nucleic acid encoding the modulator of HAUSP expression, or the HAUSP protein, as well as any nucleotide modulators of HAUSP expression, all may be introduced to the subject using conventional procedures known in the art, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. Recombinant viral vectors suitable for gene therapy include, but are not limited to, vectors derived from the genomes of such viruses as retrovirus, HSV, adenovirus, adeno-associated virus, Semiliki Forest virus, cytomegalovirus, and vaccinia virus.

It is within the confines of the present invention that a nucleic acid encoding a modulator of HAUSP expression, or encoding the HAUSP protein itself, may be introduced into suitable cells in vitro, using conventional procedures, to achieve expression of the therapeutic protein in the cells. Cells expressing the modulator of HAUSP expression, or the HAUSP protein, then may be introduced into a subject to treat neoplasia in vivo. In such an ex vivo gene therapy approach, the cells are preferably removed from the subject, subjected to DNA techniques to incorporate nucleic acid encoding the therapeutic protein, and then reintroduced into the subject.

It is also within the confines of the present invention that a formulation containing a HAUSP modulator, protein, or nucleic acid may be further associated with a pharmaceutically-acceptable carrier, thereby comprising a pharmaceutical composition. Accordingly, the present invention further provides a pharmaceutical composition, comprising a modulator of HAUSP expression, or a HAUSP protein or a nucleic acid sequence encoding HAUSP, and a pharmaceutically-acceptable carrier. The pharmaceutically-acceptable carrier must be "acceptable" in the sense of being compatible with the other ingredients of the composition, and not deleterious to the recipient thereof. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may be conveniently presented in unit dosage.

The formulations of the present invention may be prepared by methods well-known in the pharmaceutical arts. For example, the HAUSP modulator, protein, or nucleic acid may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the HAUSP modulator, protein, or nucleic acid of the present invention to a subject to treat neoplasia. The HAUSP modulator, protein, or nucleic acid is provided in an amount that is effective to treat neoplasia in a subject to whom the pharmaceutical composition is administered. That amount may be readily determined by the skilled artisan, as described above.

The present invention further provides a method for treating neoplasia in a subject, by increasing or enhancing activity of p53 in the subject, wherein activity of p53 is increased or enhanced in the subject by modulating Mdm2-HAUSP interaction in the subject. Preferably, p53 activity in the subject is increased or enhanced by at least 10% in the method of the present invention. More preferably, p53 activity is increased or enhanced by at least 20%. The neoplasia may be any of those described above, but is preferably an Mdm2-, HAUSP-, or p53-associated neoplasia.

Mdm2-HAUSP interaction may be modulated in a subject by administering to the subject a modulator of Mdm2-HAUSP interaction. As used herein, a "modulator of Mdm2-HAUSP interaction" may be any agent or combination of agents that that has an antagonistic (inhibitory) or agonistic (facilitatory) effect on Mdm2-HAUSP interaction. Thus, a modulator of Mdm2-HAUSP interaction may be an agonist or an antagonist. The modulator of Mdm2-HAUSP may be, for example, an Mdm2 protein, a nucleic acid sequence encoding Mdm2, a modulator of Mdm2 expression, a HAUSP protein, a nucleic acid sequence encoding HAUSP, a modulator of HAUSP expression, an agent reactive with an Mdm2-HAUSP complex, and an agent that directly modulates Mdm2-HAUSP interaction. The modulator of Mdm2-HAUSP interaction, including any now known or later discovered, also may be natural or synthetic.

By way of example, Mdm2-HAUSP interaction may be modulated in a subject by directly or indirectly increasing levels of Mdm2 and HAUSP in vivo within the subject. The level of Mdm2 or HAUSP in a subject may be increased by administering Mdm2 protein or HAUSP protein, respectively to the subject. Similarly, the level of Mdm2 (or HAUSP) in a subject may be increased by administering to the subject a nucleic acid sequence encoding Mdm2 (or HAUSP), in a manner permitting expression of Mdm2 (or HAUSP) in the subject.

Mdm2-HAUSP interaction may also be modulated in a subject by directly or indirectly activating, facilitating, or stimulating one or more functions of Mdm2 or HAUSP in the subject (e.g., by the modulation or regulation of proteins that interact with Mdm2 or HAUSP). Mdm2 (or HAUSP) in a subject may be activated, for example, by administering to the subject a small molecule or protein mimetic that stimulates Mdm2 (or HAUSP) or that is reactive with Mdm2 (or HAUSP). Furthermore, Mdm2-HAUSP interaction may be modulated in a subject by directly or indirectly causing, inducing, or stimulating the upregulation of Mdm2 (or HAUSP) expression within a subject. Accordingly, in one embodiment of the present invention, Mdm2-HAUSP interaction is modulated in a subject by administering to the subject a modulator of Mdm2 (or HAUSP) expression.

Furthermore, Mdm2-HAUSP interaction may be modulated in a subject by directly or indirectly activating, facilitating, modulating, regulating, or stimulating proteins that are reactive with an Mdm2-HAUSP complex or that otherwise modulate Mdm2-HAUSP interaction. Accordingly, in another embodiment, Mdm2-HAUSP interaction is modulated in a subject by administering to the subject an agent reactive with an Mdm2-HAUSP complex, and an agent that directly modulates Mdm2-HAUSP interaction.

Modulators for use in the method of the present invention include, without limitation, proteins, polypeptides, peptides, nucleic acids (including DNA or RNA), antibodies, Fab fragments, F(ab')$_2$ fragments, molecules, compounds, antibiotics, drugs, an agent reactive with HAUSP that induces or upregulates HAUSP expression, an agent reactive with Mdm2 that induces or upregulates Mdm2 expression, and an agent reactive with an Mdm2-HAUSP complex. Modulators of Mdm2 may be identified using a simple screening assay. For example, to screen for candidate modulators of Mdm2, cells (e.g., Mdm2-null cells or cells comprising Mdm2) may be plated onto microtiter plates, then contacted with a library of drugs. Any resulting increase in, or upregulation of, Mdm2 expression then may be detected using nucleic acid hybridization and/or immunological techniques known in the art, including an ELISA. Modulators of Mdm2 will be those drugs which induce or upregulate expression of Mdm2. Additional modulators of Mdm2 expression, as well as agents reactive with an Mdm2-HAUSP complex and agents that directly modulate Mdm2-HAUSP interaction, may be identified using screening procedures well known in the art or disclosed herein.

In the method of the present invention, a modulator of Mdm2-HAUSP interaction is administered (either alone or in combination with one or more antineoplastic drugs) by known procedures, including those described herein, to a subject who has neoplasia. The modulator of choice is provided in an amount effective to increase activity of p53 in the subject, thereby treating the neoplasia in the subject. This amount will vary depending on the particular factors of each case, including the type of neoplasia, the stage of neoplasia, the subject's weight, the severity of the subject's condition, and the method of administration, but can be readily determined by the skilled artisan.

As disclosed herein, the inventors have used mass-spectrometry analysis of affinity-purified p53-associated factors to determine that HAUSP interacts with p53. HAUSP strongly stabilizes p53, even in the presence of excess Mdm2, and induces p53-dependent cell-growth repression and apoptosis. Significantly, HAUSP has an intrinsic enzymatic activity that specifically deubiquitinates p53, both in vitro and in vivo. In contrast, expression of a catalytically-inactive HAUSP point mutant in cells increases the levels of p53 ubiquitination, and destabilizes p53. These findings reveal an important mechanism by which p53 can be stabilized by direct deubiquitination. In view of the foregoing, the present invention further provides a method for deubiquitinating and/or stabilizing p53 in a cell containing p53. The method comprises contacting the cell with HAUSP, in an amount effective to deubiquitinate and/or stabilize p53. As used herein, the singular forms "a", "an", and "the" include plural reference, unless the context clearly dictates otherwise. For example, reference to "a cell" includes a plurality of such cells, and equivalents thereof known to those skilled in the art.

The method of the present invention may be used to deubiquitinate p53, or remove ubiquitin from p53, in vitro, or in vivo in a subject. Deubiquitination of p53 may be detected by known procedures, including any of the methods, molecular procedures, and assays disclosed herein. The ability of HAUSP to modulate deubiquitination of p53 renders HAUSP particularly useful for treating neoplasias, particularly p53-associated neoplasias, as described above. Accordingly, in one embodiment of the present invention, the subject is a human with neoplasia, and the HAUSP treats the neoplasia.

HAUSP may be contacted with a cell containing p53 in vitro, or in vivo in a subject, by introducing HAUSP protein to the cell, or by introducing a nucleic acid sequence encoding HAUSP to the cell, in a manner permitting expression of HAUSP. The cell may be contained in tissue of the subject, and may be detected in tissue of the subject by standard detection methods readily determined from the known art, examples of which include, without limitation, immunological techniques (e.g., immunohistochemical staining), fluorescence imaging techniques, and microscopic techniques. In one embodiment of the present invention, the contacting is effected in vivo in a subject by administering HAUSP to the subject. Methods and formulations for introducing or administering proteins and nucleic acid sequences to subjects have already been described.

Additionally, the present invention provides a method for deubiquitinating and/or stabilizing Mdm2 in a cell containing Mdm2. The method comprises contacting the cell with HAUSP, in an amount effective to deubiquitinate and/or stabilize Mdm2. The method of the present invention may be used to deubiquitinate Mdm2, or remove ubiquitin from Mdm2, in vitro, or in vivo in a subject. Deubiquitination of Mdm2 may be detected by known procedures, including any of the methods, molecular procedures, and assays disclosed herein. The ability of HAUSP to modulate deubiquitination of Mdm2 renders HAUSP useful for treating neoplasias, particularly Mdm2-, HAUSP-, and p53-associated neoplasias. Accordingly, in one embodiment of the present invention, the subject is a human with neoplasia, and the HAUSP treats the neoplasia. To effect contact between HAUSP and at least one cell in the subject, the HAUSP may be administered to the subject by any mode of administration, including any of those disclosed herein.

The inventors have also disclosed herein that the stability and deubiquitination of p53 in a cell may be affected by the interaction between Mdm2 and HAUSP. For example, the inventors have shown that HAUSP is required for Mdm2 stability in normal cells; in HAUSP-ablated cells, though, self-ubiquitinated Mdm2 becomes extremely unstable, leading to indirect p53 activation. The inventors have also shown that Mdm2-mediated p53 degradation is strongly rescued by HAUSP expression, and that Mdm2 is thereby stabilized. Accordingly, the present invention further provides a method for modulating deubiquitination and/or stability of p53 in a cell containing p53. The method comprises contacting the cell with a modulator of Mdm2-HAUSP interaction, in an amount effective to modulate deubiquitination and/or stability of p53.

The method of the present invention may be used to modulate deubiquitination of p53 (i.e., by removing ubiquitin from p53, or adding ubiquitin to p53) in vitro, or in vivo in a subject. As disclosed herein, where deubiquitination of p53 is increased, stability of p53 will also be increased; the deubiquitination of p53 may then lead to induction of p21. Accordingly, in one embodiment of the present invention, deubiquitination of p53 is increased in the cell, stability of p53 is increased in the cell, and p21 is induced in the cell. The ubiquitination and deubiquitination of p53 may be detected by known procedures, including any of the methods, molecular procedures, and assays disclosed herein.

The ability of Mdm2-HAUSP interaction to modulate deubiquitination of p53 renders modulators of Mdm2-HAUSP interaction useful for treating neoplasias, particularly Mdm2-, HAUSP-, and p53-associated neoplasias. Accordingly, in one embodiment of the present invention, the subject is a human with neoplasia, and the modulator of Mdm2-HAUSP interaction treats the neoplasia.

A modulator of Mdm2-HAUSP interaction may be contacted with a cell containing p53 in vitro, or in vivo in a subject, by introducing a protein modulator to the cell, or by introducing a nucleic acid sequence encoding the modulator to the cell, in a manner permitting expression of the modulator. The cell may be contained in tissue of the subject, and may be detected in tissue of the subject by standard detection methods readily determined from the known art, as described above. In one embodiment of the present invention, the contacting is effected in vivo in a subject by administering a modulator of Mdm2-HAUSP interaction to the subject. Methods and formulations for introducing or administering proteins and nucleic acid sequences to subjects have been disclosed herein.

The present invention also provides a method for identifying an agent that is reactive with p53, by assessing the ability of a candidate agent to inhibit HAUSP-p53 interaction. Unless otherwise indicated, "p53" includes both a p53 protein (GenBank Accession No. CAA38095), including conservative substitutions thereof, and a p53 analogue. A "p53 analogue" is a functional variant of the p53 protein, having p53 biological activity, that has 60% or greater (preferably, 70% or greater) amino-acid-sequence homology with the p53 protein. As further used herein, the term "p53 biological activity" refers to the activity of a protein or peptide that demonstrates detectable binding with HAUSP (i.e., binding of approximately two fold, or, more preferably, approximately five fold, above the background binding of a negative control), under the conditions of the assays described herein, although affinity may be different from that of p53.

The method of the present invention comprises the steps of: (a) contacting a candidate agent with p53, in the presence of HAUSP; and (b) assessing the ability of the candidate agent to inhibit HAUSP-p53 interaction. As used herein, an "agent" shall have the definition provided above, and shall include any examples of agents described above. An agent that binds to p53 may be either natural or synthetic. An agent that is reactive with p53, as disclosed herein, would have the ability to inhibit HAUSP-p53 interaction by binding to p53 in the place of HAUSP, thereby inhibiting the interaction of HAUSP and p53. A candidate agent having the ability to bind p53 would, as a consequence of this binding, either prevent p53 activity through steric hindrance, or mimic HAUSP in its deubiquitination of p53 and thereby reinforce the stabilizing power of HAUSP.

According to the method of the present invention, an agent that is reactive with p53 may be identified using an in vitro assay (e.g., direct binding assay, competitive binding assay, etc.). For instance, in a direct binding assay, the binding of a candidate agent to p53 or a peptide fragment thereof may be measured directly. The candidate agent may be supplied by a peptide library, for example.

Alternatively, in a competitive binding assay, standard methodologies may be used in order to assess the ability of a candidate agent to displace or replace HAUSP in its binding to p53, thereby inhibiting the interaction of HAUSP and p53. In such a competitive binding assay, the candidate agent competes with HAUSP for binding to p53, and, once bound to p53, may either sterically hinder binding of HAUSP to p53, thereby preventing deubiquitination of p53 by HAUSP, or function as HAUSP in deubiquitinating or otherwise stabilizing p53. A competitive binding assay represents a convenient way to assess inhibition of HAUSP-p53 interaction, since it allows the use of crude extracts containing p53 and HAUSP.

A competitive binding assay may be carried out by adding p53, or an extract containing p53 biological activity (as defined above), to a mixture containing the candidate agent and labeled HAUSP, both of which are present in the mixture in known concentrations. After incubation, the p53/agent complex may be separated from the unbound labeled HAUSP and unlabeled candidate agent, and counted. The concentration of the candidate agent required to inhibit 50% of the binding of the labeled HAUSP to p53 (IS) then may be calculated.

The binding assay formats described herein employ labeled assay components. Labeling of HAUSP or p53 may be accomplished using one of a variety of different chemiluminescent and radioactive labels known in the art, including any of those described above. Qualitative results may be obtained by competitive autoradiographic-plate binding assays; alternatively, Scatchard plots may be used to generate quantitative results. The labels of the present invention may be coupled directly or indirectly to the desired component of the assay, according to methods well known in the art. The choice of label depends on a number of relevant factors, including the sensitivity required, the ease of conjugation with the compound to be labeled, stability requirements, and available instrumentation.

Both direct and competitive binding assays may be used in a variety of different configurations. In one competitive binding assay, for example, the candidate agent may compete against labeled HAUSP (the labeled analyte) for a specific binding site on p53 (the capture agent) that is bound to a solid substrate, such as a column chromatography matrix or tube. Alternatively, the candidate agent may compete for a specific binding site on labeled p53 (the labeled analyte) against wild-type HAUSP or a fragment thereof (the capture agent) that is bound to a solid substrate. The capture agent is bound to the solid substrate in order to effect separation of bound labeled analyte from the unbound labeled analyte. In either type of competitive binding assay, the concentration of labeled analyte that binds the capture agent bound to the solid substrate is inversely proportional to the ability of a candidate agent to compete in the binding assay. The amount of inhibition of labeled analyte by the candidate agent depends on the binding assay conditions and on the concentrations of candidate agent, labeled analyte, and capture agent that are used.

Another competitive binding assay may be conducted in a liquid phase. In this type of assay, any of a variety of techniques known in the art may be used to separate the bound labeled analyte (which may be either HAUSP or p53) from the unbound labeled analyte. Following such separation, the amount of bound labeled analyte may be determined. The amount of unbound labeled analyte present in the separated sample is inversely proportional to the amount of bound labeled analyte.

In the further alternative, a homogeneous binding assay may be performed, in which a separation step is not needed. In this type of binding assay, the label on the labeled analyte (which may be either HAUSP or p53) is altered by the binding of the analyte to the capture agent. This alteration in the labeled analyte results in a decrease or increase in the signal emitted by the label, so that measurement of the label at the end of the binding assay allows for detection or quantification of the analyte.

Under specified assay conditions, a candidate agent is considered to be capable of inhibiting the binding of HAUSP to p53 in a competitive binding assay if the amount of binding of the labeled analyte to the capture agent is decreased by 50% (preferably 90%) or more. Where a direct binding assay configuration is used, a candidate agent is considered to bind p53 when the signal measured is twice the background level or higher. Furthermore, as proof of the specificity of the candidate agent identified using a HAUSP competitive binding assay, binding competition also may be performed using purified p53 in the presence of washed ribosomes.

The p53 tumor suppressor is activated by numerous stressors to induce apoptosis, cell-cycle arrest, or senescence. p53-mediated biological activity is often the focus of research because, as described herein, p53 has a strong tumor-suppressor function. Nevertheless, p53 has also been implicated in other biological events. For example, in mice having a deletion mutation in the first six exons of the p53 gene—a mutation which confers phenotypes consistent with activated, rather than inactivated, p53—it has been shown that enhanced resistance to spontaneous tumors was accompanied by early onset of phenotypes associated with aging, including reduced longevity, osteoporosis, generalized organ atrophy, and a diminished stress tolerance. These data suggest that p53 has a role in regulating aging in an organism (Tyner et al., p53 mutant mice that display early ageing-associated phenotypes. *Nature,* 415:45-53, 2002).

Additionally, it has been suggested that p53 plays a role in generating side-effects relating to usage of chemotherapeutics. Anticancer drugs stimulate apoptosis in hair follicles (HF), and cause hair loss—the most common side-effect of chemotherapy. In one mouse model for chemotherapy-induced hair loss, it was demonstrated that p53 is essential for this process. Specifically, in contrast to wild-type mice, p53-deficient mice displayed neither hair loss nor apoptosis in HF keratinocytes that maintained active proliferation after cyclophosphamide treatment. These observations indicate that local pharmacological inhibition of p53 may be useful to prevent chemotherapy-associated hair loss (Botchkarev et al., p53 is essential for chemotherapy-induced hair loss. *Cancer Res.,* 60:5002-02, 2000).

In view of the foregoing, it is clear that therapeutics designed around, or similar to, the structure of HAUSP may be useful in treating a number of conditions associated with p53, including neoplasia, aging, and chemotherapeutic-induced or drug-induced side effects. Thus, once the candidate agent of the present invention has been screened, and has been determined to have suitable binding affinity to p53 (i.e., it is reactive with p53), it may be evaluated to ascertain whether it has an effect on biological events or processes in which p53 has been implicated, including neoplasia, aging, and side-effects associated with usage of pharmaceuticals and other chemotherapeutics. In particular, the candidate agent may be assessed for its ability to act as an inhibitor to cell division or to otherwise function as an appropriate tumor-suppressing agent. It is expected that the candidate agent of the present invention will be useful to treat neoplasias, including those disclosed herein. The candidate agent also may be assessed for its ability to attenuate adverse effects associated with aging, or adverse effects associated with administration of a chemotherapeutic to a subject.

Accordingly, the present invention further comprises the steps of: (c) contacting the candidate agent with one or more cells containing p53; and (d) determining if the agent has an effect on one or more p53-associated biological events in the one or more cells. As used herein, a "p53-associated biological event" includes a biochemical or physiological process in which p53 activity has been implicated. As disclosed herein, examples of p53-associated biological events include p53-associated neoplasia, adverse effects associated with the aging process (e.g., diminished stress tolerance, generalized organ atrophy, osteoporosis, and reduced longevity), and adverse side-effects associated with administration or use of pharmaceuticals and other chermotherapeutics (e.g., alopecia, or hair loss, and nausea).

In one embodiment of the present invention, for example, the method may further comprise the steps of: (c) contacting the candidate agent with one or more cells of a neoplasm (neoplastic cells); and (d) determining if the agent has an effect on proliferation of the neoplastic cells. As used herein, "proliferation" includes, without limitation, division, growth, and multiplication of neoplastic cells. Examples of neoplastic cells with which the candidate agent may be contacted include human lung carcinoma cells (H1299) and any other neoplastic cells containing p53. As further used herein, a cell "containing p53" is a cell in which p53, or a derivative or homologue thereof, is naturally expressed or naturally occurs. According to this method of the present invention, a candidate agent may be contacted with neoplastic cells in vitro. For example, a culture of neoplastic cells may be incubated with a preparation containing the candidate agent. The candidate agent's effect on proliferation of the neoplastic cells then may be assessed by any biological assays or methods known in the art, including histological analyses.

The present invention further provides a method for identifying an agent that is reactive with Mdm2. The method of the present invention comprises the steps of: (a) contacting a candidate agent with Mdm2, in the presence of HAUSP; and (b) assessing the ability of the candidate agent to inhibit Mdm2-HAUSP interaction (e.g., to inhibit deubiquitination of Mdm2). Unless otherwise indicated, "Mdm2" includes both an Mdm2 (murine double minute 2) protein and an Mdm2 analogue. As further used herein, an "Mdm2 analogue" is a functional variant of the Mdm2 protein, having Mdm2 biological activity, that has 60% or greater (preferably, 70% or greater) amino-acid-sequence homology with the Mdm2 protein. An Mdm2 "analogue" includes a variant of the Mdm2 protein that has an homologous three-dimensional conformation. The term "Mdm2 biological activity", as used herein, refers to the activity of a protein or peptide that demonstrates an ability to ubiquitinate p53, as described herein. Mdm2 and Mdm2 analogues may be produced synthetically or recombinantly, or may be isolated from native cells. Mdm2 is preferably produced recombinantly, using conventional techniques and cDNA encoding Mdm2.

An agent that binds to, or reacts with, Mdm2 may be either natural or synthetic. An agent that is reactive with Mdm2 may inhibit Mdm2-HAUSP interaction by preventing Mdm2 activity and/or Mdm2-HAUSP interactions through steric hindrance, and may have a structure that is similar to that of HAUSP. An agent that is reactive with Mdm2 may also mimic HAUSP in its deubiquitination of Mdm2, and thereby enhance the stability of Mdm2. According to the method of the present invention, an agent that is reactive with Mdm2 may be identified using an in vitro assay (e.g., a direct binding assay, a competitive binding assay, a homogeneous binding assay, etc.), in accordance with techniques known in the art and/or disclosed herein.

Therapeutics designed around, or similar to, the structure of HAUSP may be useful in treating conditions associated with Mdm2, including neoplasia. Furthermore, as discussed above, therapeutics designed around, or similar to, the structure of HAUSP may also be useful in treating a number of conditions associated with p53, including neoplasia, aging, and chemotherapeutic-induced or drug-induced side effects. Thus, once the candidate agent of the present invention has been screened, and has been determined to have suitable binding affinity to Mdm2 (i.e., it is reactive with Mdm2), it may be evaluated to ascertain whether it has an effect on biological events or processes in which Mdm2, HAUSP, and p53 have been implicated, including neoplasia, aging, and side-effects associated with usage of pharmaceuticals and other chemotherapeutics. In particular, the candidate agent may be assessed for its ability to act as an inhibitor to cell division or to otherwise function as an appropriate tumor-suppressing agent. It is expected that the candidate agent of the present invention will be useful to treat neoplasias, including those disclosed herein. The candidate agent also may be assessed for its ability to attenuate adverse effects associated with aging, or adverse effects associated with administration of a chemotherapeutic to a subject.

Accordingly, the present invention further comprises the steps of: (c) contacting the candidate agent with one or more cells comprising Mdm2, HAUSP, or p53; and (d) determining if the agent has an effect on one or more Mdm2-, HAUSP-, or p53-associated biological events in the one or more cells. As used herein, an "Mdm2-associated biological event" includes a biochemical or physiological process in which Mdm2 activity has been implicated (e.g., neoplasia), and a "HAUSP-associated biological event" includes a biochemical or physiological process in which HAUSP activity has been implicated (e.g., neoplasia). In one embodiment of the present invention, for example, the method may further comprise the steps of: (c) contacting the candidate agent with one or more cells of a neoplasm (neoplastic cells); and (d) determining if the agent has an effect on proliferation of the neoplastic cells. As further used herein, a cell "comprising Mdm2 or HAUSP" is a cell in which Mdm2 or HAUSP, or a derivative or homologue thereof, is naturally expressed or naturally occurs.

Similarly, the present invention provides a method for identifying an agent that is reactive with HAUSP. The method of the present invention comprises the steps of: (a) contacting a candidate agent with HAUSP, in the presence of Mdm2; and (b) assessing the ability of the candidate agent to inhibit HAUSP-Mdm2 interaction. An agent that binds to, or reacts with, HAUSP may be either natural or synthetic. An agent that is reactive with HAUSP may inhibit HAUSP-Mdm2 interaction by preventing HAUSP activity and/or HAUSP-Mdm2 interactions through steric hindrance, and may have a structure similar to that of Mdm2. According to the method of the present invention, an agent that is reactive with HAUSP may be identified using an in vitro assay (e.g., a direct binding assay, a competitive binding assay, a homogeneous binding assay, etc.), in accordance with techniques known in the art and/or disclosed herein.

Therapeutics designed to inhibit Mdm2-HAUSP interaction may be useful in treating conditions associated with Mdm2, including neoplasia. Furthermore, therapeutics designed around, or similar to, the structure of Mdm2 may also be useful in treating a number of conditions associated with p53, including neoplasia, aging, and chemotherapeutic-induced or drug-induced side effects. Thus, once the candidate agent of the present invention has been screened, and has been determined to have suitable binding affinity to HAUSP (i.e., it is reactive with HAUSP), it may be evaluated to ascertain whether it has an effect on biological events or processes in which Mdm2, HAUSP, and p53 have been implicated, including neoplasia, aging, and side-effects associated with usage of pharmaceuticals and other chemotherapeutics. In particular, the candidate agent may be assessed for its ability to act as an inhibitor to cell division or to otherwise function as an appropriate tumor-suppressing agent. It is expected that the candidate agent of the present invention will be useful to treat neoplasias, including those disclosed herein. The candidate agent also may be assessed for its ability to attenuate adverse effects associated with aging, or adverse effects associated with administration of a chemotherapeutic to a subject. Accordingly, the present invention further comprises the steps of: (c) contacting the candidate agent with one or more cells comprising Mdm2, HAUSP, or p53; and (d) determining if the agent has an effect on one or more Mdm2-, HAUSP-, or p53-associated biological events in the one or more cells.

The present invention also provides a method for identifying a modulator of Mdm2-HAUSP interaction, by assessing the ability of a candidate modulator to affect (i.e., increase or decrease) Mdm2-HAUSP interaction. The method of the present invention comprises the steps of: (a) obtaining or generating an in vitro system comprising Mdm2 and HAUSP; (b) contacting the in vitro system with a candidate modulator; and (c) determining if the candidate modulator modulates Mdm2-HAUSP interaction in the in vitro system. By way of example, the in vitro system of the present invention may be a collection of cells (e.g., a culture of cells). Preferably, however, the in vitro system is a non-cell system, such as a mixture of purified proteins (e.g., Mdm2 and HAUSP), a cell lysate (e.g., further comprising an anti-Mdm2 or anti-HAUSP antibody), a reconstructed cell lysate, or a mixture of cell lysates.

The skilled artisan can determine whether any particular candidate is a modulator of Mdm2-HAUSP interaction by any of several well-known methods, including comparison with non-treated controls and any assays disclosed herein. By way of example, the determination in step (c) may be made by comparing Mdm2-HAUSP interaction in the in vitro system of step (b) with Mdm2-HAUSP interaction in a second in vitro system that comprises Mdm2 and HAUSP in the absence of the candidate modulator. Alternatively, where the in vitro system is a collection of cells, an antagonist specific for HAUSP or Mdm2 may be added to the in vitro system of step (b), and the determination in step (c) may be made by comparing Mdm2-HAUSP interaction in the in vitro system of step (b) with Mdm2-HAUSP interaction in a second in vitro system that comprises Mdm2, HAUSP, and the candidate modulator, in the absence of the selected antagonist. In the further alternative, where the in vitro system is a non-cell system, an anti-HAUSP antibody or anti-Mdm2 antibody may be added to the in vitro system of step (b), and the determination in step (c) may be made by comparing Mdm2-HAUSP interaction in the in vitro system of step (b) with Mdm2-HAUSP interaction in a second in vitro system that comprises Mdm2, HAUSP, and the candidate modulator, in the absence of the selected antibody. For example, where the antibody is an anti-HAUSP monoclonal antibody, the level of activity of Mdm2 may be assessed in the first and second in vitro systems. If the candidate modulator has an effect on Mdm2 levels and/or activity in the second system, but not in the first system, it may be concluded that the candidate modulator has its modulating effect through HAUSP, and, therefore, is a modulator of Mdm2-HAUSP interaction.

Therapeutics designed to modulate Mdm2-HAUSP interaction may be useful in treating conditions associated with Mdm2-HAUSP, including neoplasia. Furthermore, such therapeutics may also be useful in treating a number of conditions associated with p53, including neoplasia, aging, and chemotherapeutic-induced or drug-induced side effects. Thus, once the candidate modulator of the present invention has been screened, and has been determined to have a suitable modulating effect on Mdm2-HAUSP interaction, it may be evaluated to ascertain whether it has an effect on biological events or processes in which Mdm2, HAUSP, and p53 have been implicated, including neoplasia, aging, and side-effects associated with usage of pharmaceuticals and other chemotherapeutics. In particular, the candidate modulator may be assessed for its ability to act as an inhibitor to cell division or to otherwise function as an appropriate tumor-suppressing agent. It is expected that the candidate modulator of the present invention will be useful to treat neoplasias, including those disclosed herein. The candidate modulator also may be assessed for its ability to attenuate adverse effects associated with aging, or adverse effects associated with administration of a chemotherapeutic to a subject.

The present invention is further directed to agents and modulators identified by the above-described identification methods. Such agents and modulators may be useful for treating Mdm2-, HAUSP-, and/or p53-associated conditions. As used herein, an "Mdm2-, HAUSP-, and/or p53-associated condition" is a condition, disease, or disorder in which Mdm2-, HAUSP-, and/or p53 activity has been implicated, and includes the following: Mdm2-, HAUSP-, and/or p53-associated neoplasia in a subject in need of treatment, adverse effects associated with aging in a subject in need of treatment, and adverse side-effects associated with use of a pharmaceutical or chemotherapeutic in a subject. The Mdm2-, HAUSP-, and/or p53-associated condition may be treated in the subject by administering to the subject an amount of the agent or modulator of the present invention effective to treat the Mdm2-, HAUSP-, and/or p53-associated condition in the subject. This amount may be readily determined by one skilled in the art. Accordingly, the present invention further provides a method for treating an Mdm2-, HAUSP-, or p53-associated condition in a subject, comprising administering to the subject an agent or modulator of the present invention (e.g., a modulator of Mdm2-HAUSP interaction), in an amount effective to treat the Mdm2-, HAUSP-, or p53-associated condition in the subject. Also provided is a use of an agent or modulator of the present invention (e.g., a modulator of Mdm2-HAUSP interaction) in a method of treating neoplasia.

The present invention also provides a pharmaceutical composition comprising an agent or modulator identified by one of the above-described identification methods, and a pharmaceutically-acceptable carrier. Examples of suitable pharmaceutically-acceptable carriers, and methods of preparing pharmaceutical formulations and compositions, are described above. The pharmaceutical composition of the present invention would be useful for administering to a subject an agent or modulator of the present invention, in order to treat an Mdm2-, HAUSP-, or p53-associated condition. In such cases, the pharmaceutical composition is administered to a subject in an amount effective to treat the Mdm2-, HAUSP-, or p53-associated condition.

The present invention also provides a complex comprising HAUSP and p53. In such a HAUSP-p53 complex, amino acid residues of a p53-binding site of HAUSP are in direct van der Waal and/or hydrogen bond and/or salt-bridge contact with the amino acid residues of p53. The complex of the present invention may comprise the full amino acid sequence of HAUSP complexed with the full amino acid sequence of p53. In another embodiment, the complex of the present invention comprises at least the N-terminus domain of HAUSP, which contains a p53-binding site of HAUSP.

As used herein, the "N-terminus domain of HAUSP" means residues 1-248 of HAUSP, as well as analogues thereof. Moreover, as used herein, a "binding site" refers to a region of a molecule or molecular complex that, as a result of its shape and charge potential, favorably interacts or associates with another agent—including, without limitation, a protein, polypeptide, peptide, nucleic acid (including DNA or RNA), molecule, compound, antibiotic, or drug—via various covalent and/or non-covalent binding forces. Accordingly, as contemplated by the present invention, a "p53-binding site of HAUSP" is a binding site on HAUSP that, as a result of its shape, reactivity, charge, potential, and/or other characteristics, favorably interacts or associates with another agent, including, without limitation, a protein (e.g., p53), polypeptide, peptide, nucleic acid (e.g., DNA or RNA), molecule, compound, antibiotic, or drug.

It will be obvious to the skilled practitioner that the numbering of any amino acid residues in the various isoforms of HAUSP, or in HAUSP analogues covered by the present invention, may be different than that set forth herein, or may contain certain conservative amino acid substitutions that produce the same p53-binding activity as that described herein. Corresponding amino acids and conservative substitutions in other isoforms or analogues are easily identified by visually inspecting the relevant amino acid sequences, or by using commercially-available homology software programs.

A p53-binding site of HAUSP may include the actual site on HAUSP of p53 binding. A p53-binding site also may include accessory binding sites on HAUSP, adjacent or proximal to the actual site of p53 binding, that nonetheless may affect HAUSP or p53-HAUSP activity upon interaction or association with a particular agent—either by direct interference with the actual site of p53 binding, or by indirectly affecting the steric conformation or charge potential of the HAUSP molecule, and thereby preventing or reducing p53 binding to HAUSP at the actual site of p53 binding.

Identification of a binding site of a molecule or molecular complex is important because the biological activity of the molecule or molecular complex frequently results from interaction between an agent ligand and one or more binding sites of the molecule or molecular complex. Therefore, localization of a p53-binding site of HAUSP provides the most suitable tool for identifying inhibitors that affect the activity of HAUSP or HAUSP-p53. Localization of a p53-binding site of HAUSP also permits the use of various molecular design and analysis techniques for the purpose of designing and synthesizing chemical agents capable of favorably associating or interacting with a p53-binding site of HAUSP or a HAUSP analogue, wherein said chemical agents potentially act as inhibitors of HAUSP or HAUSP-p53 activity. In view of the foregoing, the HAUSP-p53 interaction and the HAUSP-p53 complex of the present invention may be used as tools in the rational design and development of drug screens, as a target for small-molecule inhibitors that can act as inhibitor agents or modulators, and as a basis for peptidomimetics.

The present invention also provides a complex comprising Mdm2 and HAUSP. In such an Mdm2-HAUSP complex, amino acid residues of Mdm2 are in physical contact (e.g., direct van der Waal contact, contact via hydrogen bond, contact via salt bridge, etc.) with the amino acid residues of HAUSP. The complex of the present invention may comprise the full amino acid sequence of Mdm2 complexed with the full amino acid sequence of HAUSP. Alternatively, the complex of the present invention may comprise at least a portion of HAUSP, which contains at least one site of interaction or physical association with Mdm2.

The present invention further provides a point-mutant HAUSP protein (HAUSP-cs), in which a highly conserved Cys residue at the core domain is replaced by Ser. More particularly, the point-mutant protein comprises the amino acid sequence set forth in FIG. 6 (SEQ ID NO:6), in which Ser is substituted for Cys at amino acid residue 223. This mutant protein retains its strong binding with p53 in vitro. Additionally, as disclosed herein, expression of HAUSP-cs in cells increased the level of p53 ubiquitination, indicating that HAUSP-cs may function as a dominant-negative mutant by interfering with endogenous HAUSP-mediated deubiquitination of p53. Also provided herein are a nucleic acid sequence encoding the HAUSP point-mutant protein of the present invention, and a cell transfected with the nucleic acid sequence.

The present invention further provides a non-human transgenic animal that expresses either reduced, mutant, or no HAUSP gene products, or that expresses only human HAUSP gene products. In particular, the present invention provides a transgenic non-human animal in which HAUSP has been selectively inactivated. More specifically, the present invention provides a transgenic non-human animal whose genome comprises a disruption in the HAUSP gene, wherein the transgenic animal exhibits a decreased level of functional HAUSP protein relative to wild-type. The non-human animal may be any suitable animal (e.g., cat, cattle, dog, horse, goat, rodent, and sheep), but is preferably a rodent. More preferably, the non-human animal is a rat or a mouse.

Unless otherwise indicated, the term "HAUSP gene" refers herein to a nucleic acid sequence encoding HAUSP protein, and any allelic variants thereof. Due to the degeneracy of the genetic code, the HAUSP gene of the present invention includes a multitude of nucleic acid substitutions that will also encode HAUSP protein. An "endogenous" HAUSP gene is one that originates or arises naturally, from within an organism. The terms "HAUSP protein", "HAUSP analogue", and "HAUSP-protein biological activity" have been defined above.

As used herein, the term "transgenic non-human animal" refers to a genetically-engineered non-human animal, produced by experimental manipulation, whose genome has been altered by introduction of a transgene. As further used herein, the term "transgene" refers to a nucleic acid (e.g., DNA or a gene) that has been introduced into the genome of an animal by experimental manipulation, wherein the introduced gene is not endogenous to the animal, or is a modified or mutated form of a gene that is endogenous to the animal. The modified or mutated form of an endogenous gene may be produced through human intervention (e.g., by introduction of a point mutation, introduction of a frameshift mutation, deletion of a portion or fragment of the endogenous gene, insertion of a selectable marker gene, insertion of a termination codon, etc.). A transgenic non-human animal may be produced by several methods involving human intervention, including, without limitation, introduction of a transgene into an embryonic stem cell, newly fertilized egg, or early embryo of a non-human animal; integration of a transgene into a chromosome of the somatic and/or germ cells of a non-human animal; and any of the methods described herein.

The transgenic animal of the present invention has a genome in which the HAUSP gene has been selectively inactivated, resulting in a disruption in its endogenous HAUSP gene. As used herein, a "disruption" refers to a mutation (i.e., a permanent, transmissable change in genetic material) in the HAUSP gene that prevents normal expression of functional HAUSP protein (e.g., it results in expression of a mutant HAUSP protein; it prevents expression of a normal amount of HAUSP protein; or it prevents expression of HAUSP protein). Examples of a disruption include, without limitation, a point mutation, introduction of a frameshift mutation, deletion of a portion or fragment of the endogenous gene, insertion of a selectable marker gene, and insertion of a termination codon. As used herein, the term "mutant" refers to a gene (or its gene product) which exhibits at least one modification in its sequence (or its functional properties) as compared with the wild-type gene (or its gene product). In contrast, the term "wild-type" refers to the characteristic genotype (or phenotype) for a particular gene (or its gene product), as found most frequently in its natural source (e.g., in a natural population). A wild-type animal, for example, expresses functional HAUSP.

Selective inactivation in the transgenic non-human animal of the present invention may be achieved by a variety of methods, and may result in either a heterozygous disruption (wherein one HAUSP gene allele is disrupted, such that the resulting transgenic animal is heterozygous for the mutation) or a homozygous disruption (wherein both HAUSP gene alleles are disrupted, such that the resulting transgenic animal is homozygous for the mutation). In one embodiment of the present invention, the endogenous HAUSP gene of the transgenic animal is disrupted through homologous recombination with a nucleic acid sequence that encodes a region common to HAUSP gene products. By way of example, the disruption through homologous recombination may generate a knockout mutation in the HAUSP gene, particularly a knockout mutation wherein at least one deletion has been introduced into at least one exon of the HAUSP gene (e.g., exon 1).

Additionally, in accordance with the methods of the present invention, a disruption in the HAUSP gene may result from insertion of a heterologous selectable marker gene into the endogenous HAUSP gene. As used herein, the term "selectable marker gene" refers to a gene encoding an enzyme that confers upon the cell or organism in which it is expressed a resistance to a drug or antibiotic, such that expression or activity of the marker can be selected for (e.g., a positive marker, such as the neo gene) or against (e.g., a negative marker, such as the dt gene). As further used herein, the term "heterologous selectable marker gene" refers to a selectable marker gene that, through experimental manipulation, has been inserted into the genome of an animal in which it would not normally be found. Such a heterologous selectable marker gene may be inserted into any coding exon of the HAUSP gene.

The transgenic non-human animal of the present invention exhibits decreased expression of functional HAUSP protein relative to a corresponding wild-type non-human animal of the same species. As used herein, the phrase "exhibits decreased expression of functional HAUSP protein" refers to a transgenic animal in whom the detected amount of functional HAUSP is less than that which is detected in a corresponding animal of the same species whose genome contains a wild-type HAUSP gene. Preferably, the transgenic animal contains at least 50% less functional HAUSP than the corresponding wild-type animal. More preferably, the transgenic animal contains at least 75% less functional HAUSP than the corresponding wild-type animal. Even more preferably, the transgenic animal contains at least 90% less functional HAUSP than the corresponding wild-type animal. Levels of HAUSP in an animal, as well as HAUSP activity, may be detected using standard assays such as those known in the art.

Accordingly, where the transgenic animal of the present invention exhibits decreased expression of functional HAUSP protein relative to wild-type, the level of functional HAUSP protein in the transgenic animal is lower than that which otherwise would be found in nature. In one embodiment of the present invention, the transgenic animal expresses mutant HAUSP (regardless of amount). In another embodiment of the present invention, the transgenic animal expresses no HAUSP (wild-type or mutant). In yet another embodiment of the present invention, the transgenic animal expresses wild-type HAUSP protein, but at a decreased level of expression relative to a corresponding wild-type animal of the same species.

The transgenic non-human animal of the present invention, or any transgenic non-human animal exhibiting decreased expression of functional HAUSP protein relative to wild-type, may be produced by a variety of techniques for genetically engineering transgenic animals. For example, to create a transgenic non-human animal exhibiting decreased expression of functional HAUSP protein relative to a corresponding wild-type animal of the same species, a HAUSP targeting vector first may be generated, using techniques well-known in the art.

As used herein, the term "HAUSP targeting vector" refers to an oligonucleotide sequence that comprises a portion, or all, of the HAUSP gene, and is sufficient to permit homologous recombination of the targeting vector into at least one allele of the endogenous HAUSP gene within the recipient cell. In one embodiment of the present invention, the targeting vector further comprises a positive or negative heterologous selectable marker gene (e.g., the positive selection gene, neo). Additionally, the targeting vector may be a replacement vector (i.e., the selectable marker gene replaces an endogenous target gene). For example, the replacement vector of the present invention may insert a heterologous selectable marker gene into the HAUSP gene, resulting in a disruption of the HAUSP gene such that functional HAUSP protein is not expressed. Such a disruption is referred to herein as a "null" or "knockout" mutation. It is also within the scope of the present invention that the targeting vector may be an insertion vector. By way of example, the HAUSP targeting vector of the present invention may be an oligonucleotide sequence comprising at least a portion of a non-human HAUSP gene in which there is at least one deletion in at least one exon (e.g., exon 1 of HAUSP).

In the method of the present invention, the HAUSP targeting vector that has been generated may be introduced into a recipient cell (comprising a wild-type HAUSP gene) of a non-human animal, to produce a treated recipient cell. This introduction may be performed under conditions suitable for homologous recombination of the vector into at least one of the wild-type HAUSP genes in the genome of the recipient cell. The recipient cell may be, for example, an embryonic stem cell, or a cell of an oocyte or zygote.

The HAUSP targeting vector of the present invention may be introduced into the recipient cell by any in vivo or ex vivo means suitable for gene transfer, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, viral vectors, and naked DNA transfer, or any combination thereof. Recombinant viral vectors suitable for gene transfer include, but are not limited to, vectors derived from the genomes of viruses such as retrovirus, HSV, adenovirus, adeno-associated virus, Semiliki Forest virus, cytomegalovirus, and vaccinia virus.

In accordance with the methods of the present invention, the treated recipient cell then may be introduced into a blastocyst of a non-human animal of the same species (e.g., by injection or microinjection into the blastocoel cavity), to produce a treated blastocyst. Thereafter, the treated blastocyst may be introduced (e.g., by transplantation) into a pseudopregnant non-human animal of the same species, for expression and subsequent germline transmission to progeny. For example, the treated blastocyst may be allowed to develop to term, thereby permitting the pseudopregnant animal to deliver progeny comprising the homologously-recombined vector, wherein the progeny may exhibit decreased expression of HAUSP relative to corresponding wild-type animals of the same species. It then may be possible to identify a transgenic non-human animal whose genome comprises a disruption in its endogenous HAUSP gene. The identified transgenic animal then may be interbred with other founder transgenic animals, to produce heterozygous or homozygous non-human animals exhibiting decreased expression of functional HAUSP protein relative to corresponding wild-type animals of the same species. The present invention further provides a transgenic non-human animal created by the above-described method.

As discussed above, studies to date suggest that the p53 pathway is dysfunctional in most, if not all, cases of cancer, and that p53 itself is mutated in approximately 60% of all cancers. In cancer cases where wild-type p53 is detected, then, it is believed that p53 cannot be activated or stabilized because another enzyme or biochemical in the p53 pathway (e.g., HAUSP) is defective. Studies on the transgenic non-human animal of the present invention, which exhibits decreased expression of functional HAUSP protein relative to wild-type, and which lacks the wild-type HAUSP gene, may facilitate an understanding of the physiological role of HAUSP in tumorigenesis, particularly in p53-associated neoplasias. For example, the transgenic non-human animal could be used to test whether loss of HAUSP affects the development of neoplasias. A transgenic non-human animal genetically engineered to express human HAUSP also will be a valuable reagent for testing lead HAUSP compounds in vivo. Moreover, the inventors' transgenic non-human animal provides a valuable, unique, and useful reagent for screening for modulators of p53 activity that could replace HAUSP in its interaction with p53.

The present invention is described in the following Examples, which are set forth to aid in the understanding of the invention, and should not be construed to limit in any way the scope of the invention as defined in the claims which follow thereafter.

EXAMPLE 1

Plasmids and Antibodies

Plasmids and antibodies used in Examples 2-3 were prepared as follows. To construct the HAUSP and USP11 expression vectors, the DNA sequences corresponding to the full-length proteins (Everett et al., A novel ubiquitin-specific protease is dynamically associated with the PML nuclear domain and binds to a herpesvirus regulatory protein. *EMBO J.*, 16:566-77, 1997; Chung and Baek, Deubiquitinating enzymes: their diversity and emerging roles. *Biochem. Biophys. Res. Commun.*, 266:633-40, 1999) were amplified by PCR from Marathon-Ready Hela cDNA (Clontech), and subcloned either into a pcDNA3-Topo vector (Invitrogen), or with a Flag-tag into either a pET-11 vector for expression in bacteria or a pCIN4 vector and pBabe vector for expression in mammalian cells (Luo et al., Deacetylation of p53 modulates its effect on cell growth and apoptosis. *Nature*, 408:377-81, 2000; Luo et al., Negative control of p53 by Sir2α promotes cell survival under stress. *Cell*, 107:137-48, 2001). Regarding the different deletion-mutant constructs, DNA sequences corresponding to different regions were amplified by PCR from the above constructs, and subcloned into respective expression vectors. To prepare the HAUSP antibody, inventors made a polyclonal antibody against the recombinant HAUSP full-length protein. The DNA sequence corresponding to the full-length protein was subcloned into the pET-15-His vector (Novagene). α-HAUSP antisera were raised in rabbits against the purified His-HAUSP protein (Covance), and further affinity-purified on a protein-A column.

EXAMPLE 2

Identification of HAUSP as a P53-Binding Protein

Elimination of non-specific protein binding is critical for successful identification of a bonafide binding partner for p53 in an affinity chromatography assay (Gu et al., Synergistic activation of transcription by CBP and p53. *Nature*, 387:819-23, 1997; Luo et al., Deacetylation of p53 modulates its effect on cell growth and apoptosis. *Nature*, 408:377-81, 2000). Regarding this issue, the salt-concentration range between binding and elution conditions has been modified, as compared with the previous method (Gu et al., Synergistic activation of transcription by CBP and p53. *Nature*, 387:819-23, 1997; Luo et al., Deacetylation of p53 modulates its effect on cell growth and apoptosis. Nature, 408:377-81, 2000) (e.g., 200 mM NaCl for binding, 500 mM NaCl for elution) to limit the number of proteins from the elution. Furthermore, nuclear extracts were extensively pre-cleaned with the GST column before loading on the GST-pS3-affinity column. The mock purification was simultaneously performed on both the GST column loaded with the same nuclear extract, and an additional GST-p53 column loaded with a blank buffer for identifying any possible non-specific binding.

In brief, a column, which contains 40 μl of indicated GST-fusion-protein-coupled beads, was washed extensively with BC500 (25 mM Tris, 500 mM NaCl, 1 mM EDTA, 1 mM DTT, 10% glycerol, 0.2% NP40, 1% Triton X-100, 0.1% DOC, pH 7.8), and then equilibrated with BC200 (25 mM Tris, 200 mM NaCl, 1 mM EDTA, 1 mM DTT, 10% glycerol, 0.2% NP40, pH 7.8) for loading. Human lung carcinoma cells (H1299) were expanded in DMEM medium, and nuclear extracts were prepared essentially as previously described (Gu et al., Synergistic activation of transcription by CBP and p53. *Nature*, 387:819-23, 1997; Luo et al., Deacetylation of p53 modulates its effect on cell growth and apoptosis. *Nature*, 408:377-81, 2000). Nuclear extracts were adjusted to 200 mM NaCl and 0.2% NP40, and pre-cleaned by flowing through the GST column for at least three times. 800 μl of the pre-cleaned nuclear extract was loaded on either the GST or GST-p53 mini-column. After washing with 1 ml of the BC200 buffer for five times, the associated proteins were eluted from column with 40 μl of BC500. The nuclear extract derived from about 10×10$^9$ cells was used for the large preparation.

EXAMPLE 3

Stabilization of P53 and Detecting Ubiquitination Levels of P53

The p53-null H1299 cells were transfected with 0.1-2 mg of CMV-Flag-p53, 2 mg of CMV-Mdm2, 1 mg of CMV-GFP, and 5-16 mg of either CMV-HAUSP or an expression vector for the indicated HAUSP mutant or other proteins. 24 h after the transfection, the cells were lysed in a Flag-lysis buffer (50 mM Tris, 137 mM NaCl, 10 mM NaF, 1 mM EDTA, 1% Triton X-100, 0.2% Sarkosyl, 1 mM DTT, 10% glycerol, pH 7.8; and fresh proteinase inhibitors) for Western-blot analysis. The levels of GFP were detected with the anti-GFP monoclonal antibody, JL-8 (Clontech), as a transfection-efficiency control. The ubiquitination levels of p53 were detected essentially as previously described (Rodriguez et al., Multiple C-terminal lysine residues target p53 for ubiquitin-proteasome-mediated degradation. *Mol. Cell. Biol.*, 20:8458-67, 2000). The cells were treated with 50 mM of a proteasome inhibitor, LLNL (Sigma), for 4 h before harvesting, and the cells were lysed in the Flag-lysis buffer with mild sonication. The cell extracts were immunoprecipitated with the Flag monoclonal antibody (M2), and subsequently resolved by either 8% or 4-20% SDS-PAGE gel (Novex), and analyzed by Western blot with α-p53 (DO-1).

For preparing a large amount of ubiquitinated p53 as the substrate for in vitro deubiquitination assay, the H1299 cells (5×10⁷) were co-transfected with the Flag-p53 and Mdm2 expression vectors. After the same treatment as above, the ubiquitinated p53 was purified from the cell extracts on the M2-affinity column with the Flag-lysis buffer. After extensive washing with the Flag-lysis buffer, the proteins were eluted in a BC100 buffer (25 mM Tris, 100 mM NaCl, pH 7.8) with Flag-peptides (Sigma). The recombinant Flag-HAUSP and the mutant form (HAUSP-cs) were expressed in BL21 cells, and purified on the M2 column. For the in vitro deubiquitination assay reaction, the ubiquitinated p53 protein was incubated with the recombinant HAUSP (100 ng) or the same amount of other indicated proteins in a deubiquitination buffer (50 mM Tris-HCl, pH 8.0; 50 mM NaCl, 1 mM EDTA, 10 mM DTT, 5% glycerol) for 2 h at 37° C.

Summarized below are results obtained by the inventors in connection with the experiments of Examples 1-3 above.

Using a biochemical purification method with GST-p53 affinity chromatography (Gu et al., Synergistic activation of transcription by CBP and p53. *Nature,* 387:819-23, 1997; Luo et al., Deacetylation of p53 modulates its effect on cell growth and apoptosis. *Nature,* 408:377-81, 2000), the inventors have identified a p53-binding protein from nuclear extracts of human lung carcinoma cells (H1299). As indicated in FIG. 1A, there are a number of proteins present in the fractions eluted from the GST-p53 affinity column and from other columns. Strikingly, only one protein, p135 (relative molecular mass ~135,000; Mr: 135K), was specifically present in the associated factors obtained from the GST-p53 column, but was not present in the factors obtained from either the GST column or the control column (lane 3 vs. lanes 1, 2). Following a large preparation, enough material of the p135 band was obtained for mass spectrometry, and a total of five peptide sequences were obtained (SEQ ID NOs: 1-5). All five peptide sequences were derived from the herpesvirus protein Vmw110-associated cellular factor, known as HAUSP or human USP7 (Everett et al., A novel ubiquitin-specific protease is dynamically associated with the PML nuclear domain and binds to a herpesvirus regulatory protein. *EMBO J.,* 16:566-77, 1997).

Figure 9:
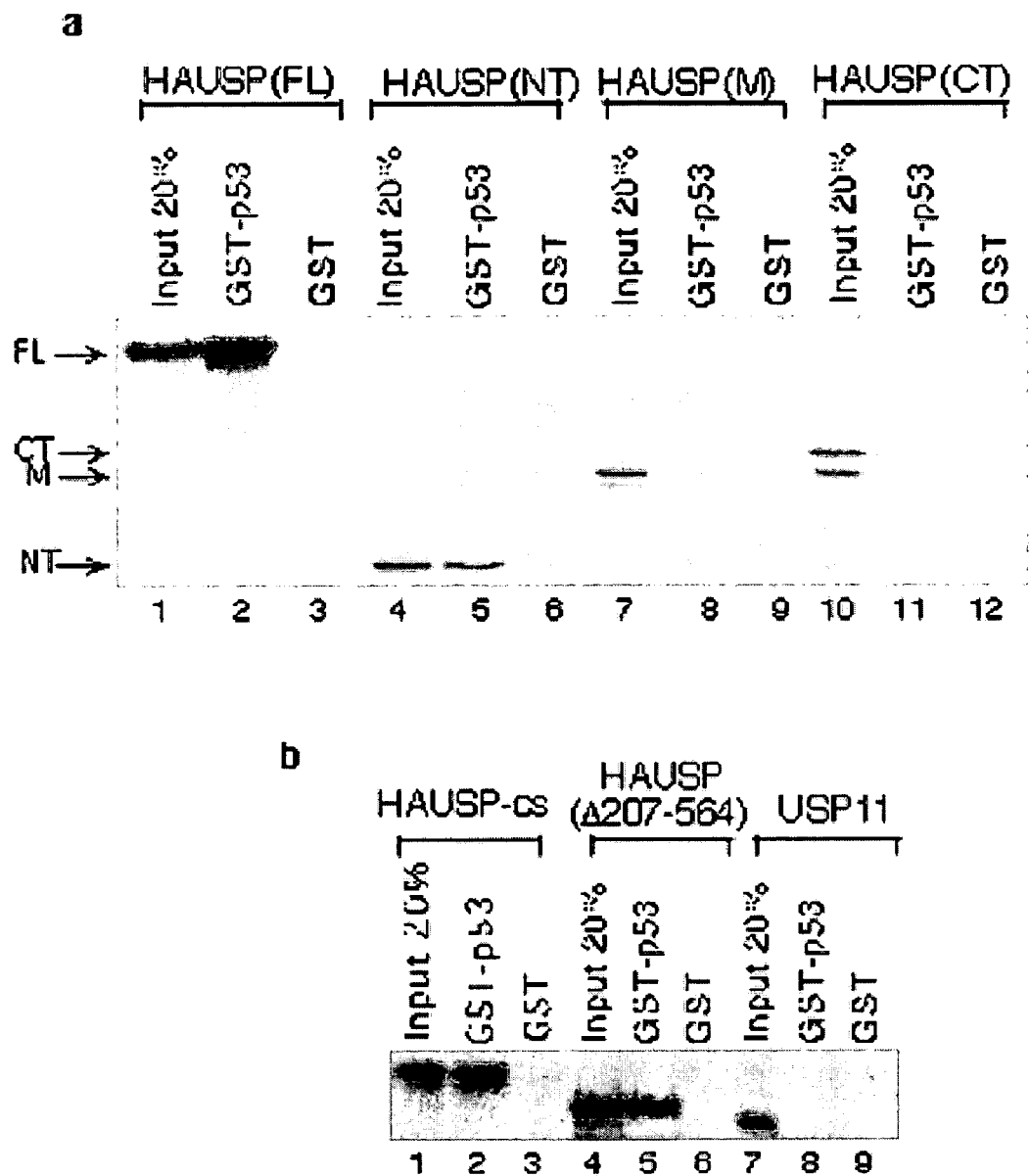
FIGS. 9A-9B depict in vitro interaction of p53 with HAUSP. (A) GST and GST-p53 fusion proteins were used in a GST pull-down assay with in vitro translated $^{35}$S-labeled full-length HAUSP (FL) (lanes 1-3), or the N-terminal extension of HAUSP (1-248) (lanes 4-6), or the core domain (245-644) of HAUSP (M) (lanes 7-9), or the C-terminal extension of HAUSP (637-1102). (B) The in vitro interaction of p53 with HAUSP-cs, HAUSP($\Delta$207-564), and USP11. The GST and GST-p53 fusion proteins were used in a GST pull-down assay with in vitro translated $^{35}$S-labeled HAUSP-cs (lanes 1-3), HAUSP($\Delta$207-564) (lanes 4-6), or USP11 (lanes 7-9).

HAUSP belongs to the ubiquitin-(Ub)-specific processing protease (UBP) family of deubiquitination enzymes (DUBs), and contains the characteristic Cys and His motifs at the core enzymatic domain (Everett et al., A novel ubiquitin-specific protease is dynamically associated with the PML nuclear domain and binds to a herpesvirus regulatory protein. *EMBO J.,* 16:566-77, 1997). Interestingly, the amino-terminal and carboxyl-terminal extensions of HAUSP which have no significant homology to other members of the UBP family, and which are thought to be critical for the substrate specificity (Everett et al., A novel ubiquitin-specific protease is dynamically associated with the PML nuclear domain and binds to a herpesvirus regulatory protein. *EMBO J.,* 16:566-77, 1997; D'Andrea and Pellman, Deubiquitinating enzymes: a new class of biological regulators. *Crit. Rev. Biochem. Mol. Biol.,* 35:337-52, 1998; Chung and Baek, Deubiquitinating enzymes: their diversity and emerging roles. *Biochem. Biophys. Res. Commun.,* 266:633-40, 1999; Wilkinson, K. D., Ubiquitination and deubiquitination: targeting of proteins for degradation by the proteasome. *Semin. Cell Dev. Biol.,* 11: 141-48, 2000), directly bind to p53 in vitro. However, as shown in FIG. 9, $^{35}$S-labeled in vitro-translated HAUSP bound strongly to GST-p53, but not to GST alone (lane 2 vs. 3). Moreover, p53 bound tightly to the N-terminal extension [HAUSP(NT)] of HAUSP (lane 2, FIG. 9B), bound weakly to its carboxyl-terminal extension [HAUSP(CT)] (lane 8, FIG. 9B), but did not bind to the core catalytic domain [HAUSP (M)] (lane 5, FIG. 9B).

To evaluate in vivo interactions by co-immunoprecipitation analysis, p53-null cells (H1299) were transfected with p53 and a Flag-tagged HAUSP expression vector. As shown in FIG. 1B, p53 was readily immunoprecipitated from the cells co-transfected with both Flag-HAUSP and p53 (lane 4), but not from cells transfected with p53 alone (lane 2).

By using the HAUSP-specific antibody, the inventors also examined the interaction between the endogenous p53 and HAUSP proteins. Western-blot analysis showed that p53 was present in the α-HAUSP immunoprecipitates from cell extracts of human lung carcinoma cells (H460), but not in the control immunoprecipitates obtained with the pre-immune serum (FIG. 1C). Interestingly, this interaction was strongly detected in cells subjected to genotoxic stress (lane 2 vs. lane 3, FIG. 1C), whereas only a slight enhancement was detected in the cells treated with a proteasome inhibitor, LLNL (lane 4, FIG. 1C). These results indicate that p53 interacts with HAUSP in vivo, and that the possible regulation of p53 by HAUSP may still be effective in the cells during the DNA damage response.

Figure 2:
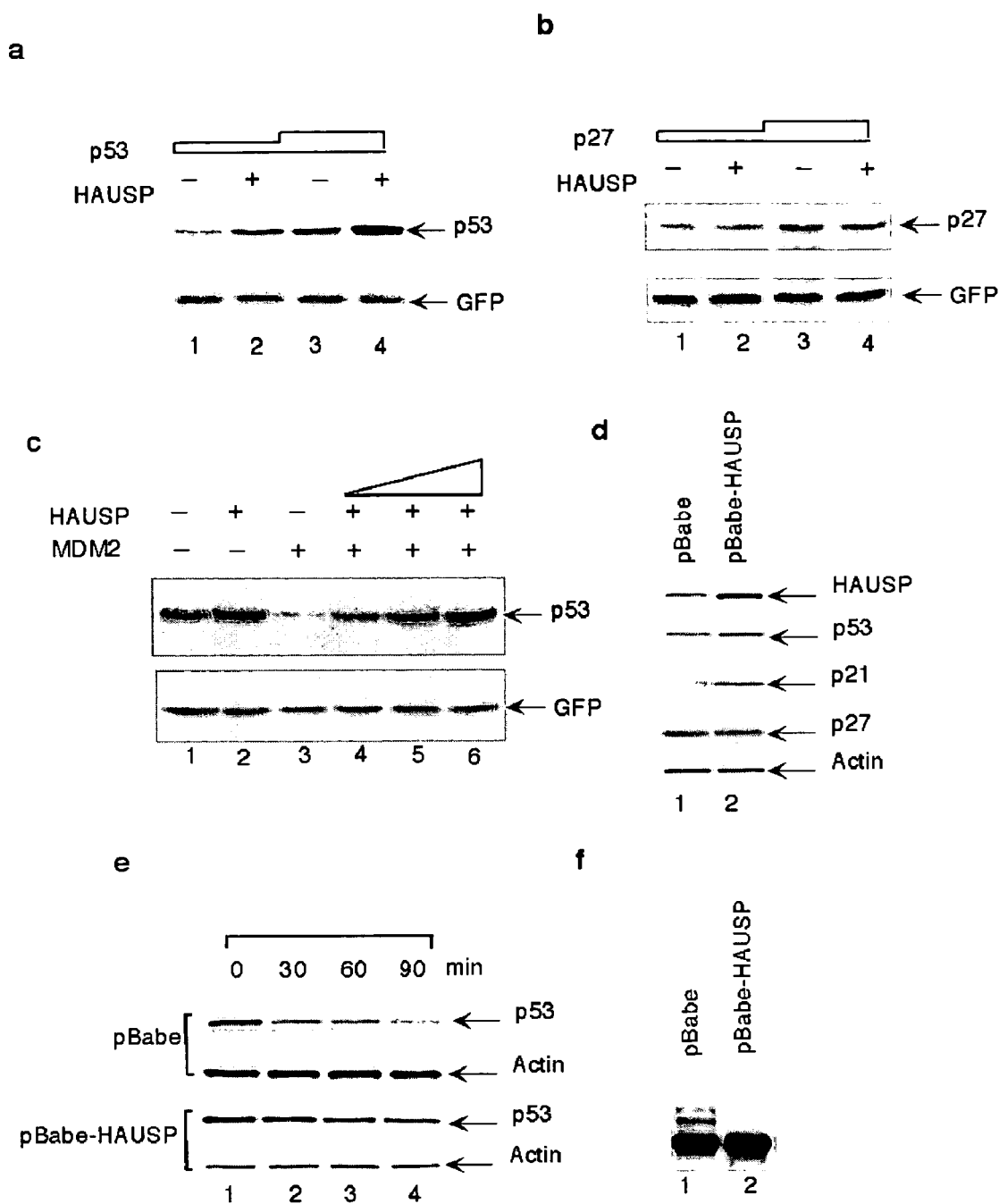
FIGS. 2A-2F demonstrate that HAUSP interacts with, and stabilizes, p53 in vivo. HAUSP enhanced the steady-state levels of p53 (A), but not p27 (B), according to Western-blot analyses of cell extracts from the H1299 cells transfected with p53 alone (lanes 1, 3), or co-transfected with p53 and HAUSP (lanes 2, 4), with the anti-p53 monoclonal antibody, DO-1. (A) Western-blot analysis of cell extracts from the H1299 cells transfected with p27 alone (lanes 1, 3), or co-transfected with p27 and HAUSP (lanes 2, 4), with the anti-p27 monoclonal antibody (B). (C) Protection of p53 from Mdm2-mediated degradation by HAUSP was illustrated using Western-blot analysis of extracts from the cells transfected with p53 (lane 1), or co-transfected with p53 and HAUSP (lane 2), or co-transfected with p53 and Mdm2 (lane 3), or in combination with different amounts of HAUSP (lanes 4-6), by the anti-p53 monoclonal antibody, DO-1. (D) HAUSP regulates the expression levels of endogenous proteins, as shown in cell extracts from both mock-infected and pBabe-HAUSP-infected IMR-90 cells, which were analyzed for expression levels of each protein by Western-blot analysis. (E) Regulation of the half-life of endogenous p53 by HAUSP. Cell extracts from both mock-infected and pBabe-HAUSP-infected IMR-90 cells, harvested at different time points as indicated after pre-treatment with cyclohexamide (CHX), were analyzed for p53 protein levels by Western blot with anti-p53 monoclonal antibody (DO-1). (F) Regulation of the ubiquitination levels of endogenous p53 by HAUSP. Cell extracts from mock-infected cells, and from pBabe-HAUSP-infected IMR-90 cells pre-treated with LLNL for 4 h, were first immunoprecipitated with anti-p53 polyclonal antibody, and then analyzed for ubiquitination levels by Western blot with anti-p53 monoclonal antibody (DO-1).

To determine the functional consequence of the p53-HAUSP interaction, the inventors tested whether HAUSP affects stabilization of p53. As indicated in FIG. 2A, HAUSP expression significantly increased the steady-state cellular levels of p53. In contrast, HAUSP had no obvious effect on the levels of p27 (FIG. 2B), another short-lived tumor-suppressor protein the stability of which is also regulated by the ubiquitination pathway (Slingerland and Pagano, Regulation of the cdk inhibitor p27 and its deregulation in cancer. *J. Cell Physi.,* 183:10-17, 2000). Moreover, as shown in FIG. 2C, HAUSP effectively rescues p53 from Mdm2-mediated degradation. Thus, although overexpression of Mdm2 significantly induced p53 degradation (lane 3 vs. 1, FIG. 2C), degradation of p53 was inhibited in a dose-dependent manner upon expression of HAUSP (lanes 4-6, FIG. 2C).

The inventors further examined the effect of HAUSP expression on stabilization of endogenous p53. Normal human fibroblast IMR-90 cells were infected with either a pBabe retrovirus empty vector or a pBabe retrovirus containing HAUSP. The inventors first examined the protein levels of endogenous p53 by Western-blot analysis. Significantly higher levels of p53 proteins were detected in the pBabe-HAUSP-infected cells (lane 2 vs. 1, FIG. 2D). Interestingly, expression of endogenous p21 was also induced (lane 2 vs. 1, FIG. 2D), consistent with transient transfection results (data not shown), thereby indicating that HAUSP also activates p53-dependent transcriptional activation. In contrast, the levels of endogenous p27 remained the same, supporting the notion that HAUSP stabilizes p53, but not p27, in vivo. Notably, the half-life of p53 in the pBabe-HAUSP-infected cells was significantly increased by HAUSP expression (from about 20 min to about 90 min), whereas the half-life of p53 in the mock-infected cells was less than 30 min (FIG. 2E). To corroborate these results, inventors also found that the ubiquitination levels of p53 in the pBabe-HAUSP infected cells were reduced as compared with the levels in the mock-infected cells (FIG. 2F). Thus, these data demonstrate that HAUSP specifically stabilizes p53 in vivo.

To investigate the biological role of HAUSP, the inventors examined the effect of HAUSP on cell growth in a colony-formation assay. A pair of human lung carcinoma cells (H1299 and H460) were infected with either an empty pBabe-puro control retrovirus or a pBabe-puro retrovirus encoding HAUSP, and cultured for 2 weeks under pharmacological selection. Strikingly, HAUSP strongly inhibited cell growth of H460 cells, which express wild-type p53, but had no significant effect on p53-null H1299 cells (FIG. 3A). Similar cell growth repression by HAUSP was also observed in MEF p53 (+/+) cells, but not in MEF p53 (−/−) cells (FIG. 3A), suggesting that cell-growth repression by HAUSP is p53-dependent.

The inventors also tested whether HAUSP directly affects p53-dependent apoptosis. H1299 cells were transfected with p53 alone, or co-transfected with p53 and Mdm2, or with p53, Mdm2 and HAUSP. After transfection, the cells were fixed, stained for p53, and analyzed for apoptotic cells (SubG1) according to DNA content (Luo et al., Deacetylation of p53 modulates its effect on cell growth and apoptosis. *Nature*, 408:377-81, 2000). As indicated in FIG. 3B, although overexpression of p53 alone induced significant apoptosis (31.0%), Mdm2 strongly reduced the level of p53-dependent apoptosis (11.2%). However, expression of HAUSP effectively attenuated the inhibitory effect of Mdm2 on p53-mediated apoptosis (28.5% vs. 11.2%, FIG. 3B). These data demonstrate that HAUSP is critically involved in the regulation of p53-dependent apoptosis, as well as cell growth inhibition.

To elucidate the molecular mechanism by which HAUSP stabilizes p53, the inventors tested whether HAUSP directly controls the levels of p53 ubiquitination in vivo. As indicated in FIG. 4A, a high level of ubiquitinated p53 was found in cells co-transfected with Mdm2 (lane 2); however, p53 ubiquitination was significantly abrogated by HAUSP expression (lane 3 vs. lane 2). In contrast, HAUSP had no effect on the levels of ubiquitinated p27 (data not shown). Notably, an unrelated human UBP family member (human USPI 1) (D'Andrea and Pellman, Deubiquitinating enzymes: a new class of biological regulators. *Crit. Rev. Biochem. Mol. Biol.*, 33:337-52, 1998; Chung and Baek, Deubiquitinating enzymes: their diversity and emerging roles. *Biochem. Biophys. Res. Commun.*, 266:633-40, 1999; Wilkinson, K. D., Signal transduction: aspirin, ubiquitin and cancer. *Nature*, 424:738-39, 2003), which is defective in p53-binding (data not shown), had no obvious effect on the levels of p53 ubiquitination (lane 5, FIG. 4A) or p53 stabilization (lane 5, FIG. 4B). Significantly, a HAUSP mutant with a short deletion at the core domain lost the ability to stabilize p53 (lane 4, FIG. 4B) or reduce the cellular levels of p53 ubiquitination (lane 4, FIG. 4A), indicating that stabilization of p53 by HAUSP requires its deubiquitinating enzymatic activity.

To further confirm the specific deubiquitination activity of HAUSP on p53, the inventors examined whether HAUSP can directly deubiquitinate p53 in a purified system. The HAUSP protein was expressed in bacteria, and purified to near homogeneity. The ubiquitinated form of p53 then was purified on the M2 affinity column, under high stringency conditions, from the cells transfected with a Flag-tagged p53 expression vector. The highly purified in vitro system was used in this assay in order to avoid possible contamination by either inhibitory factors (i.e., p14ARF) or any enzymes involving ubiquitination of p53. As shown in FIG. 4C, p53 was efficiently deubiquitinated upon incubation with purified recombinant HAUSP (lane 2). Thus, the foregoing results demonstrate that HAUSP can specifically deubiquitinate p53, both in vitro and in vivo.

Interestingly, a HAUSP point-mutant protein (HAUSP-cs), in which a highly conserved Cys residue at the core domain was replaced by Ser, retained its strong binding with p53 (FIG. 9); however, the mutant was functionally defective in deubiquitinating p53 in vitro (lane 3, FIG. 4C). Significantly, in contrast to the effect produced by the wild-type of HAUSP, expression of HAUSP-cs in the cells increased the level of p53 ubiquitination (lane 4 vs. 2, FIG. 5A), indicating that HAUSP-cs may function as a dominant-negative mutant by interfering with endogenous HAUSP-mediated deubiquitination of p53.

In order to corroborate these results, the inventors also tested whether HAUSP-cs expression affected the levels of p53 proteins in cells. As shown in FIG. 5B, co-expression of HAUSP-cs with p53 slightly, but significantly, decreased the levels of p53 proteins (lanes 1, 3 vs. lanes 2, 4). To demonstrate further that HAUSP regulates endogenous p53, the inventors introduced the point mutant (HAUSP-cs) into normal human cells. IMR-90 cells were infected with either a pBabe retrovirus empty vector or a pBabe retrovirus containing HAUSP-cs. As indicated in FIG. 5C, the levels of p53 proteins in the mock-infected cells were strongly induced by DNA damage (lanes 1, 3, 5). However, HAUSP-cs expression led to significant attenuation of p53 stabilization under both normal and DNA damage conditions (lanes 2, 4, 6). Taken together, these results suggest that HAUSP is critically involved in deubiquitination, as well as stabilization, of p53 under physiological conditions.

EXAMPLE 4

Co-Immunoprecipitation Analysis

Figure 8:
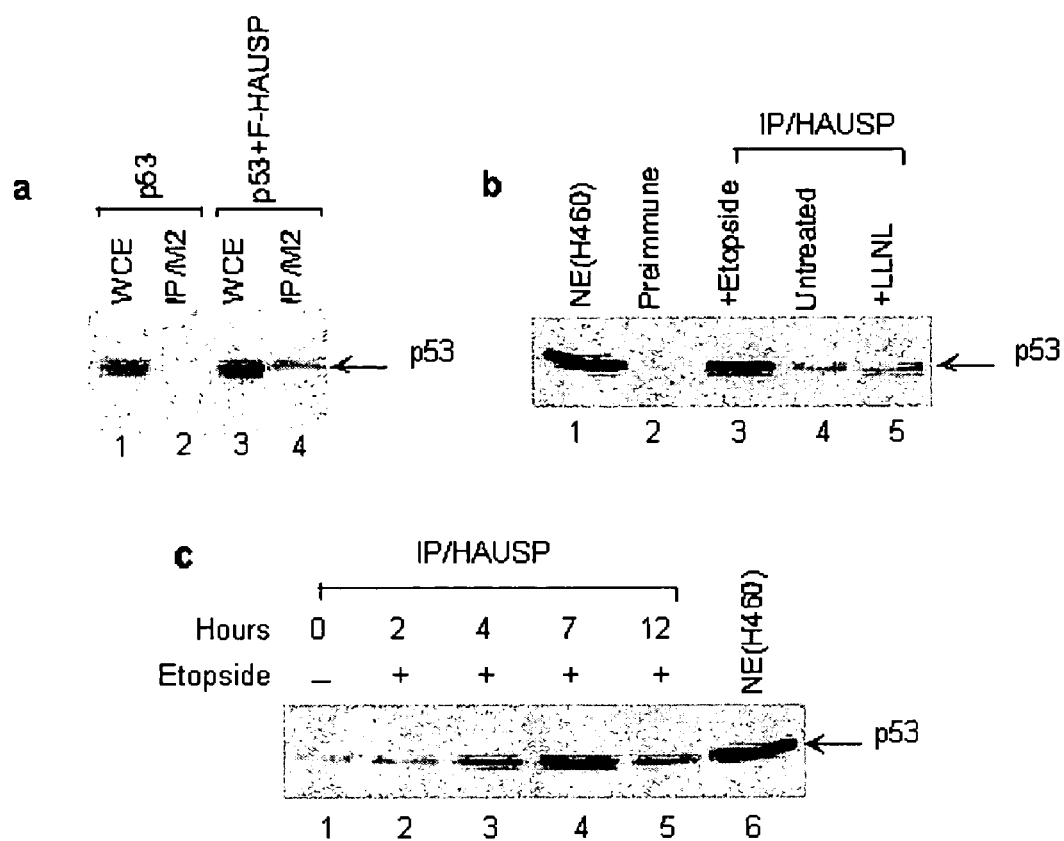
FIGS. 8A-8C illustrate p53 interaction with HAUSP in vivo. (A) p53 interacts with HAUSP in cells. Western-blot analyses of the indicated whole-cell extract (WCE) (lanes 1, 3) or the immunoprecipitates with M2 antibody (IP/M2) (lanes 2, 4) prepared from either F-HAUSP and p53 co-transfected H1299 cells (lanes 3, 4) or the p53-alone transfected cells (lanes 1, 2) with anti-p53 monoclonal antibody (DO-1). (B) The interaction between the endogenous p53 and HAUSP proteins. Western-blot analyses of the indicated nuclear extract (NE) (lanes 1), or control immunoprecipitates with pre-immunoserum (lane 2), or immunoprecipitates with anti-HAUSP antibody (IP/HAUSP) from cell extracts of either untreated (lane 4), DNA-damage-treated, or LLNL-treated H460 cells with the anti-p53 monoclonal antibody. (c) The interaction between p53 and HAUSP during the DNA damage response. Western-blot analyses of the H460 nuclear extract (NE) (lanes 6), or immunoprecipitates with anti-HAUSP antibody (IP/a-HAUSP) (lanes 1-5) derived from H460 cells harvested at the indicated time points after the DNA-damage treatment with the anti-p53 monoclonal antibody, DO-1.

To further evaluate in vivo interactions by co-immunoprecipitation analysis, p53-null cells (H1299) were transfected with p53 and a Flag-tagged HAUSP expression vector. As shown in FIG. 8A, p53 was readily immunoprecipitated from the cells co-transfected with both Flag-HAUSP and p53 (lane 4), but not from cells transfected with p53 alone (lane 2). By using the HAUSP-specific antibody, the inventors also examined the interaction between the endogenous p53 and HAUSP proteins. Western-blot analysis showed that p53 was present in the α-HAUSP immunoprecipitates from cell extracts of human lung carcinoma cells (H460) which express wild-type p53 (lane 4, FIG. 8B), but not in the control immunoprecipitates obtained with the pre-immune serum (lane 2, FIG. 8B). Interestingly, this interaction was shown to be much stronger in cells subjected to genotoxic stress (lane 3 vs. lane 4, FIG. 8B), whereas only a slight enhancement was detected in the cells treated with a proteasome inhibitor, LLNL (lane 5, FIG. 8B). Furthermore, enhancement of the p53-HAUSP interaction was observed as early as 2-4 h after DNA damage (FIG. 7C), strongly suggesting a critical role for HAUSP in regulating p53 stability during the DNA-damage response. Thus, in contrast to abrogation of the Mdm2-p53 interaction by DNA damage (Shieh et al., DNA damage-induced phosphorylation of p53 alleviates inhibition MDM2. *Cell*, 91:325-34, 1997) these results indicate that p53 interacts with HAUSP in vivo, and that this interaction is enhanced in the cells after DNA damage, consistent with the suggestion that endogenous HAUSP plays an important role in p53 stabilization.

EXAMPLE 5

Additional Plasmids and Antibodies

Plasmids and antibodies used in Examples 6-7 were prepared as follows. To construct the p53, Mdm2, HAUSP, and ubiquitin expression vectors, cDNA sequences corresponding to the full-length proteins were amplified by PCR from Marathon-Ready HeLa cDNA (Clontech) or other templates, and subcloned into a pGEX (GST) or pET-11(His$_6$) vector for expression in bacteria, or into a pcDNA3 vector for expression in mammalian cells. The FLAG epitope tag was introduced by PCR. To prepare mutant constructs, cDNA sequences corresponding to different regions were amplified, by PCR, from the above constructs, and subcloned for site-directed mutagenesis with the Gene Edit system (Promega). Monoclonal antibodies for p53 (DO-1) (Santa Cruz), p21 (Santa Cruz), GFP (Clontech), mouse ubiquitin (Calbiochem), c-Myc (Santa Cruz), and p27 (Calbiochem) were purchased from the indicated companies. MdmX and Mdm2 (4B2) monoclonal antibodies were generous gifts from J. Chen's and A. Levine's labs, respectively. MdmX antibody may also be obtained from IBL Co., Ltd. (Fujioka, JP). See Chen et al. (Mapping of the p53 and mdm-2 interaction domains. *Mol. Cell. Biol.*, 13:4107-14, 1993) for the Mdm2 (4B2) antibody.

For Mdm2 and HAUSP polyclonal antibodies, antiserum was raised in rabbits against the purified GST-Mdm2 (1-110) and GST-HAUSP (1-98) protein fragments, respectively, and further affinity-purified on the antigen column.

EXAMPLE 6

Ablation of Endogenous HAUSP by RNAi and shRNA

For efficient reduction of HAUSP levels in U2OS cells, a two-step process was used. First, the inventors established stable cell lines that express a HAUSP short-hairpin RNA (shRNA), essentially as previously described (Hemann et al., An epi-allelic series of p53 hypomorphs created by stable RNAi produces distinct tumor phenotypes in vivo. *Nat. Genet.*, 33:396-400, 2003). In brief, a 3' oligonucleotide was generated that corresponds to the following: homology to the U6 promoter, a 28-nt region of HAUSP (nt 133-161), an 8-nt spacer, the antisense of the HAUSP sequence, and the pol III termination site. The 5' oligonucleotide corresponded to the SP6 site at the 5' end of the U6 promoter. A pGEM vector containing the U6 promoter was used as a template for the PCR reaction. The product was then subcloned into the pGlow-TOPO vector (Invitrogen), and subsequently transfected into U2OS cells for clonal selection of stable lines by G418 resistance (Gibco). This method stably reduced HAUSP levels by half, and more than 10 cell lines were obtained with a similar effect.

For further reduction, the U2OS-HAUSP shRNA stable lines were transfected with a 21-nt siRNA duplex containing 3' dTdT overhangs corresponding to HAUSP mRNA—specifically, either HAUSP#1 (AAUGUGGC-CCUGAGUGAUGGA) (SEQ ID NO:8) or HAUSP#2 (AAGUCUUUGUACAGGCGGAUG) (SEQ ID NO:9) (Dharmacon). The same sequence (HAUSP#1-mutant) with 2 nucleotides changed (AAUGUGGGCCUGAGAGA UGGA) (SEQ ID NO:10) was used as a control. RNAi transfections were conducted using oligofectamine. Approximately 1 million cells were plated 24 h before transfection, on a 10-cm dish. The manufacturer's protocol (Invitrogen) was followed for all transfections. For others, RNAi-mediated ablation of endogenous HAUSP was also performed using the HAUSP 21-nucleotide siRNA duplex, as described above. These cells were then used in the assays described.

EXAMPLE 7

In Vitro Deubiquitination Assays

For preparation of ubiquitinated Mdm2 as substrate, 3 ng of bacterially-produced GST-Mdm2 was mixed with the other purified components, including 10 ng of E1, 20-100 ng of E2 (UbCH5a), and 5•g of His-ubiquitin, in 200•1 of reaction buffer (40 mM Tris, 5 mM MgCl$_2$, 2 mM ATP, and 2 mM DTT; pH 7.6). Each reaction was stopped after 60 min, at 37° C., by addition of 8 M urea wash buffer (Buffer A), followed by a 4-h incubation with Ni$^{2+}$-NTA-agarose beads at room temperature. Beads were then washed for 5 min with each of the following buffers: Buffer A (8 M urea, 0.1 M Na$_2$PO$_4$/ NaH$_2$PO$_4$, 0.01 M Tris/HCl (pH 8.0), 10 mM•-mercaptoethanol, and 0.2% Triton X-100) and Buffer B (8M Urea, 0.1 M Na$_2$PO$_4$/NaH$_2$PO$_4$, 0.01 M Tris/HCl (pH 6.3), 10 mM •-mercaptoethanol, and 0.2% Triton X-100). His$_6$-tagged ubiquitinated proteins were then eluted with elution buffer (100 mM NaCl, 20% glycerol, 20 mM Tris-HCl (pH 7.9), 200 mM imidazole, and 1 mM DTT) for 60 min at 4° C.

For preparation of ubiquitinated Flag-c-Myc and Flag-p53 substrates, 293 and HeLa cells were transfected with 10 µg of pCIN$_4$-Flag-Myc and 5 µg of pCIN4-Flag-p53, respectively. 24 h post-transfection, cells were treated with 25 µM of the proteasome inhibitors, MG132 and LLNL (Sigma), each for 6 h, and then lysed in Flag-lysis buffer. The cell extracts were immunoprecipitated with Flag monoclonal antibody (M2). For the deubiquitination assay, the eluate was then incubated with 100 ng of purified bacterially-expressed GST-HAUSP, GSTHAUSP-cs, or GST-UBP11, for 60 min, and subsequently resolved on 4-12% gradient gels for Western analysis.

Summarized below are results obtained by the inventors in connection with the experiments of Examples 5-7 above.

Figure 10:
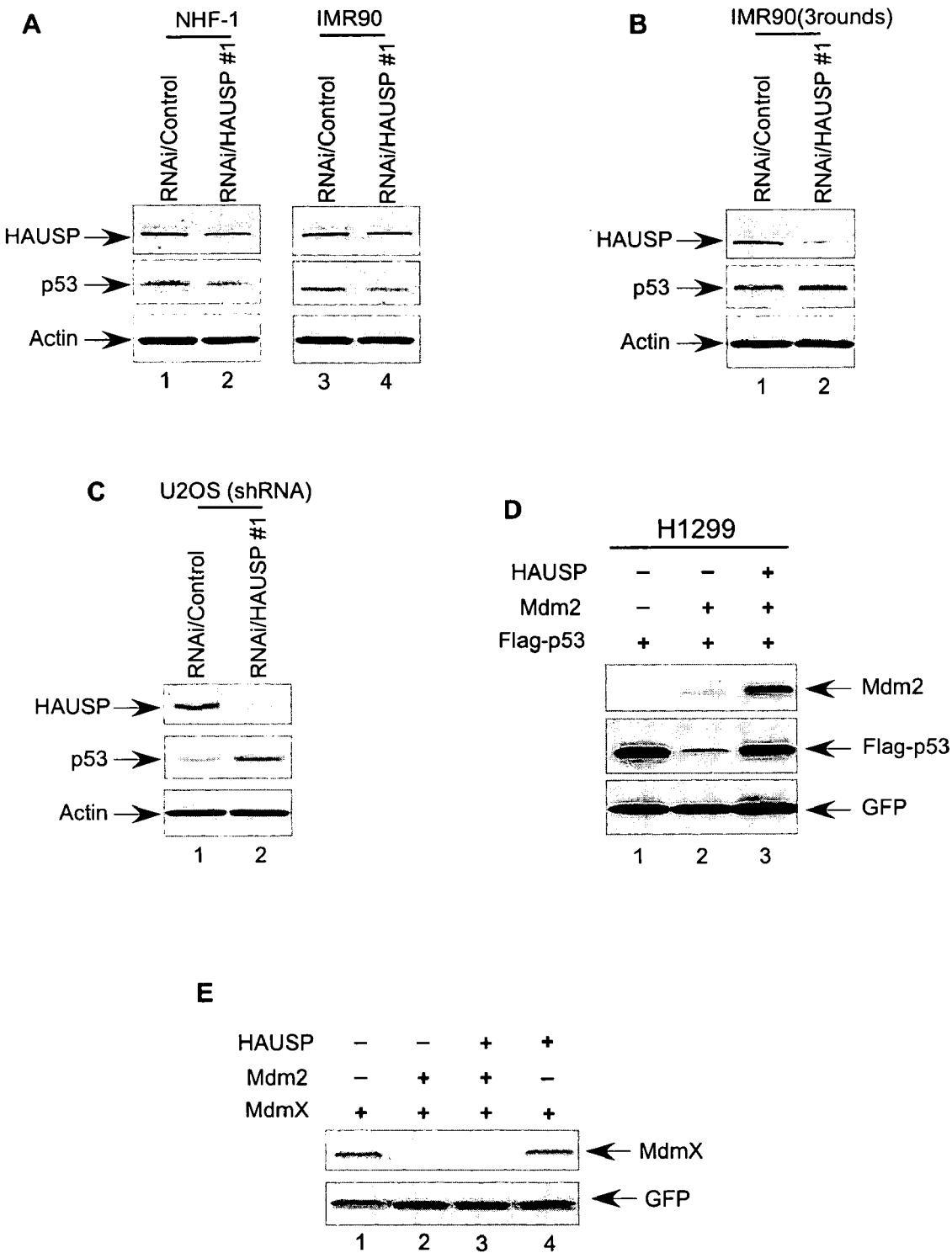
FIGS. 10A-10E illustrate stabilization of p53 and Mdm2 by HAUSP. (A) Western-blot analysis of whole-cell extracts after one round treatment of HAUSP#1-RNAi in NHF-1 cells and IMR90 cells. HAUSP#1 is AAUGUGGC-CCUGAGUGAUGGA (SEQ ID NO:8). (B) Western-blot analysis of IMR90 whole-cell extracts after three rounds of HAUSP#1-RNAi treatment. (C) The U2OS-HAUSP shRNA stable line was transiently transfected with one round of HAUSP#1-RNAi treatment. The blots were probed with anti-HAUSP, anti-p53 (DO-1), and anti-actin (AC-15) antibodies. (D) Western-blot analysis of whole-cell extracts from H1299 cells transfected with Flag-p53 alone (lane 1), Flag-p53 and Mdm2 (lane 2), or Flag-p53, Mdm2, and HAUSP (lane 3), with anti-p53 (DO-1), anti-Mdm2, anti-HAUSP, and anti-GFP antibodies. (E) Western-blot analysis of whole-cell extracts from H1299 cells transfected with MdmX alone (lane 1), MdmX and Mdm2 (lane 2), MdmX, Mdm2, and HAUSP (lane 3), or MdmX and HAUSP (lane 4). The blot was probed with anti-MdmX and anti-GFP monoclonal antibodies.

Differential Effects on the p53 Levels By RNAi-Mediated Reduction of Endogenous HAUSP To elucidate the role of HAUSP in vivo, the inventors examined the functional consequences of RNAi-mediated reduction of endogenous HAUSP. For this purpose, normal human fibroblasts (NHF-1 and IMR90), which express both HAUSP and wild-type p53 proteins, were transfected with either a HAUSP-specific RNA oligonucleotide (RNAi/ HAUSP#1) or a control GFP-specific RNA oligonucleotide (RNAi/control). As shown in FIG. 10A, the levels of endogenous HAUSP polypeptides were only partially reduced after one round of oligonucleotide transfection (top; lanes 2 and 4 vs. lanes 1 and 3), as HAUSP is a relatively stable protein. Under these conditions, the levels of endogenous p53 proteins were also mildly reduced, supporting a positive role for HAUSP in the stabilization of cellular p53.

Interestingly, after three consecutive rounds of transfection with HAUSP-specific RNA oligonucleotides, the levels of endogenous HAUSP proteins were almost completely depleted (FIG. 10B, top; lane 2 vs. lane 1). Surprisingly, however, severe ablation of HAUSP expression induced stabilization of p53 (middle; lane 2 vs. lane 1). To confirm this phenomenon, the inventors tested the effect of HAUSP ablation in another cell type using a different approach.

For efficient reduction of HAUSP levels in human osteosarcoma U2OS cells, a two-step process was used. First, the inventors established stable cell lines that express a HAUSP short-hairpin RNA (shRNA), essentially as described previously (Hemann et al., An epi-allelic series of p53 hypomorphs created by stable RNAi produces distinct tumor phenotypes in vivo. *Nat. Genet.*, 33:396-400, 2003). Thereafter, one round of transfection with the HAUSP-specific RNA oligonucleotides was used further to reduce the HAUSP levels in the U2OS-HAUSP shRNA stable lines. As shown in FIG. 10C, endogenous HAUSP proteins were nearly undetectable; again, however, the levels of endogenous p53 were significantly increased. Taken together, these results indicate that partial reduction of endogenous HAUSP levels by RNAi indeed destabilizes endogenous p53; unexpectedly, however, severe ablation of HAUSP expression conversely stabilizes endogenous p53.

HAUSP Expression also Stabilizes Mdm2

To understand the molecular mechanisms responsible for differential regulation of p53 levels by HAUSP, the inventors reasoned that, in addition to p53, other cellular factors may also be regulated by HAUSP, leading to indirect p53 stabilization in HAUSP-depleted cells. Accordingly, the inventors examined the effect of HAUSP on other key regulators in the p53 pathway. Interestingly, after transfecting H1299 cells (a p53-null, human lung carcinoma cell line) with expression vectors encoding p53, Mdm2, and HAUSP, the inventors observed elevated levels of Mdm2. Thus, as shown in FIG. 10D, while Mdm2-mediated p53 degradation was indeed strongly rescued by HAUSP expression, the levels of Mdm2 were also significantly enhanced. Similar results were also observed in human U2OS cells (FIG. 14, top panel), indicating that HAUSP can also stabilize Mdm2. In contrast, the inventors did not detect any significant effect on MdmX by HAUSP expression (FIG. 10E).

HAUSP Interacts with Mdm2 in the Absence of p53

Figure 11:
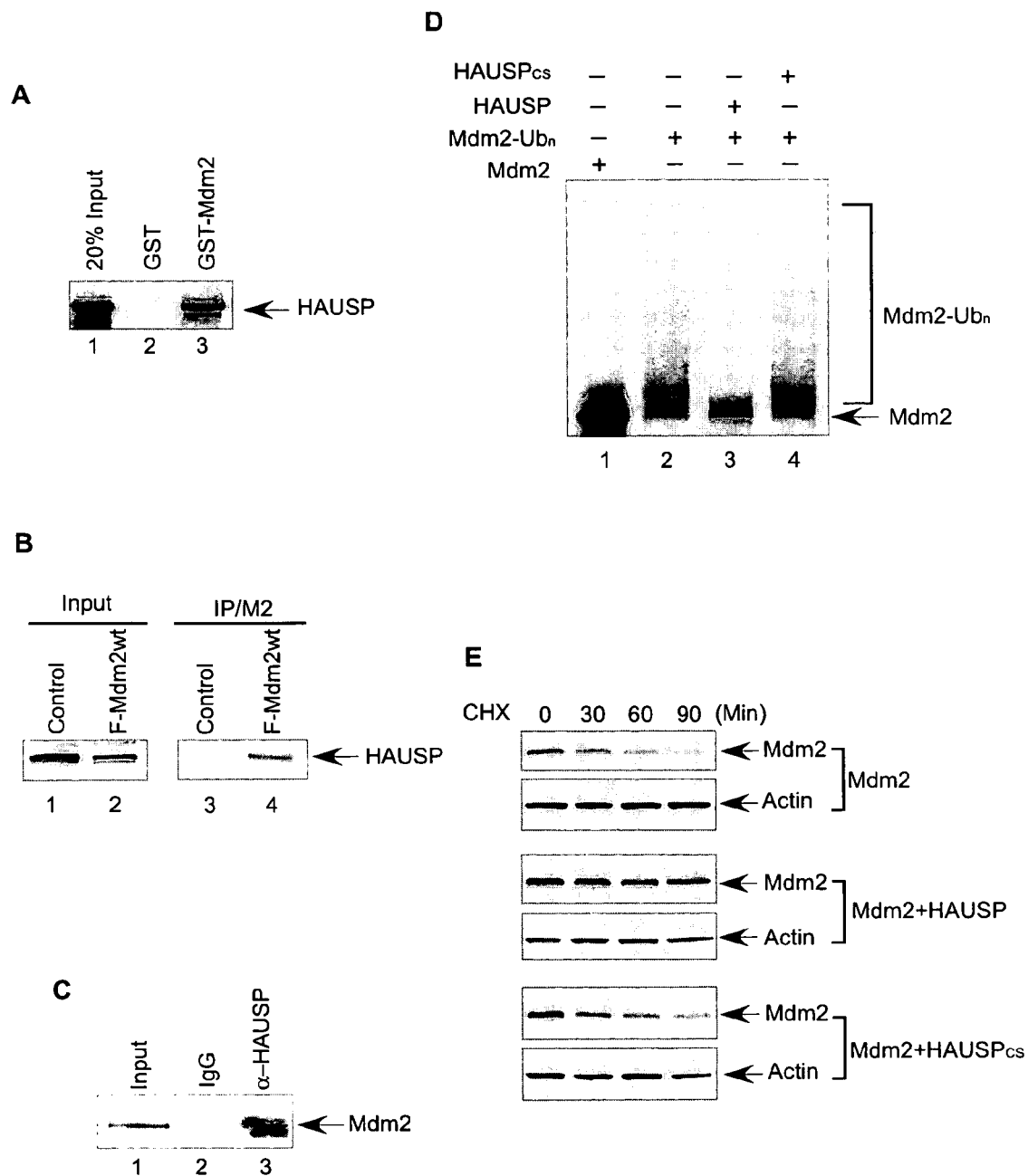

To determine whether HAUSP-mediated stabilization of Mdm2 is a direct effect, the inventors first examined whether HAUSP can bind Mdm2 in the absence of p53. As shown in FIG. 11A, $^{35}$S-labeled in-vitro-translated HAUSP was strongly bound to an immobilized GST-Mdm2 polypeptide, but not to GST alone (lane 3 vs. lane 2). The inventors next tested for p53-independent interaction between Mdm2 and HAUSP in H1299, a p53-null cell line. Since the endogenous levels of Mdm2 are extremely low in H1299 cells, the inventors generated a derivative cell line that stably expresses Flag-tagged wild-type human Mdm2. As shown in FIG. 11B, endogenous HAUSP was readily recovered from these cells by immunoprecipitation of Flag-Mdm2 with Flag-specific M2 antibody (lane 4). Using a HAUSP-specific antibody, the inventors also verified the interaction between endogenous HAUSP and Mdm2 proteins in U2OS cells. Western-blot analysis showed that Mdm2 is present in the anti-HAUSP immunoprecipitates from cell extracts of U2OS cells, but not in the control immunoprecipitates (FIG. 11C; lane 3 vs. lane 2). These results demonstrate a physical interaction between HAUSP and Mdm2 that is independent of p53.

Mdm2 is a Substrate of HAUSP-Mediated Deubiguitination

The inventors further sought to determine if HAUSP has an enzymatic role in Mdm2 stabilization. An in vitro deubiquitination assay was performed in which ubiquitinated Mdm2 was co-incubated with either recombinant HAUSP or the enzymatically deficient mutant HAUSP-cs. As shown in FIG. 11D, Mdm2 was significantly deubiquitinated in the presence of HAUSP, but not in the presence of HAUSP-cs. Notably, HAUSP failed to deubiquitinate ubiquitinated c-Myc proteins in vitro; an unrelated human deubiquitinase, UBP11, could deubiquitinate a non-specific substrate, but failed to deubiquitinate Mdm2 by similar assays (FIG. 14 (middle and bottom panels) and FIG. 15 (top panel)), confirming the specificity of HAUSP-mediated Mdm2 deubiquitination.

The inventors then tested the ability of HAUSP to stabilize Mdm2 in the absence of p53, by co-transfecting p53-null H1299 with Mdm2 and either wild-type or mutant HAUSP. As seen in FIG. 11E, Mdm2 is a short-lived protein in cells (top panel), but Mdm2 was strongly stabilized in the presence of wild-type HAUSP (middle panel), and the stabilization is severely abrogated by the catalytic mutant HAUSP-cs (bottom panel). These data indicate that HAUSP can directly regulate Mdm2 stability by deubiquitinating Mdm2 in the absence of p53.

Figure 12:
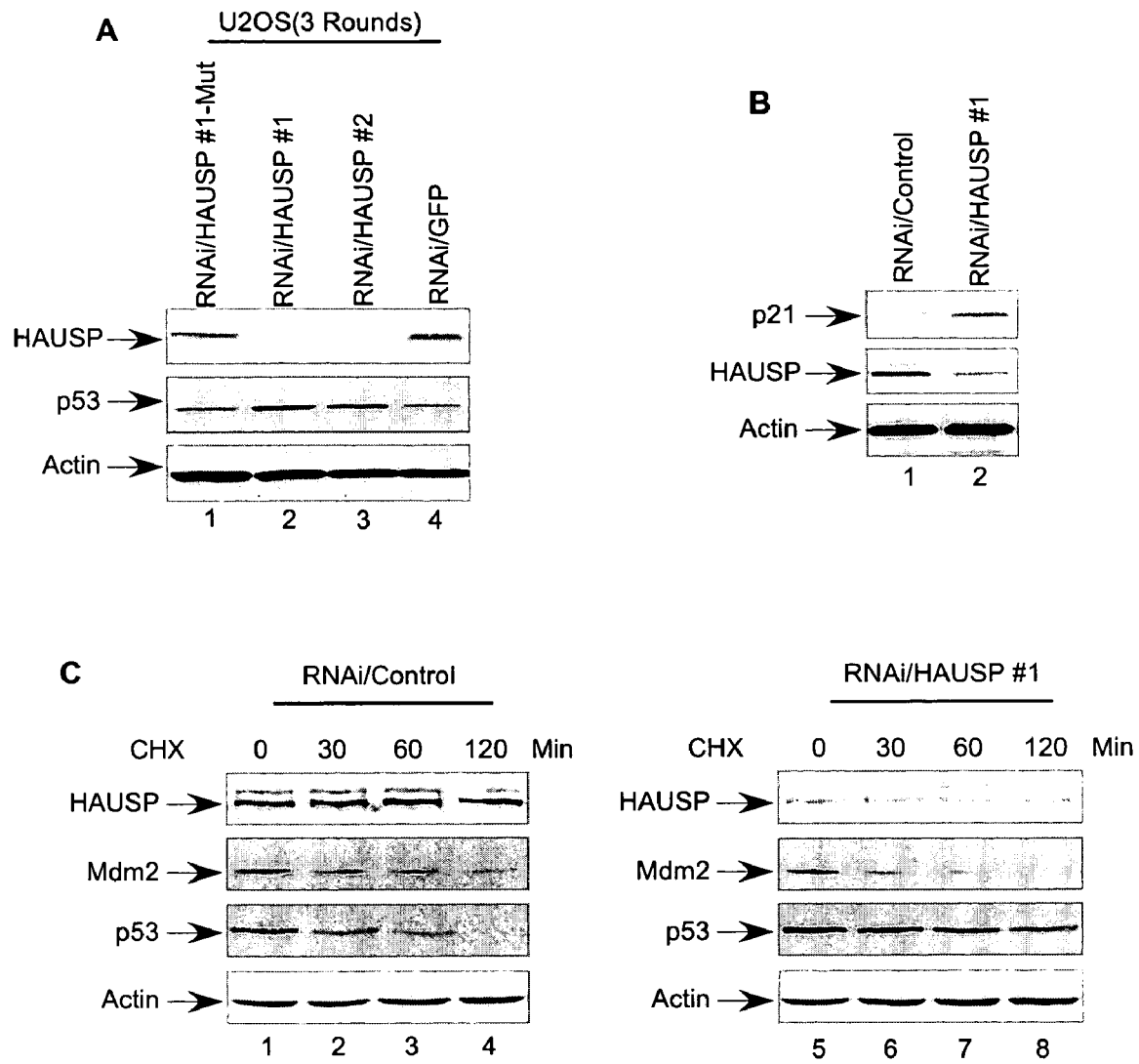
FIGS. 12A-12C demonstrate that p53 is stabilized and activated, but Mdm2 is extremely unstable, in HAUSP-depleted cells. (A) The effects of different HAUSP RNAi oligonucleotides. Western-blot analysis of the cell extracts from U2OS cells treated with 3 rounds of RNAi/HAUSP#1-mutant (lane 1), RNAi/HAUSP#1 (lane 2), RNAi/HAUSP#2 (lane 3), or RNAi/control (GFP) (lane 4). HAUSP#2 is AAGUCU-UUGUACAGGCGGAUG (SEQ ID NO:9). The blot was probed with anti-HAUSP, anti-p53 (DO-1), and anti-actin (AC-15) antibodies. (B) HAUSP ablation activates p21 expression. Whole-cell extracts of U2OS cells, treated with either control-RNAi (lane 1) or HAUSP #1-RNAi (lane 2), were immunoblotted with anti-p21, anti-HAUSP, and anti-actin (AC-15) antibodies. (C) Regulation of the half-life of endogenous Mdm2 and p53 by HAUSP. Cell extracts from both HAUSP#1-RNAi (right panel) and control-RNAi (left panel) U2OS cells—harvested at different time points, as indicated, after pretreatment with cyclohexamide—were analyzed for p53 and Mdm2 protein levels by Western blot using anti-p53 (DO-1) and anti-Mdm2 antibodies, respectively.

Mdm2 is Extremely Unstable in HAUSP-Ablated Cells, Leading to Indirect Activation of P53 Function To verify further the specific effects induced by HAUSP RNAi, the inventors performed similar assays using another HAUSP-specific RNA oligonucleotide, RNAi/HAUSP#2, which recognizes a different region of HAUSP mRNA. After three consecutive rounds of transfection, the levels of endogenous HAUSP proteins were almost completely ablated (FIG. 12A, top panel; lane 3 vs. lane 4), and, again, the levels of p53 were elevated by HAUSP depletion (FIG. 12A). These results are consistent with those presented in FIG. 10.

The inventors also conducted a control experiment, using a point mutant of HAUSP-specific RNA oligonucleotide. As shown in FIG. 12A, severe depletion of endogenous HAUSP resulted in p53 stabilization in U2OS cells by HAUSP-specific RNA oligonucleotide #1 (RNAi/HAUSP#1), but no significant effect was observed in the cells treated by HAUSP-specific RNA oligonucleotide #1 point mutant (RNAi/HAUSP#1-mut). Moreover, no significant effect on other short-lived proteins, such as c-Myc or p27, was observed by HAUSP depletion (FIG. 15, middle panel). Notably, HAUSP depletion also resulted in induction of p21 (FIG. 12B), a major transcriptional target of p53. These results demonstrate that p53 is stabilized and activated in HAUSP depleted cells.

The inventors further examined the effect on endogenous Mdm2 by HAUSP depletion. The mRNA levels of Mdm2 were elevated, because Mdm2 is also a transcriptional target of p53 (FIG. 15, bottom panel). However, strikingly, the half-life of endogenous Mdm2 became extremely short upon RNAi-mediated depletion of HAUSP (FIG. 12C). Therefore, while HAUSP overexpression stabilizes both Mdm2 and p53 (FIG. 10D), the net outcome of HAUSP depletion is stabilization and functional activation of p53, because Mdm2 is apparently too unstable to degrade p53 in the cells. This also suggests that, in HAUSP-ablated cells, the failure to deubiquitinate Mdm2 (which results in a reduction of Mdm2 activity and indirect activation of p53) overrides the expected destabilization of p53, due to loss of HAUSP-mediated p53 deubiquitination.

HAUSP-Mediated Feedback Regulation of p53 is Specific to Mdm2

To demonstrate the specific role of HAUSP in p53-Mdm2 regulation, the inventors tested whether the effect of p53 stabilization by HAUSP-depletion is Mdm2-dependent. Obviously, it is difficult to address this issue directly, since normal cells expressing wild-type p53 cannot survive by the loss of Mdm2. In HeLa cells, ubiquitination and degradation of p53 are controlled predominantly by human papilloma viral (HPV) protein E6, in combination with the cellular E6AP ubiquitin ligase (Hengstermann et al., Complete switch from Mdm2 to human papillomavirus E6-mediated degradation of p53 in cervical cancer cells. *Proc. Natl. Acad. Sci. USA*, 98:1218-23, 2001; Munger and Howley, Human papillomavirus immortalization and transformation functions. *Virus Res.*, 89:213-28, 2002). Therefore, the inventors first examined whether HAUSP also inhibits E6-mediated p53 degradation. As shown in FIG. 13A, overexpression of HAUSP effectively rescued E6-mediated degradation of p53 (lanes 4, 5 vs. lanes 2, 3). Moreover, ubiquitinated p53 proteins, purified from HeLa cells, were readily deubiquitinated by recombinant HAUSP (FIG. 13B; lane 2 vs. lane 1), but not by the deubiquitinase-deficient mutant HAUSP-cs (lane 3).

Since the Mdm2-dependent pathway of p53 ubiquitination is inactive in HeLa cells (Hengstermann et al., Complete switch from Mdm2 to human papillomavirus E6-mediated degradation of p53 in cervical cancer cells. *Proc. Natl. Acad. Sci. USA*, 98:1218-23, 2001), the direct effects of HAUSP overexpression on the rescue of E6-mediated degradation of p53 are unmasked in these cells. To confirm this interpretation, the inventors examined whether depletion of HAUSP expression in HeLa cells leads to different effects on p53. As shown in FIG. 13C, HAUSP depletion in HeLa cells reduced the levels of endogenous p53, and failed to activate p21, in contrast to the effect in U2OS cells. Thus, ablation of HAUSP-mediated deubiquitination further facilitates degradation of p53 in HeLa cells. These data suggest that HAUSP-mediated feedback regulation of p53 is specific to Mdm2, and also confirm the positive role of HAUSP in p53 stabilization in vivo.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for determining whether an agent modulates a Mdm2-herpesvirus-associated ubiquitin-specific protease (HAUSP) interaction, comprising the steps of:
   (a) obtaining or generating an in vitro system comprising Mdm2 and HAUSP;
   (b) contacting the in vitro system with a candidate agent; and
   (c) determining whether the candidate agent increases or decreases a level of Mdm2-HAUSP protein complex in the in vitro system,
   wherein determination of an increase or decrease the level of Mdm2-HAUSP protein complex in (c) indicates that the agent modulates Mdm2-HAUSP interaction.

2. The method of claim 1, wherein the determining in step (c) comprises comparing the level of Mdm2-herpesvirus-associated ubiquitin-specific protease (HAUSP) protein complex in the in vitro system of step (b) with a level of Mdm2-HAUSP protein complex in a second in vitro system comprising Mdm2 and HAUSP in the absence of the candidate agent, wherein determination of an increase or decrease of the level of Mdm2-HAUSP protein complex in the in vitro system of step (b) compared to the second in vitro system indicates that the agent modulates Mdm2-HAUSP interaction.

3. A method for determining whether an agent is reactive with Mdm2 or herpesvirus-associated ubiqiuitin-specific protease (HAUSP), comprising the steps of:
   (a) contacting a candidate agent with either (i) Mdm2, in the presence of HAUSP, or (ii) HAUSP, in the presence of Mdm2; and
   (b) determining whether the candidate agent inhibits Mdm2-HAUSP protein complex formation,
   wherein determination of inhibition of Mdm2-HAUSP protein complex formation in (b) compared to Mdm2-HAUSP protein complex formation in the absence of the agent indicates that the agent is reactive with Mdm2 or HAUSP.

4. A method for determining whether an agent modulates Mdm2-herpesvirus-associated ubiquitin-specific protease (HAUSP) interaction, comprising the steps of:
   (a) obtaining or generating a first in vitro system comprising Mdm2 and HAUSP, and a second in vitro system comprising Mdm2 and HAUSP;
   (b) contacting the first system with a candidate agent;
   (c) contacting the second system with (i) the candidate agent and (ii) an antibody, or fragment thereof, that specifically binds Mdm2; and
   (d) determining a level of HAUSP activity in the first system and the second system,
   wherein determination of an increase or decrease of HAUSP activity in the first system compared to the second system indicates that the agent modulates Mdm2-HAUSP interaction.

5. A method for determining whether an agent modulates Mdm2-herpesvirus-associated ubiquitin-specific protease (HAUSP) interaction, comprising the steps of:
   (a) obtaining or generating a first in vitro system comprising Mdm2 and HAUSP, and a second in vitro system comprising Mdm2 and HAUSP;
   (b) contacting the first system with a candidate agent;
   (c) contacting the second system with (i) the candidate agent and (ii) an antibody, or fragment thereof, that specifically binds HAUSP; and
   (d) determining a level of Mdm2 activity in the first system and the second system,
   wherein determination of an increase or decrease of Mdm2 activity in the first system compared to the second system indicates that the agent modulates Mdm2-HAUSP interaction.

6. The method of claim 3, further comprising the steps of:
   (c) contacting a cell with the candidate agent, wherein the cell comprises Mdm2, herpesvirus-associated ubiquitin-specific protease (HAUSP), or p53; and
   (d) determining whether the agent activates or increases, or inhibits or decreases, one or more Mdm2-associated, HAUSP-associated, or p53-associated biological events in the cell, compared to a cell not contacted with the candidate agent.

* * * * *

SEQUENCE LISTING

```
<160> NUMBER OF SEQ ID NOS: 10

<210> SEQ ID NO 1
<211> LENGTH: 13
<212> TYPE: PRT
<213> ORGANISM: Homo sapiens

<400> SEQUENCE: 1

Tyr Asp Ala Gly Glu His Gly Leu Gln Glu Ala Glu Lys
1               5                   10

<210> SEQ ID NO 2
<211> LENGTH: 13
<212> TYPE: PRT
<213> ORGANISM: Homo sapiens

<400> SEQUENCE: 2

Asp Phe Glu Pro Gln Pro Gly Asn Met Ser His Pro Arg
1               5                   10

<210> SEQ ID NO 3
<211> LENGTH: 8
<212> TYPE: PRT
<213> ORGANISM: Homo sapiens

<400> SEQUENCE: 3

Lys Leu Tyr Tyr Gln Gln Leu Lys
1               5

<210> SEQ ID NO 4
<211> LENGTH: 12
<212> TYPE: PRT
<213> ORGANISM: Homo sapiens

<400> SEQUENCE: 4

Phe Met Tyr Asp Pro Gln Thr Asp Gln Asn Ile Lys
1               5                   10

<210> SEQ ID NO 5
<211> LENGTH: 10
<212> TYPE: PRT
<213> ORGANISM: Homo sapiens

<400> SEQUENCE: 5

Ile Gln Asp Tyr Asp Val Ser Leu Asp Lys
1               5                   10
```

<210> SEQ ID NO 6
<211> LENGTH: 1102
<212> TYPE: PRT
<213> ORGANISM: Homo sapiens

<400> SEQUENCE: 6

```
Met Asn His Gln Gln Gln Gln Gln Gln Lys Ala Gly Glu Gln Gln
1               5                   10                  15

Leu Ser Glu Pro Glu Asp Met Glu Met Glu Ala Gly Asp Thr Asp Asp
            20                  25                  30

Pro Pro Arg Ile Thr Gln Asn Pro Val Ile Asn Gly Asn Val Ala Leu
        35                  40                  45

Ser Asp Gly His Asn Thr Ala Glu Glu Asp Met Glu Asp Asp Thr Ser
    50                  55                  60

Trp Arg Ser Glu Ala Thr Phe Gln Phe Thr Val Glu Arg Phe Ser Arg
65                  70                  75                  80

Leu Ser Glu Ser Val Leu Ser Pro Pro Cys Phe Val Arg Asn Leu Pro
                85                  90                  95

Trp Lys Ile Met Val Met Pro Arg Phe Tyr Pro Asp Arg Pro His Gln
            100                 105                 110

Lys Ser Val Gly Phe Phe Leu Gln Cys Asn Ala Glu Ser Asp Ser Thr
        115                 120                 125

Ser Trp Ser Cys His Ala Gln Ala Val Leu Lys Ile Ile Asn Tyr Arg
    130                 135                 140

Asp Asp Glu Lys Ser Phe Ser Arg Arg Ile Ser His Leu Phe Phe His
145                 150                 155                 160

Lys Glu Asn Asp Trp Gly Phe Ser Asn Phe Met Ala Trp Ser Glu Val
                165                 170                 175

Thr Asp Pro Glu Lys Gly Phe Ile Asp Asp Asp Lys Val Thr Phe Glu
            180                 185                 190

Val Phe Val Gln Ala Asp Ala Pro His Gly Val Ala Trp Asp Ser Lys
        195                 200                 205

Lys His Thr Gly Tyr Val Gly Leu Lys Asn Gln Gly Ala Thr Cys Tyr
    210                 215                 220

Met Asn Ser Leu Leu Gln Thr Leu Phe Phe Thr Asn Gln Leu Arg Lys
225                 230                 235                 240

Ala Val Tyr Met Met Pro Thr Glu Gly Asp Asp Ser Lys Ser Val
                245                 250                 255

Pro Leu Ala Leu Gln Arg Val Phe Tyr Glu Leu Gln His Ser Asp Lys
            260                 265                 270

Pro Val Gly Thr Lys Lys Leu Thr Lys Ser Phe Gly Trp Glu Thr Leu
        275                 280                 285

Asp Ser Phe Met Gln His Asp Val Gln Glu Leu Cys Arg Val Leu Leu
    290                 295                 300

Asp Asn Val Glu Asn Lys Met Lys Gly Thr Cys Val Glu Gly Thr Ile
305                 310                 315                 320

Pro Lys Leu Phe Arg Gly Lys Met Val Ser Tyr Ile Gln Cys Lys Glu
                325                 330                 335

Val Asp Tyr Arg Ser Asp Arg Arg Glu Asp Tyr Tyr Asp Ile Gln Leu
            340                 345                 350

Ser Ile Lys Gly Lys Lys Asn Ile Phe Glu Ser Phe Val Asp Tyr Val
        355                 360                 365

Ala Val Glu Gln Leu Asp Gly Asp Asn Lys Tyr Asp Ala Gly Glu His
    370                 375                 380
```

```
Gly Leu Gln Glu Ala Glu Lys Gly Val Lys Phe Leu Thr Leu Pro Pro
385                 390                 395                 400

Val Leu His Leu Gln Leu Met Arg Phe Met Tyr Asp Pro Gln Thr Asp
            405                 410                 415

Gln Asn Ile Lys Ile Asn Asp Arg Phe Glu Phe Pro Glu Gln Leu Pro
        420                 425                 430

Leu Asp Glu Phe Leu Gln Lys Thr Asp Pro Lys Asp Pro Ala Asn Tyr
            435                 440                 445

Ile Leu His Ala Val Leu Val His Ser Gly Asp Asn His Gly His His
        450                 455                 460

Tyr Val Val Tyr Leu Asn Pro Lys Gly Asp Gly Lys Trp Cys Lys Phe
465                 470                 475                 480

Asp Asp Asp Val Val Ser Arg Cys Thr Lys Glu Glu Ala Ile Glu His
                485                 490                 495

Asn Tyr Gly Gly His Asp Asp Leu Ser Val Arg His Cys Thr Asn
            500                 505                 510

Ala Tyr Met Leu Val Tyr Ile Arg Glu Ser Lys Leu Ser Glu Val Leu
        515                 520                 525

Gln Ala Val Thr Asp His Asp Ile Pro Gln Gln Leu Val Glu Arg Leu
        530                 535                 540

Gln Glu Glu Lys Arg Ile Glu Ala Gln Lys Arg Lys Glu Arg Gln Glu
545                 550                 555                 560

Ala His Leu Tyr Met Gln Val Gln Ile Val Ala Glu Asp Gln Phe Cys
            565                 570                 575

Gly His Gln Gly Asn Asp Met Tyr Asp Glu Glu Lys Val Lys Tyr Thr
            580                 585                 590

Val Phe Lys Val Leu Lys Asn Ser Ser Leu Ala Glu Phe Val Gln Ser
        595                 600                 605

Leu Ser Gln Thr Met Gly Phe Pro Gln Asp Gln Ile Arg Leu Trp Pro
610                 615                 620

Met Gln Ala Arg Ser Asn Gly Thr Lys Arg Pro Ala Met Leu Asp Asn
625                 630                 635                 640

Glu Ala Asp Gly Asn Lys Thr Met Ile Glu Leu Ser Asp Asn Glu Asn
            645                 650                 655

Pro Trp Thr Ile Phe Leu Glu Thr Val Asp Pro Glu Leu Ala Ala Ser
            660                 665                 670

Gly Ala Thr Leu Pro Lys Phe Asp Lys Asp His Asp Val Met Leu Phe
        675                 680                 685

Leu Lys Met Tyr Asp Pro Lys Thr Arg Ser Leu Asn Tyr Cys Gly His
        690                 695                 700

Ile Tyr Thr Pro Ile Ser Cys Lys Ile Arg Asp Leu Leu Pro Val Met
705                 710                 715                 720

Cys Asp Arg Ala Gly Phe Ile Gln Asp Thr Ser Leu Ile Leu Tyr Glu
            725                 730                 735

Glu Val Lys Pro Asn Leu Thr Glu Arg Ile Gln Asp Tyr Asp Val Ser
            740                 745                 750

Leu Asp Lys Ala Leu Asp Glu Leu Met Asp Gly Asp Ile Ile Val Phe
        755                 760                 765

Gln Lys Asp Asp Pro Glu Asn Asp Asn Ser Glu Leu Pro Thr Ala Lys
        770                 775                 780

Glu Tyr Phe Arg Asp Leu Tyr His Arg Val Asp Val Ile Phe Cys Asp
785                 790                 795                 800
```

```
Lys Thr Ile Pro Asn Asp Pro Gly Phe Val Thr Leu Ser Asn Arg
            805                 810                 815
Met Asn Tyr Phe Gln Val Ala Lys Thr Val Ala Gln Arg Leu Asn Thr
        820                 825                 830
Asp Pro Met Leu Leu Gln Phe Lys Ser Gln Gly Tyr Arg Asp Gly
            835                 840                 845
Pro Gly Asn Pro Leu Arg His Asn Tyr Glu Gly Thr Leu Arg Asp Leu
    850                 855                 860
Leu Gln Phe Phe Lys Pro Arg Gln Pro Lys Lys Leu Tyr Tyr Gln Gln
865                 870                 875                 880
Leu Lys Met Lys Ile Thr Asp Phe Glu Asn Arg Ser Phe Lys Cys
            885                 890                 895
Ile Trp Leu Asn Ser Gln Phe Arg Glu Glu Ile Thr Leu Tyr Pro
        900                 905                 910
Asp Lys His Gly Cys Val Arg Asp Leu Leu Glu Glu Cys Lys Lys Ala
            915                 920                 925
Val Glu Leu Gly Glu Lys Ala Ser Gly Lys Leu Arg Leu Leu Glu Ile
    930                 935                 940
Val Ser Tyr Lys Ile Ile Gly Val His Gln Glu Asp Glu Leu Leu Glu
945                 950                 955                 960
Cys Leu Ser Pro Ala Thr Ser Arg Thr Phe Arg Ile Glu Glu Ile Pro
            965                 970                 975
Leu Asp Gln Val Asp Ile Asp Lys Glu Asn Glu Met Leu Val Thr Val
                980                 985                 990
Ala His Phe His Lys Glu Val Phe  Gly Thr Phe Gly Ile  Pro Phe Leu
            995                 1000                1005
Leu Arg Ile His Gln Gly Glu  His Phe Arg Glu Val  Met Lys Arg
    1010                1015                1020
Ile Gln Ser Leu Leu Asp Ile  Gln Glu Lys Glu Phe  Glu Lys Phe
    1025                1030                1035
Lys Phe Ala Ile Val Met Thr  Gly Arg His Gln Tyr  Ile Asn Glu
    1040                1045                1050
Asp Glu Tyr Glu Val Asn Leu  Lys Asp Phe Glu Pro  Gln Pro Gly
    1055                1060                1065
Asn Met Ser His Pro Arg Pro  Trp Leu Gly Leu Asp  His Phe Asn
    1070                1075                1080
Lys Ala Pro Lys Arg Ser Arg  Tyr Thr Tyr Leu Glu  Lys Ala Ile
    1085                1090                1095
Lys Ile His Asn
    1100

<210> SEQ ID NO 7
<211> LENGTH: 4022
<212> TYPE: DNA
<213> ORGANISM: Homo sapiens

<400> SEQUENCE: 7
gtacgtgcgc gtctccctgc cgccgccgcc gccgccgcg ggccgccccg gggccgccgt      60
cgccgacgac gcgcgggagg aggaggagga ggccgccccg ccgccgccgc cgccgccgcc    120
gccccggctc gccgccgccc gccgccgggg ctcgcagccc cggccccgg ccgcaggcga     180 ggcccaggcc gcggccgaca tgaaccacca gcagcagcag cagcagcaga aagcgggcga    240
gcagcagttg agcgagcccg aggacatgga gatggaagcg ggagatacag atgacccacc    300
aagaattact cagaaccctg tgatcaatgg gaatgtggcc ctgagtgatg acacaacac     360
```

```
cgcggaggag gacatggagg atgacaccag ttggcgctcc gaggcaacct ttcagttcac      420
tgtggagcgc ttcagcagac tgagtgagtc ggtccttagc cctccgtgtt ttgtgcgaaa      480
tctgccatgg aagattatgg tgatgccacg cttttatcca gacagaccac accaaaaaag      540
cgtaggattc tttctccagt gcaatgctga atctgattcc acgtcatggt cttgccatgc      600
acaagcagtg ctgaagataa taaattacag agatgatgaa aagtcgttca gtcgtcgtat      660
tagtcatttg ttcttccata agaaaatga ttggggattt tccaattta tggcctggag       720 tgaagtgacc gatcctgaga aaggatttat agatgatgac aaagttacct ttgaagtctt      780
tgtacaggcg gatgctcccc atggagttgc gtgggattca agaagcaca caggctacgt       840 cggcttaaag aatcagggag cgacttgtta catgaacagc ctgctacaga cgttatttt       900 cacgaatcag ctacgaaagg ctgtgtacat gatgccaacc gaggggggatg attcgtctaa     960 aagcgtccct ttagcattac aaagagtgtt ctatgaatta cagcatagtg ataaacctgt     1020
aggaacaaaa aagttaacaa agtcatttgg gtgggaaact ttagatagct tcatgcaaca    1080
tgatgttcag gagctttgtc gagtgttgct cgataatgtg gaaaataaga tgaaaggcac    1140
ctgtgtagag ggcaccatac ccaaattatt ccgcggcaaa atggtgtcct atatccagtg    1200
taaagaagta gactatcggt ctgatagaag agaagattat tatgatatcc agctaagtat    1260
caaaggaaag aaaaatatat ttgaatcatt tgtggattat gtggcagtag aacagctcga    1320
tggggacaat aaatacgacg ctggggaaca tggcttacag gaagcagaga aggtgtgaa     1380 attcctaaca ttgccaccag tgttacatct acaactgatg agatttatgt atgaccctca    1440
gacggaccaa aatatcaaga tcaatgatag gttgaattc ccagagcagt taccacttga     1500
tgaatttttg caaaaaacag atcctaagga ccctgcaaat tatattcttc atgcagtcct    1560
ggttcatagt ggagataatc atggtggaca ttatgtggtt tatctaaacc ccaaagggga    1620
tggcaaatgg tgtaaatttg atgacgacgt ggtgtcaagg tgtactaaag aggaagcaat    1680
tgagcacaat tatgggggtc acgatgacga cctgtctgtt cgacactgca ctaatgctta    1740
catgttagtc tacatcaggg aatcaaaact gagtgaagtt ttacaggcgg tcaccgacca    1800
tgatattcct cagcagttgg tggagcgatt acaagaagag aaaaaggatcg aggctcagaa   1860 gcggaaggag cggcaggaag cccatctcta tatgcaagtg cagatagtcg cagaggacca    1920
gttttgtggc caccaaggga atgacatgta cgatgaagaa aaagtgaaat acactgtgtt    1980
caaagtattg aagaactcct cgcttgctga gtttgttcag agcctctctc agaccatggg    2040
atttccacaa gatcaaattc gattgtggcc catgcaagca aggagtaatg aacaaaacg    2100 accagcaatg ttagataatg aagccgacgg caataaaaca atgattgagc tcagtgataa   2160
tgaaaaccct tggacaatat tcctggaaac agttgatccc gagctggctg ctagtggagc    2220
gaccttaccc aagtttgata agatcatga tgtaatgtta tttttgaaga tgtatgatcc     2280
caaaacgcgg agcttgaatt actgtgggca tatctacaca ccaatatcct gtaaaatacg    2340
tgacttgctc ccagttatgt gtgacagagc aggatttatt caagatacta gccttatcct    2400
ctatgaggaa gttaaaccga atttaacaga gagaattcag gactatgacg tgtctcttga    2460
taaagccctt gatgaactaa tggatggtga catcatagta tttcagaagg atgaccctga    2520
aaatgataac agtgaattac ccaccgcaaa ggagtatttc cgagatctct accaccgcgt    2580
tgatgtcatt ttctgtgata aaacaatccc taatgatcct ggatttgtgg ttacgttatc    2640
aaatagaatg aattatttc aggttgcaaa gacagttgca cagaggctca acacagatcc     2700
aatgttgctg cagtttttca gtctcaagg ttatagggat ggcccaggta atcctcttag     2760
```

```
acataattat gaaggtactt taagagatct tctacagttc ttcaagccta gacaacctaa    2820
gaaactttac tatcagcagc ttaagatgaa aatcacagac tttgagaaca ggcgaagttt    2880
taaatgtata tggttaaaca gccaatttag ggaagaggaa ataacactat atccagacaa    2940
gcatgggtgt gtccgggacc tgttagaaga atgtaaaaag gccgtggagc ttggggagaa    3000
agcatcaggg aaacttaggc tgctagaaat tgtaagctac aaaatcattg gtgttcatca    3060
agaagatgaa ctattagaat gtttatctcc tgcaacgagc cggacgtttc gaatagagga    3120
aatccctttg gaccaggtgg acatagacaa agagaatgag atgcttgtca cagtggcgca    3180
tttccacaaa gaggtcttcg gaacgttcgg aatcccgttt ttgctgagga tacaccaggg    3240
cgagcatttt cgagaagtga tgaagcgaat ccagagcctg ctggacatcc aggagaagga    3300
gtttgagaag tttaaatttg caattgtaat gacgggccga caccagtaca taatgaaga    3360 cgagtatgaa gtaaatttga aagactttga gccacagccc ggtaatatgt ctcatcctcg    3420
gccttggcta gggctcgacc acttcaacaa agccccaaag aggagtcgct acacttacct    3480
tgaaaaggcc attaaaatcc ataactgatt tccaagctgg tgtgttcaag gcgaggacgg    3540
tgtgtgggtg gccccttaac agcctagaac tttggtgcac gtgccctcta gccgaagtct    3600
tcagcaagag gattcgctgc tggtgttaat tttattttat tgaggctgtt cagtttggct    3660
tctctgtatc tattgactgc ccttttttgag caaaatgaag atgttttat aaagcttgga    3720 tgccaatgag agttatttta tggtaaccac agtgcaaggc aactgtcagc gcaatggggg    3780
agaagaggtt agtggatcgg gggtccctgg ctcaaggtct ctgggctgtc cctagtgggc    3840
acgagtggct cggctgcctt cctggggtcc cgtgcaccag ccctgcagct agcaagtctt    3900
gtgtttaggc tcgtctgacc tatttccttc agttatactt tcaatgacct tttgtgcatc    3960
tgttaaggca aaacagagaa actcacaacc taataaatag cgctcttccc ttcaaaaaaa    4020
aa                                                                   4022

<210> SEQ ID NO 8
<211> LENGTH: 21
<212> TYPE: RNA
<213> ORGANISM: artificial sequence
<220> FEATURE:
<223> OTHER INFORMATION: shRNA for use in RNAi

<400> SEQUENCE: 8
aauguggccc ugagugaugg a                                              21

<210> SEQ ID NO 9
<211> LENGTH: 21
<212> TYPE: RNA
<213> ORGANISM: artificial sequence
<220> FEATURE:
<223> OTHER INFORMATION: shRNA for use in RNAi

<400> SEQUENCE: 9
aagucuuugu acaggcggau g                                              21

<210> SEQ ID NO 10
<211> LENGTH: 21
<212> TYPE: RNA
<213> ORGANISM: artificial sequence
<220> FEATURE:
<223> OTHER INFORMATION: shRNA for use in RNAi

<400> SEQUENCE: 10
aaugugggcc ugagagaugg a                                              21
```